United States Patent [19]
Naughton et al.

[11] Patent Number: 5,580,781
[45] Date of Patent: Dec. 3, 1996

[54] THREE-DIMENSIONAL TUMOR CELL AND TISSUE CULTURE SYSTEM

[75] Inventors: Gail K. Naughton; Brian A. Naughton, both of Groton, Vt.

[73] Assignee: Advanced Tissue Sciences, Inc., La Jolla, Calif.

[21] Appl. No.: 417,541

[22] Filed: Apr. 6, 1995

Related U.S. Application Data

[62] Division of Ser. No. 131,361, Oct. 4, 1993, Pat. No. 5,443,950, which is a division of Ser. No. 575,518, Aug. 30, 1990, Pat. No. 5,266,480, which is a division of Ser. No. 402,104, Sep. 1, 1989, Pat. No. 5,032,508, which is a continuation-in-part of Ser. No. 242,096, Sep. 8, 1988, Pat. No. 4,963,489, which is a continuation-in-part of Ser. No. 38,110, Apr. 14, 1987, abandoned, which is a continuation-in-part of Ser. No. 36,154, Apr. 3, 1987, Pat. No. 4,721,096, which is a continuation of Ser. No. 853,569, Apr. 18, 1986, abandoned.

[51] Int. Cl.$^6$ ........................................... C12N 5/00
[52] U.S. Cl. ........................ 435/240.243; 424/529; 424/530; 424/534; 424/572; 435/1.1; 435/29; 435/32; 435/240.2; 435/240.21; 435/240.23
[58] Field of Search ............................ 424/95, 177, 572, 424/529, 530, 572, 534; 435/240.2, 240.21, 240.23, 240.243, 29, 32, 1, 240.1

[56] References Cited

U.S. PATENT DOCUMENTS

| | | |
|---|---|---|
| 3,997,396 | 12/1976 | Delente . |
| 4,016,036 | 4/1977 | Green et al. . |
| 4,024,020 | 5/1977 | Weiss et al. . |
| 4,087,327 | 5/1978 | Feder et al. . |
| 4,107,937 | 8/1978 | Chmiel . |
| 4,117,881 | 10/1978 | Williams et al. . |
| 4,135,975 | 1/1979 | Lichtman et al. . |
| 4,144,126 | 3/1979 | Burbridge . |
| 4,228,243 | 10/1980 | Iizuka . |
| 4,280,954 | 7/1981 | Yannas . |
| 4,299,819 | 11/1981 | Eisinger . |
| 4,342,828 | 8/1982 | Takaku et al. . |
| 4,458,678 | 7/1984 | Yannas et al. . |
| 4,481,946 | 11/1984 | Altshuler et al. . |
| 4,485,096 | 11/1984 | Bell ........................................... 424/95 |
| 4,485,097 | 11/1984 | Bell . |
| 4,486,188 | 12/1984 | Altshuler et al. . |
| 4,489,710 | 12/1984 | Spitler . |
| 4,520,821 | 6/1985 | Schmidt et al. . |
| 4,539,716 | 9/1985 | Bell . |
| 4,546,500 | 10/1985 | Bell . |
| 4,553,272 | 11/1985 | Mears . |
| 4,604,346 | 8/1986 | Bell . |
| 4,621,100 | 11/1986 | Lund et al. . |
| 4,642,292 | 2/1987 | Reid et al. . |
| 4,645,669 | 2/1987 | Reid . |
| 4,703,108 | 10/1987 | Silver . |
| 4,835,102 | 5/1989 | Bell . |

FOREIGN PATENT DOCUMENTS

| | | |
|---|---|---|
| 0075904 | 9/1981 | European Pat. Off. . |
| 85109336 | 1/1986 | European Pat. Off. . |
| 85303844 | 12/1986 | European Pat. Off. . |
| 86306544 | 3/1987 | European Pat. Off. . |
| 0081781 | 5/1983 | Japan . |
| 69-123884 | 12/1985 | Japan . |
| 8304177 | 12/1983 | WIPO . |
| 8803785 | 6/1988 | WIPO . |

OTHER PUBLICATIONS

Sarber, et al., 1981, Mechanisms of Aging and Development, 17:107–117.
Nasgens et al., 1984, Collagen Rel. Res. 4:351–364.
Freshney, "Culture Of Animal Cells, A Manual Of Basic Technique" 1983, Alan R. Liss, Inc. N.Y.
Lydersen, "Layer Scale Cell Culture Technology" 1987, Hansen Publishers, Munich, Vernon, New York.
Thilly, "Mammalian Cell Technology," 1986, Butterworths, Boston, London, Durban, Singapore, Sydney, Toronto, Wellington.
Old Primrose, "Principles Of Gene Manipulation".
An Introduction to Genetic Engineering "Chapter" in Studies in Microbiology, vol. 2, Third Edition, 1985, Blackwell Scientific Publication.
Leighton, J., 1951, J.N.C.I. 12:545–561.
Schneider, H. et al., 1963, Exp. Cell Res. 30:449–459.
Kruse, P. et al., 1965, J.Cell Biol. 27:273–279.
Leighton, J. et al., 1967, Science 155:1259–1261.
Leighton, J. et al., 1968, Cancer Res. 28:286–296.
Elsdale et al., 1972, J. Cell Biol. 54:626–637.
Ansevin, K. et al., 1973, In Vitro 8:483–488.
Sobour, O. et al., 1975, J. Neurosurg 43:742–749.
Douglas, W. H. et al., 1976, In Vitro 12:373–381.
Ebendal, E., 1976, Exp. Cell Res. 98:159–169.
Emerman, J., et al., 1977, Proc. Natl. Acad. Sci, U.S.A. 74:4466–4470.
Bell, E., et al., 1979, PNAS 76:1274–1278.
Lindsay, R., 1979, Nature 282:80–82.
Reid, L. et al., 1979, 58:263–278.
Yang, J. et al., 1979, Proc. Natl. Acad. Sci. U.S.A. 76:3401–3405.
Douglas, W. et al., 1980, In Vitro 16:306–312.

(List continued on next page.)

Primary Examiner—Leslie Wong
Attorney, Agent, or Firm—Pennie & Edmonds

[57] ABSTRACT

The present invention relates to a three-dimensional cell culture system which can be used to culture a variety of different cells and tissues in vitro for prolonged periods of time. In accordance with the invention, cells derived from a desired tissue are inoculated and grown on a pre-established stromal support matrix. The stromal support matrix comprises stromal cells, such as fibroblasts actively growing on a three-dimensional matrix. Stromal cells may also include other cells found in loose connective tissue such as endothelial cells, macrophages/monocytes, adipocytes, pericytes, reticular cells found in bone marrow stroma, etc. The stromal matrix provides the support, growth factors, and regulatory factors necessary to sustain long-term active proliferation of cells in culture. When grown in this three-dimensional system, the proliferating cells mature and segregate properly to form components of adult tissues analogous to counterparts found in vivo.

58 Claims, 25 Drawing Sheets

OTHER PUBLICATIONS

Folkman J. et al., Nature 288:551–555.
Vlodavsky, D. et al., 1980, Cell 19:607–616.
Yang, J. et al., 1980, PNAS 77:2088–2092.
Yang, J. et al., 1981, Cancer Res 41:1021–1027.
Thuroff, et al., 1983, Urology 21:155–158.
Daniels, E. and Moore, 1969, Anat. Rec. 163:174.
Daniels, E., 1975, Anat. Rec. 181:341.
Dexter, T. M. et al., 1976, in "Methods in Cell Biology," editor D. M. Prescott, pp. 387–405, Academic Press, N.Y.
Dexter, T. M. et al., 1976, J. Cell. Physiol. 91:335–344.
Blackburn, M. et al., 1977, Br. J. Haematology 37:337.
Dexter, T. M., 1979, Acta Haemat. 62:299–305.
Daniels, E., 1978, Anat. Rec. 190:376.
Moore, M. A. S. et al., 1979, Blood Cells 5:297–311.
Reimann, J. et al., 1979, Exp. Hematol 7:52–58.
Daniels, E., 1980, Exp. Hematol. 8:157–165.
Gartner, S. et al., 1980, Proc. Natl. Acad. Sci. 77:4756–4759.
Hocking, W. G. et al., 1980, in "Biology of Bone Marrow Transplantation", edited by R. B. Gale, et al., pp. 431–442, Academic Press, N.Y.
Daniels, 1981, Exp. Hematol. 9:697–710.
Daniels, E., 1981, Anat. Rec. 199:63A.
Coulombel et al., 1983, Blood 62:291–297.
Daniels, E., 1983, RES; Journal of Recticuloendothelial Society 33:457–465.
Dexter, T. et al., 1984, in "Long–Term Bone Marrow" editor Wright et al., pp. 57–96, Alan R. Liss, Inc., N.Y.
Greenberger, J. S., 1984, in "Long–Term Bone Marrow Culture", editor D. Wright, pp. 119–131, Alan R. Liss, N.Y.
Phillips, R. A., 1984, in "Long–Term Bone Marrow Culture", editor D. Wright, pp. 309–321, Alan R. Liss, Inc. N.Y.
Chang, J., et al., 1986, The Lancet, pp. 294–295.
Brockbank, K. G. M., et al., 1986, Exp. Hematol. 14:386–394.
McMillen, et al., 1986, J. Surg. Res. 40:193–197.
Naughton et al., 1986, Blood 68:149a.
Page et al., 1986, Exp. Hematol. 14:719–723.
Yuen et al., 1986, Exp. Hematol. 14:771–775.
Hunt et al., 1987, Cell, 48:996–1007.
Rennick et al., 1987, Blood 69:682–691.
Whitlock et al., 1987, Cell, 48:1009–1021.
E. Daniels, 1977, Anat. REc. 187:562.
Gorin, N. C. et al., 1978, Blood 51:2157–265.
Ritz et al, 1982, The Lancet, Jul. 10, 1982, pp. 60–63.
Van De Ouweland, F. et al., 1982, Cryobiology 19:292–298.
Parkman, 1986, Science 232:1373–1378.
Green et al., 1978, Science 200:1385–1388.
Bell, E. et al., 1979, Proc. Natl. Acad. Sci. U.S.A. 76:1274–1278.
Green, H. et al., 1979, Proc. Natl. Acad. Sci. U.S.A. 76:5665–5668.
Yannas, I. et al., 1980, J. Biomedical Res. 14:107–131.
Bell, E. et al., 1981, Science 211:1052–1054.
Yannas et al., 1982, Science 215:174–176.
Bell, E. et al., 1983, J. Invest. Dermatol. 81:$2_s$–$10_s$.
Kao, J. et al., 1983, Toxicol. and Appl. Pharmacol. 68:206–217 (1983).
Gallico et al., 1984, N. Engl. J. Med. 311:448–451.
Pittelkow et al., 1986, Mayo Clin. Proc. 61:771–777.
Boyce, J., et al., 1988, Surgery 421–431.
Michalopoulos, G. and Pitot, H., 1975, Fed. Proc. 34:826.
Michalopoulos, G., Sattler, G., O'Connor, L., and Savage, R. and Bonney, R., 1978, Exp. Cell Res. 114:307–315.
Sirica, A., Ricahards, W., Tsukada, Y., Sattler, C., and Pitot, H., 1979, Proc. Natl. Acad. Sci., U.S.A. 76:283–287.
Sirica, A., Hwang, C., Sattler, G. and Pitot, H., 1980, Cancer Res. 40:3259–3267.
Latsinik et al., 1981, Biol. Abstr. 74:3841.
Gordon et al., 1983, Int. J. Cell Cloning 1:429–39.
Chailakhyan et al., 1984, Biol. Abstr. vol. 80, abstract 28317.

THREE-DIMENSIONAL TUMOR CELL AND TISSUE CULTURE SYSTEM

This is division of application Ser. No. 08/131,361, filed Oct. 4, 1993, U.S. Pat. No. 5,443,950; which is a division of Ser. No. 07/575,518, filed Aug. 30, 1990, U.S. Pat. No. 5,266,480; which is a division of Ser. No. 07/402,104, filed Sep. 1, 1989, U.S. Pat. No. 5,032,508; which is a continuation-in-part of Ser. No. 07/242,096, filed Sep. 8, 1988, U.S. Pat. No. 4,963,489; which is a continuation-in-part of Ser. No. 07/038,110, filed Apr. 14, 1987, abandoned; which is a continuation-in-part of Ser. No. 07/036,154, filed Apr. 3, 1987, U.S. Pat. No. 4,721,096 which is a continuation of Ser. No. 06/853,569, filed Apr. 18, 1986, abandoned; each of which is incorporated by reference herein in its entirety.

1. INTRODUCTION

The present invention is directed to a three-dimensional cell and tissue culture system. This culture system can be used for the long term proliferation of cells and tissues in vitro in an environment that more closely approximates that found in vivo. The culture system described herein provides for proliferation and appropriate cell maturation to form structures analogous to tissue counterparts in vivo.

The resulting cultures have a variety of applications ranging from transplantation or implantation in vivo, to screening cytotoxic compounds and pharmaceutical compounds in vitro, and to the production of biologically active molecules in "bioreactors". The invention is demonstrated by way of examples describing the three-dimensional culture of bone marrow, skin, liver, muscosal epithelium, pancreas, and adenocarcinoma, and further examples which show the use of three-dimensional culture systems in cytotoxicity assays, a blood-brain barrier model system and skin transplants.

2. BACKGROUND OF THE INVENTION

The majority of vertebrate cell cultures in vitro are grown as monolayers on an artificial substrate bathed in nutrient medium. The nature of the substrate on which the monolayers grow may be solid, such as plastic, or semisolid gels, such as collagen or agar. Disposable plastics have become the preferred substrate used in modern-day tissue or cell culture.

A few researchers have explored the use of natural substrates related to basement membrane components. Basement membranes comprise a mixture of glycoproteins and proteoglycans that surround most cells in vivo. For example, Reid and Rojkund (1979, In, Methods in Enzymology, Vol. 57, Cell Culture, Jakoby & Pasten, eds., New York, Acad. Press, pp. 263–278); Vlodavsky et al., (1980, Cell 19:607–617); Yang et al., (1979, Proc. Natl. Acad. Sci. USA 76:3401) have used collagen for culturing heptocytes, epithelial cells and endothelial tissue. Growth of cells on floating collagen (Michalopoulos and Pitot, 1975, Fed. Proc. 34:826) and cellulose nitrate membranes (Savage and Bonney, 1978, Exp. Cell Res. 114:307–315) have been used in attempts to promote terminal differentiation. However, prolonged cellular regeneration and the culture of such tissues in such systems has not heretofore been achieved.

Cultures of mouse embryo fibroblasts have been used to enhance growth of cells, particularly at low densities. This effect is thought to be due partly to supplementation of the medium but may also be due to conditioning of the substrate by cell products. In these systems, feeder layers of fibroblasts are grown as confluent monolayers which make the surface suitable for attachment of other cells. For example, the growth of glioma on confluent feeder layers of normal fetal intestine has been reported (Lindsay, 1979, Nature 228:80).

While the growth of cells in two dimensions is a convenient method for preparing, observing and studying cells in culture, allowing a high rate of cell proliferation, it lacks the cell—cell and cell-matrix interactions characteristic of whole tissue in vivo. In Border to study such functional and morphological interactions, a few investigators have explored the use of three-dimensional substrates such as collagen gel (Douglas et al., 1980, In Vitro 16:306–312; Yang et al., 1979, Proc. Natl. Acad. Sci. 76:3401; Yang et al., 1980, Proc. Natl. Acad. Sci. 77:2088–2092; Yang et al., 1981, Cancer Res. 41:1021–1027); cellulose sponge, alone (Leighton et al., 1951, J. Natl. Cancer Inst. 12:545–561) or collagen coated (Leighton et al., 1968, Cancer Res. 28:286–296); a gelatin sponge, Gelfoam (Sorour et al., 1975, J. Neurosurg. 43:742–749).

In general, these three-dimensional substrates are inoculated with the cells to be cultured. Many of the cell types have been reported to penetrate the matrix and establish a "tissue-like" histology. For example, three dimensional collagen gels have been utilized to culture breast epithelium (Yang et al., 1981, Cancer Res. 41:1021–1027) and sympathetic neurons (Ebendal, 1976, Exp. Cell Res. 98:159–169). Additionally, various attempts have been made to regenerate tissue-like architecture from dispersed monolayer cultures. Kruse and Miedema (1965, J. Cell Biol. 27:273) reported that perfused monolayers could grow to more than ten cells deep and organoid structures can develop in multilayered cultures if kept supplied with appropriate medium (see also Schneider et al., 1963, Exp. Cell Res. 30:449–459 and Bell et al., 1979, Proc. Natl. Acad. Sci. USA 76:1274–1279); Green (1978, Science 200:1385–1388) has reported that human epidermal kerotinocytes may form dematoglyphs (friction ridges) if kept for several weeks without transfer; Folkman and Haudenschild (1980, Nature 288:551–556) reported the formation of capillary tubules in cultures of vascular endothelial cells cultured in the presence of endothelial growth factor and medium conditioned by tumor cells; and Sirica et al. (1979, Proc. Natl. Acad. Sci. U.S.A. 76:283–287; 1980, Cancer Res. 40:3259–3267) maintained hepatocytes in primary culture for about 10–13 days on nylon meshes coated with a thin layer of collagen. However, the long term culture and proliferation of cells in such systems has not been achieved.

Indeed, the establishment of long term culture of tissues such as bone marrow has been attempted. Overall the results were disappointing, in that although a stromal cell layer containing different cell types is rapidly formed, significant hematopoiesis could not be maintained for any real time. (For review see Dexter et al., In Long Term Bone Marrow Culture, 1984, Alan R. Liss, Inc., pp.57–96).

3. SUMMARY OF THE INVENTION

The present invention relates to a three-dimensional cell culture system which can be used to culture a variety of different cells and tissues in vitro for prolonged periods of time. In accordance with the invention, cells derived from a desired tissue are inoculated and grown on a pre-established stromal support matrix. The stromal support matrix comprises stromal cells, such as fibroblasts, actively growing on a three-dimensional matrix. Stromal cells may also include other cells found in loose connective tissue such as endothelial cells, macrophages/monocytes, adipocytes, pericytes, reticular cells found in bone marrow stroma, etc. The stromal matrix provides the support, growth factors, and regulatory factors necessary to sustain long-term active proliferation of cells in culture. When grown in this three-dimensional system, the proliferating cells mature and segregate properly to form components of adult tissues analogous to counterparts found in vivo.

The invention is based, in part, on the discovery that growth of stromal cells in three dimensions will sustain active proliferation of cells in culture for longer periods of time than will monolayer systems. This may be due, in part, to the increased surface area of the three-dimensional matrix which results in a prolonged period of active proliferation of stromal cells. These proliferating stromal cells elaborate proteins, growth factors and regulatory factors necessary to support the long term proliferation of both stromal and tissue-specific cells inoculated onto the stromal matrix. In addition, the three-dimensionality of the matrix allows for a spatial distribution which more closely approximates conditions in vivo, thus allowing for the formation of microenvironments conducive to cellular maturation and migration. The growth of cells in the presence of this support may be further enhanced by adding proteins, glycoproteins, glycosaminoglycans, a cellular matrix, and other materials to the support itself or by coating the support with these materials.

The use of a three-dimensional support allows the cells to grow in multiple layers, thus creating the three-dimensional cell culture system of the present invention. Many cell types and tissues can be grown in the three-dimensional culture system.

In specific embodiments of the invention, bone marrow, skin, liver, pancreas, mucosal epithelium, adenocarcinoma and melanoma tissues may be grown in the three dimensional culture system.

In addition, the resulting cultures may be used as model systems for the study of physiologic or pathologic conditions. For example, in a specific embodiment of the invention, a three-dimensinal culture system may be used as a model for the blood-brain barrier. In an additional specific embodiment, and not by way of limitation, a three-dimensional culture of mucosal epithelium may be used as a model system to study herpesvirus or papillomavirus infection. The resulting cultures have a variety of applications ranging from transplantation or implantation, in vivo, of cells grown in the cultures, cytotoxicity testing and screening compounds in vitro, and the design of "bioreactors" for the production of biological materials in vitro.

3.1. Definitions and Abbreviations

The following terms used herein shall have the meanings indicated:

Adherent Layer: cells attached directly to the three-dimensional matrix or connected indirectly by attachment to cells that are themselves attached directly to the matrix.

Stromal Cells: fibroblasts with or without other cells and/or elements found in loose connective tissue, including but not limited to, endothelial cells, pericytes, macrophages, monocytes, plasma cells, mast cells, adipocytes, etc.

Tissue-Specific or Parenchymal Cells: the cells which form the essential and distinctive tissue of an organ as distinguished from its supportive framework.

Three-Dimensional Matrix: a three dimensional matrix composed of any material and/or shape that (a) allows cells to attach to it (or can be modified to allow cells to attach to it); and (b) allows cells to grow in more than one layer. This support is inoculated with stromal cells to form the three-dimensional stromal matrix.

Three-Dimensional Stromal Matrix: a three dimensional matrix which has been inoculated with stromal cells. Whether confluent or subconfluent, stromal cells according to the invention continue to grow and divide. The stromal matrix will support the growth of tissue-specific cells later inoculated to form the three dimensional cell culture.

Three-Dimensional Cell Culture: a three dimensional stromal matrix which has been inoculated with tissue-specific cells and cultured. In general, the tissue specific cells used to inoculate the three-dimensional stromal matrix should include the "stem" cells (or "reserve" cells) for that tissue; i.e., those cells which generate new cells that will mature into the specialized cells that form the parenchyma of the tissue.

The following abbreviations shall have the meanings indicated:

BFU-E=burst-forming unit-erythroid
CFU-C=colony forming unit-culture
CFU-GEMM=colony forming unit-granuloid, erythroid, monocyte, megakaryocyte
EDTA=ethylene diamine tetraacetic acid
FBS=fetal bovine serum
HBSS=Hank's balanced salt solution
HS=horse serum
LTBMC=long term bone marrow culture
MEM: minimal essential medium
PBL=peripheral blood leukocytes
PBS=phosphate buffered saline
RPMI 1640=Roswell Park Memorial Institute medium number 1640 (GIBCO, Inc., Grand Island, N.Y.)
SEM=scanning electron microscopy

4. DESCRIPTION OF THE FIGURES

Figure 3:
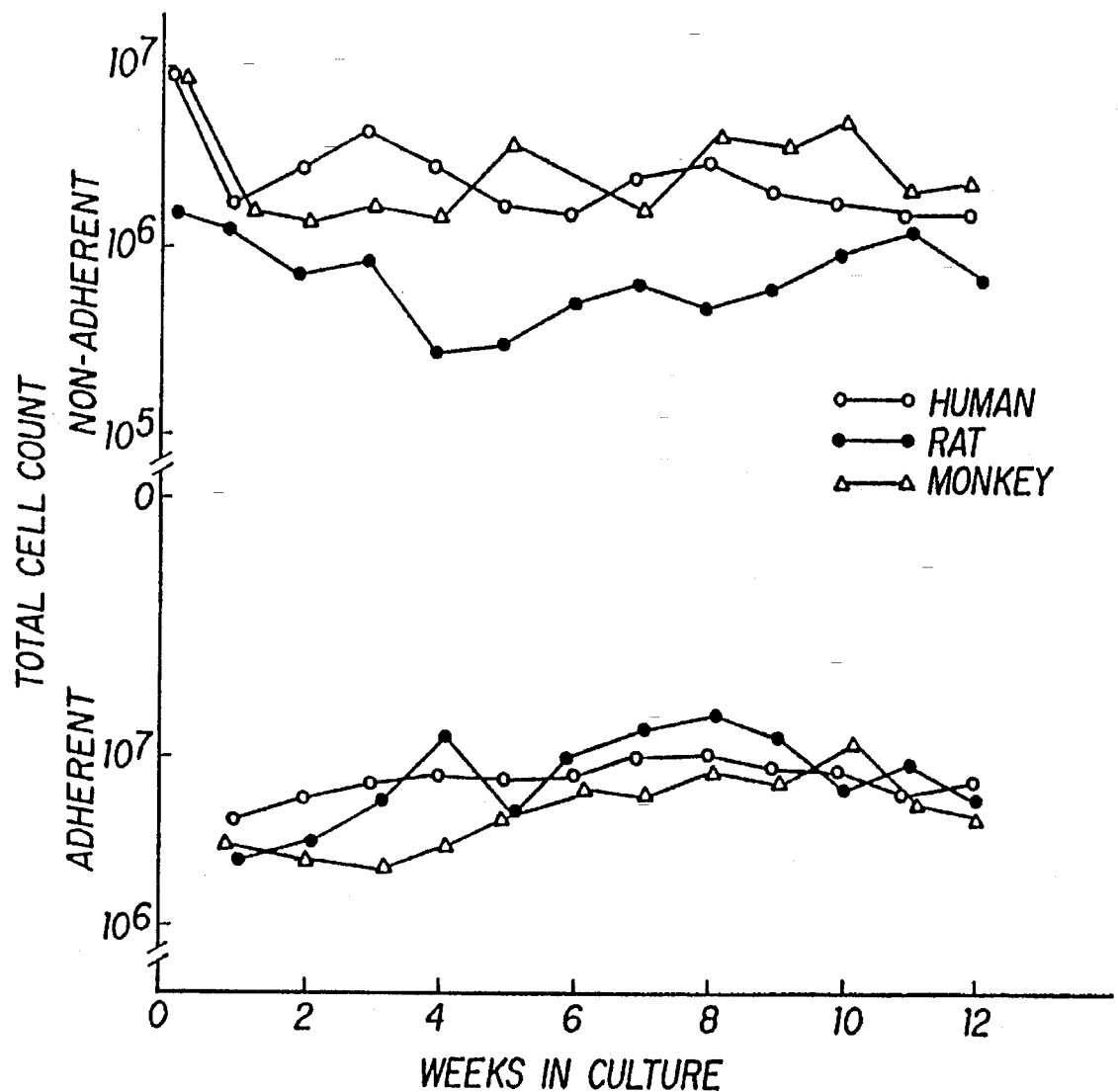

FIG. 3 is a graph representing the total cell count of the three-dimensional LTBMC adherent and nonadherent layers over several weeks in culture. Total cell counts and cytospin preparations of the nonadherent zone were made using spent medium removed when the cultures were fed every five days. Cell counts of the adherent zone were done at different intervals of LTBMC by treating the three-dimensional cell culture with collagenase and trypsin to remove adherent cells. Cellular proliferation achieved a steady state condition after several weeks in culture.

Figure 4:
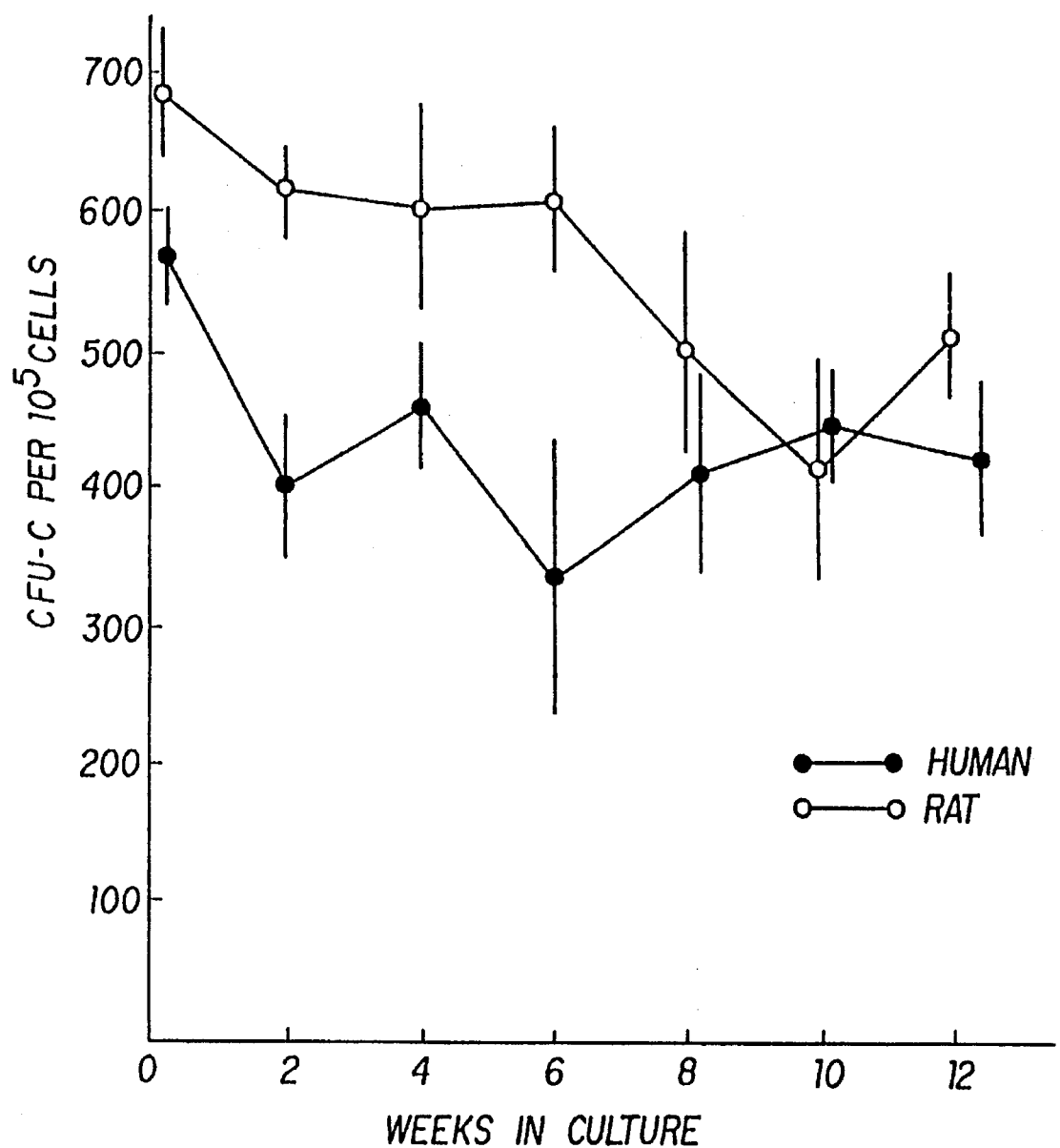

FIG. 4 is a graph representing the CFU-C per $10^5$ cells obtained from the adherent zone of the three-dimensional LTBMC over several weeks in culture.

Figure 5:
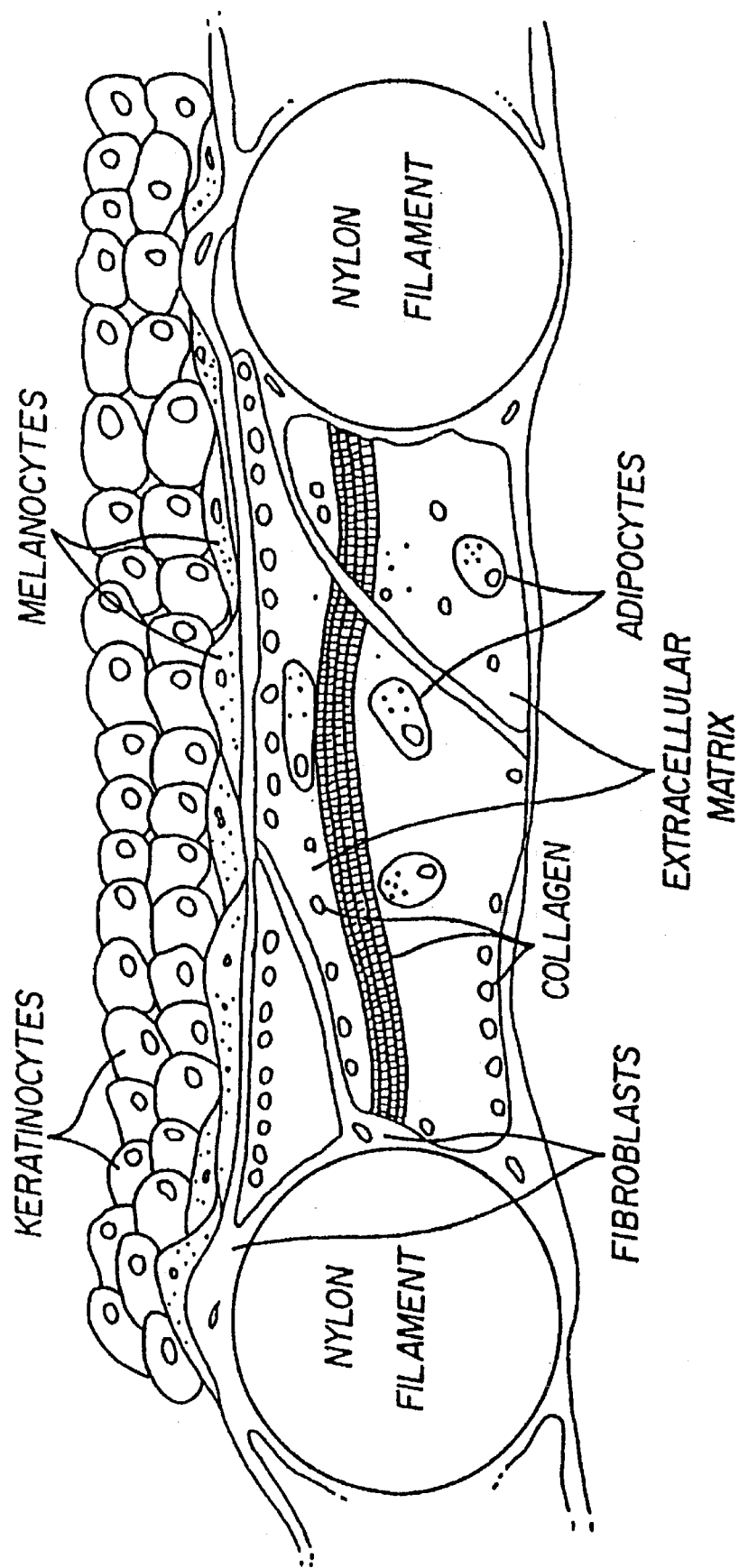

FIG. 5 is a diagrammatic representation of the three-dimensional skin model. A dermal/epidermal junction is present, above which lies pigmented melanocytes and several layers of pigment-containing keratinocytes. The stromal cells attach to the matrix and form the dermal component.

Figure 6:

FIG. 6 is a scanning electron micrograph of the three-dimensional stroma three days after inoculation with melanocytes. Melanocytes grow normally in the three-dimensional system in that they exhibit dendrite formation, remain pigmented, and retain the ability to transfer pigment to keratinocytes.

Figure 7:
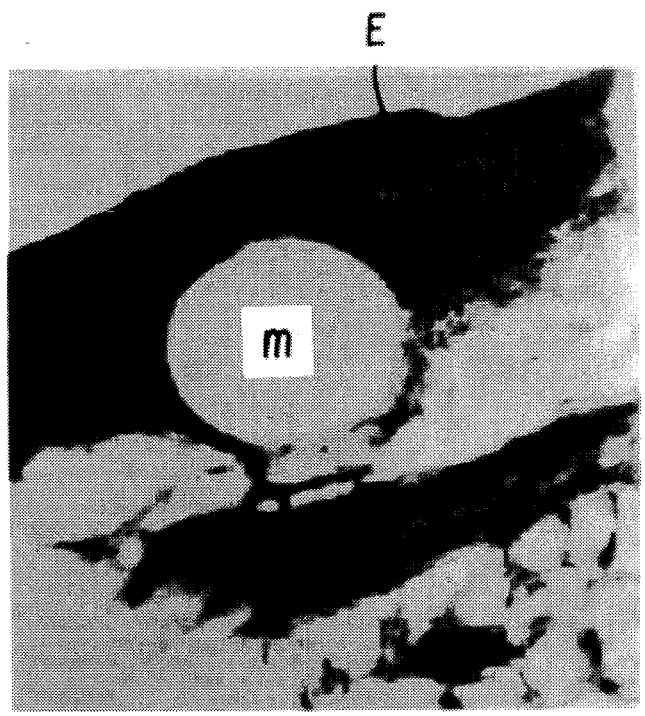

FIG. 7 is a photomicrograph of a cross section of the three-dimensional skin culture stained with hematoxylin-eosin. Normal epidermal (E) cell morphology and orientation is obvious. Epidermal and dermal (D) components completely surround the mesh fiber (M), and a distinct dermal/epidermal junction is present.

Figure 8:
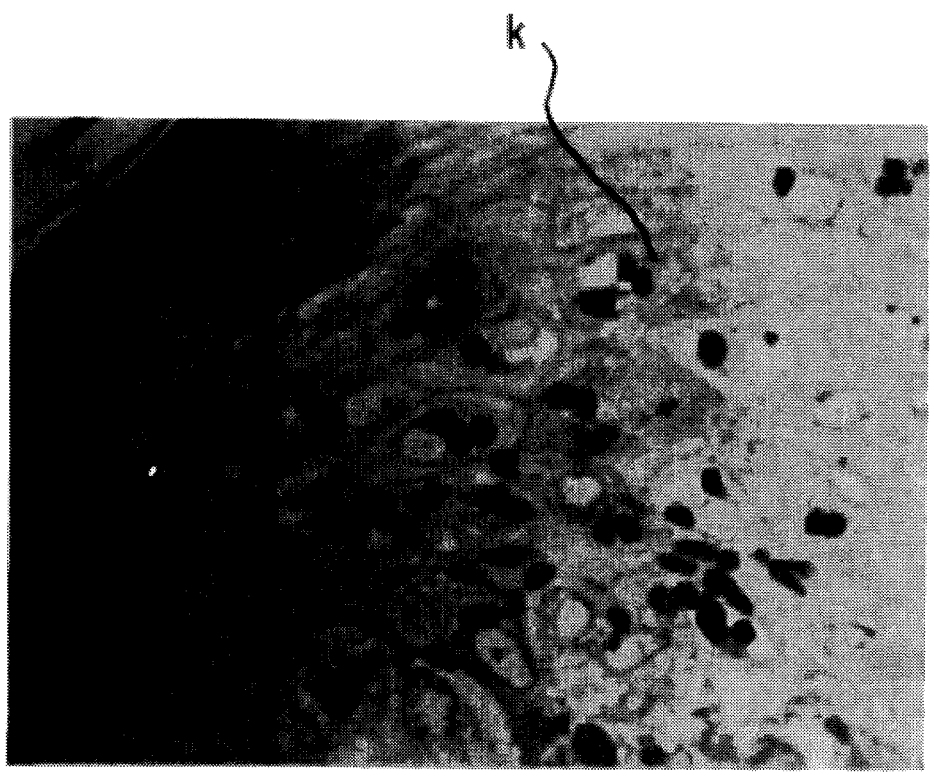

FIG. 8 is a photomicrograph showing an area of epidermis from the three-dimensional skin culture stained with toluidine. Keratinocytes (K) manifest a normal morphology and contain pigment (P) granules. A maturation of cells is seen, with evidence of stratum corenum (SC).

Figure 9:
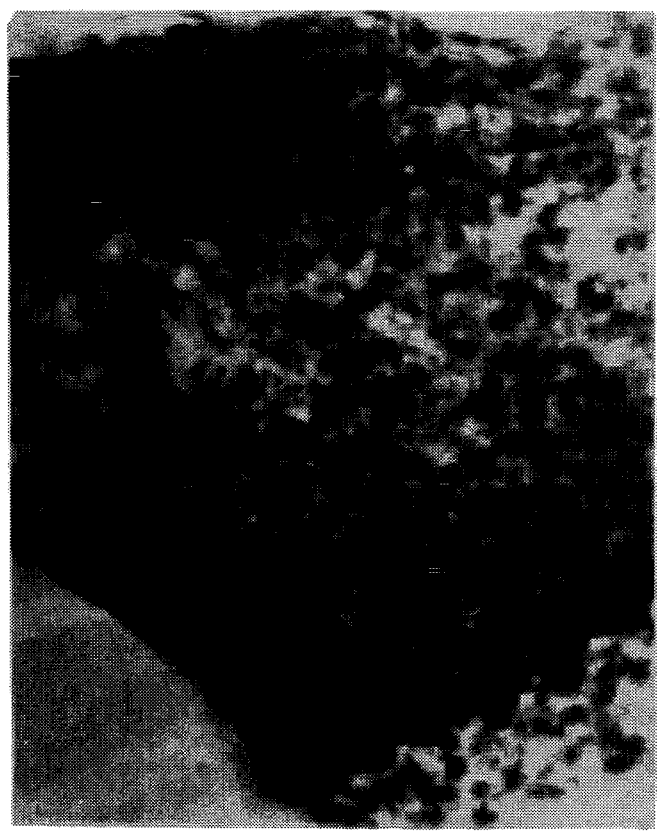

FIG. 9 is a photomicrograph of the three-dimensional skin model grafted onto rats seven days post transplant. A distinct dermal and epidermal junction is evident. Cells show firm attachment to the mesh with no signs of rejection.

Figure 10:
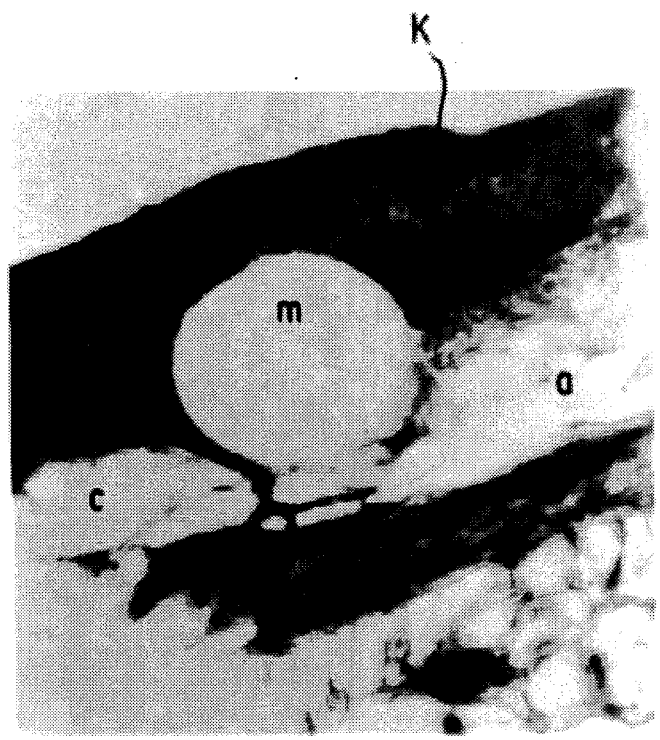

FIG. 10 is a photomicrograph of the three-dimensional skin model grafted onto rats seven days post transplant. Collagen bundles (c) and all cell types are represented, including keratinocytes (k), fibroblasts (f), adipocytes (a), and smooth muscle cells (s), arranged in a natural configuration around the nylon mesh fiber (m).

Figure 11:

FIG. 11. is a photomicrograph of adult liver cultures grown by the three-dimensional culture method forming a three-dimensional multilayered tissue on hepatic stromal cells.

Figure 12:
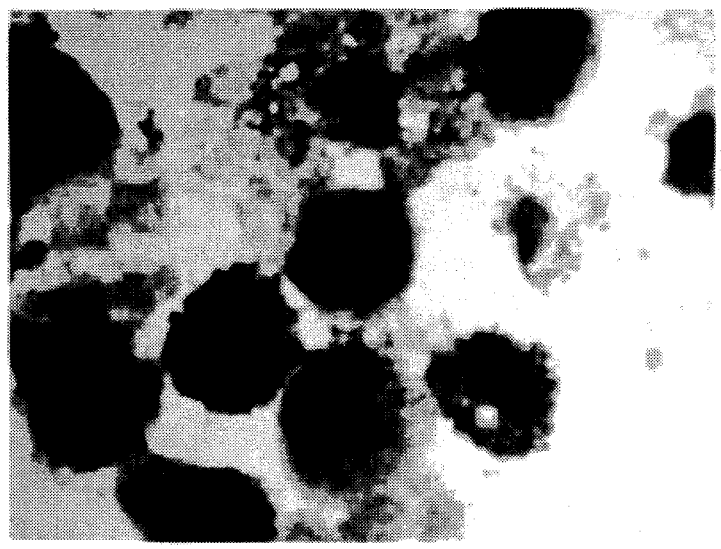

FIG. 12. is a photomicrograph of actively dividing hepatocytes during the first ten to twelve days after inoculation into three-dimensional cultures resemble hepatoblasts or cells of regenerating liver.

Figure 13:
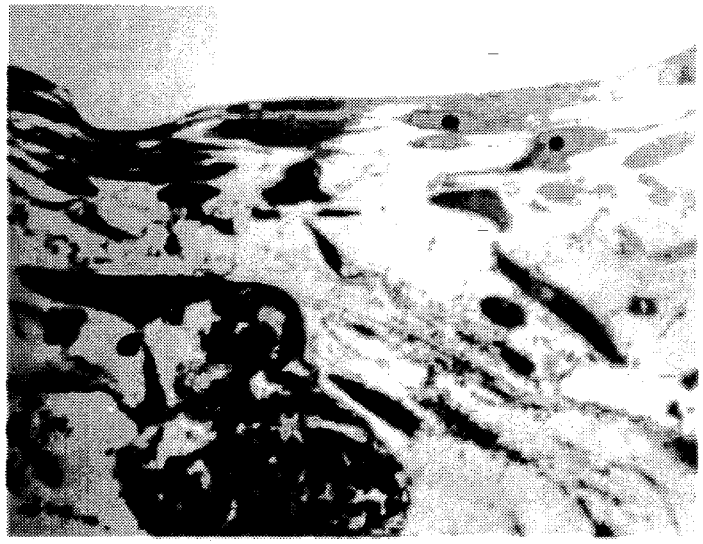

FIG. 13. is a photomicrograph of a cross-section of a three-dimensional tissue culture of mucosal epithelium.

Figure 14:
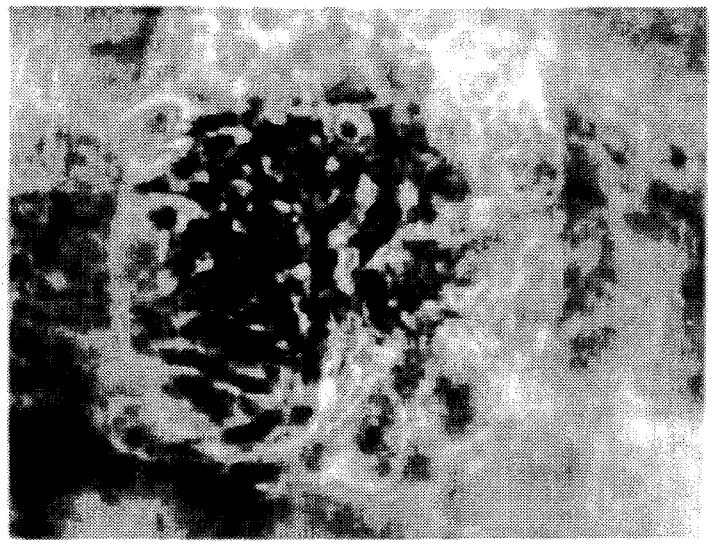

FIG. 14. is a photomicrograph of a cross-section of a three-dimensional tissue culture of pancreas. An arrow points to zymogen granules in an acinar cell. An asterisk indicates a stromal cell.

Figure 15:
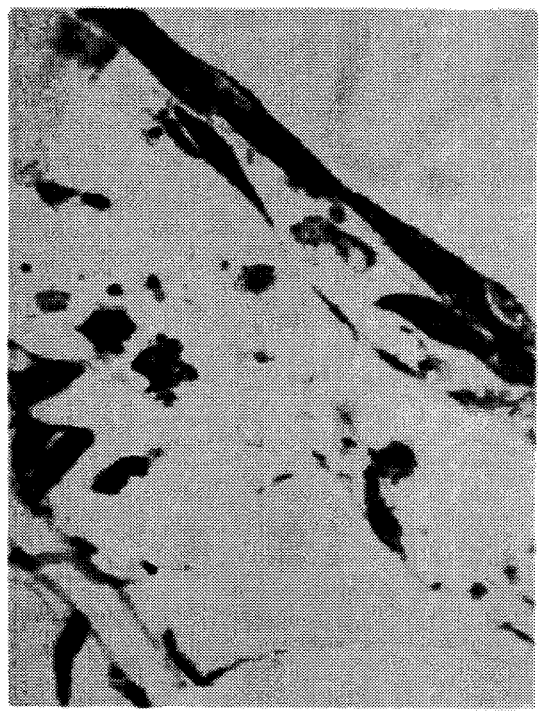

FIG. 15. is a photomicrograph of a cross-section of a three-dimensional tissue culture model system of the blood brain barrier. A closed arrow points to a small blood vessel endothelial cell. An open arrow points to a neuronal cell. An asterisk indicates an astrocyte.

Figure 16:
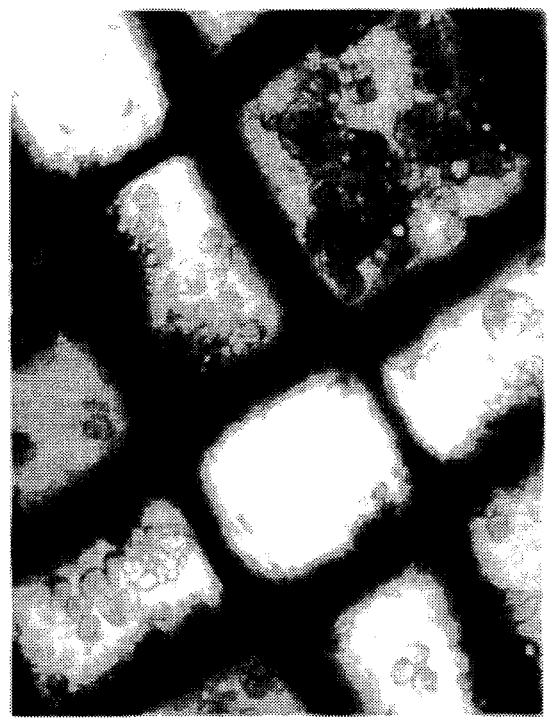

FIG. 16. is a photomicrograph of a cross-section of a three-dimensional tissue culture of adenocarcinoma.

Figure 17:
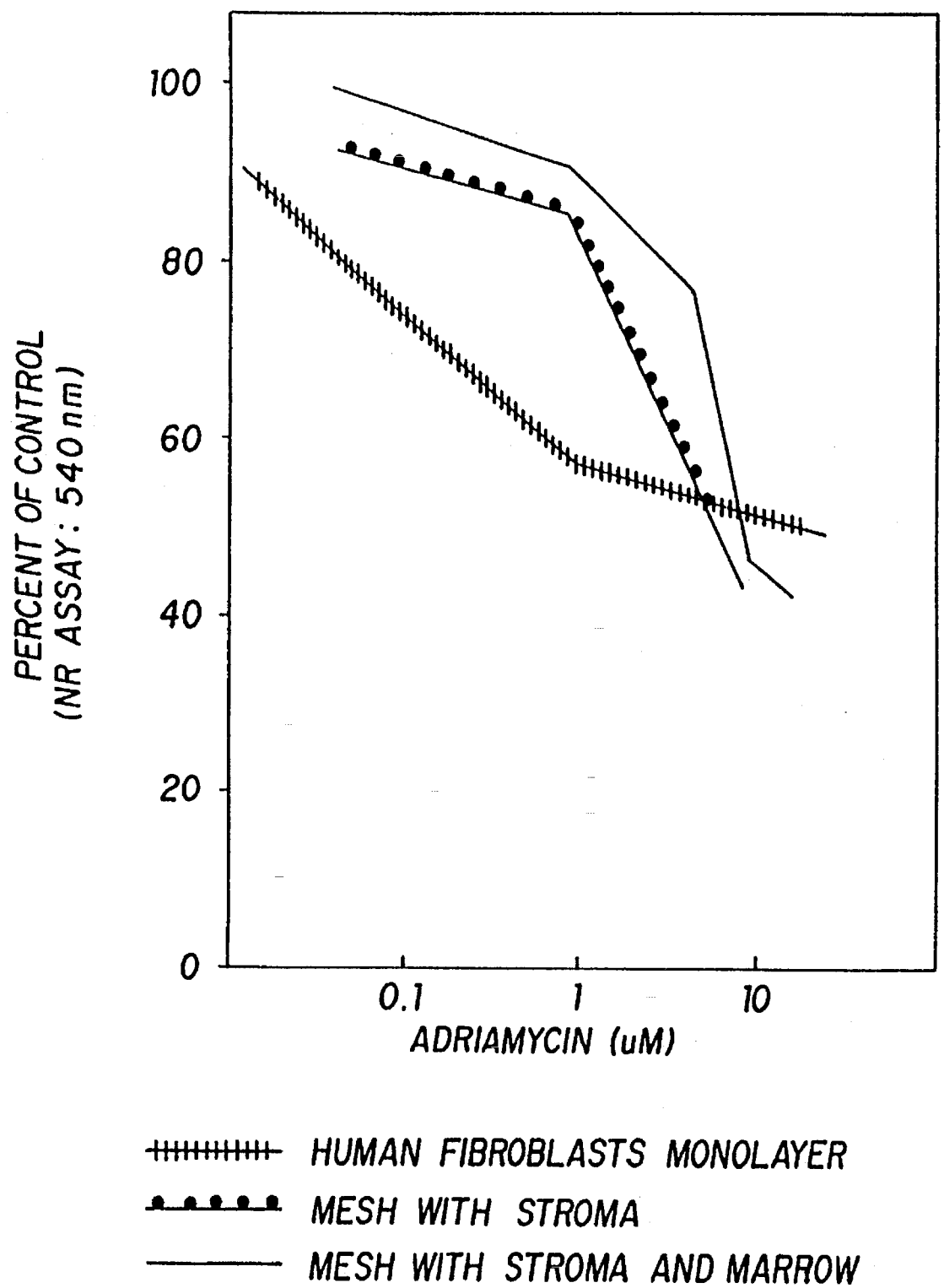

FIG. 17. is a graph comparing the response of fibroblasts grown in monolayer with stromal and full-thickness marrow grown on the three-dimensional mesh system of the invention. The substrates show a dose-related response to adriamycin utilizing the neutral-red assay for cell viability.

Figure 18:
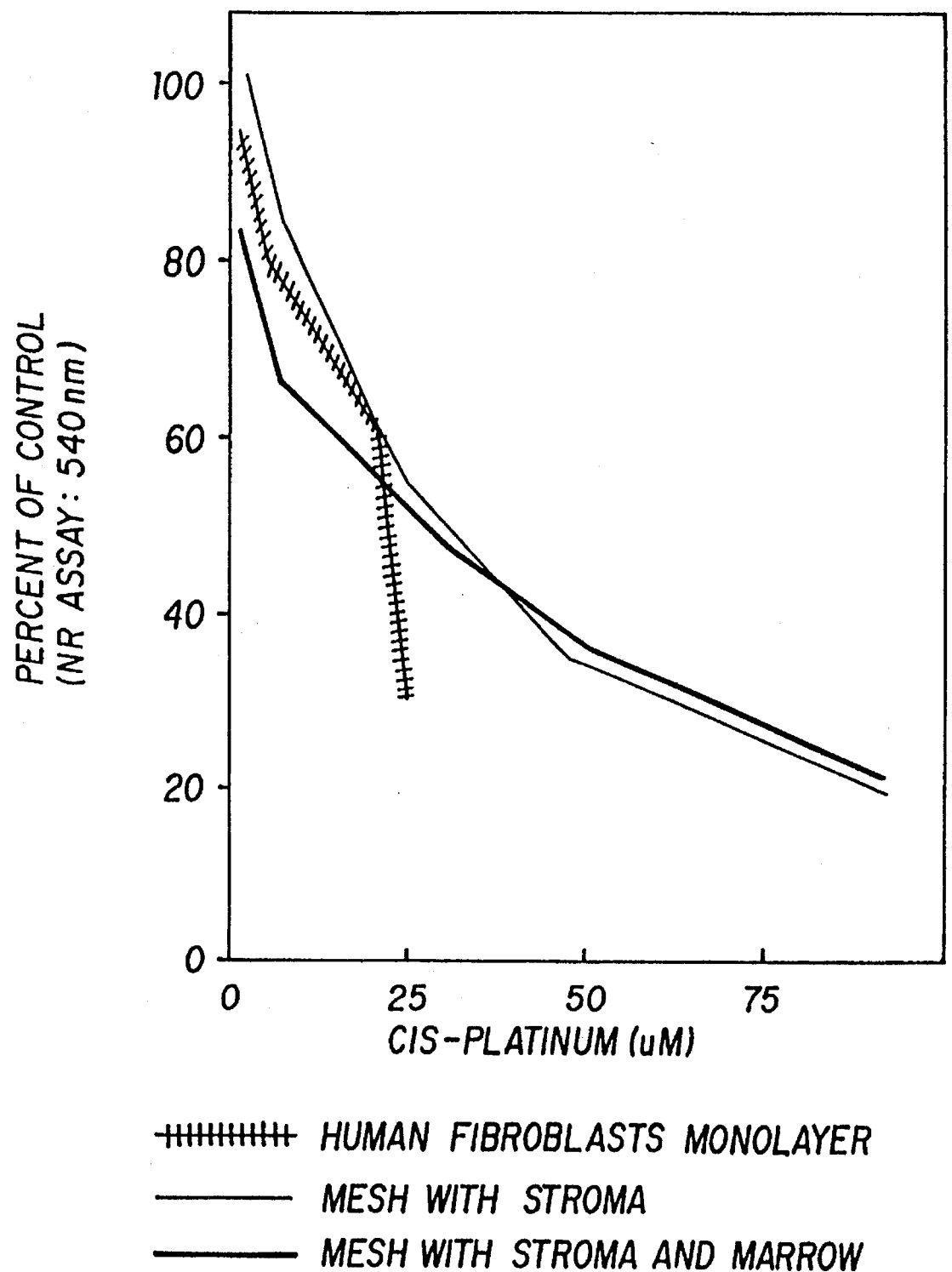

FIG. 18. is a graph presenting neutral red assay results showing a dose-related response to cis-platinum by stromal and bone marrow three-dimensional cultures.

Figure 19:
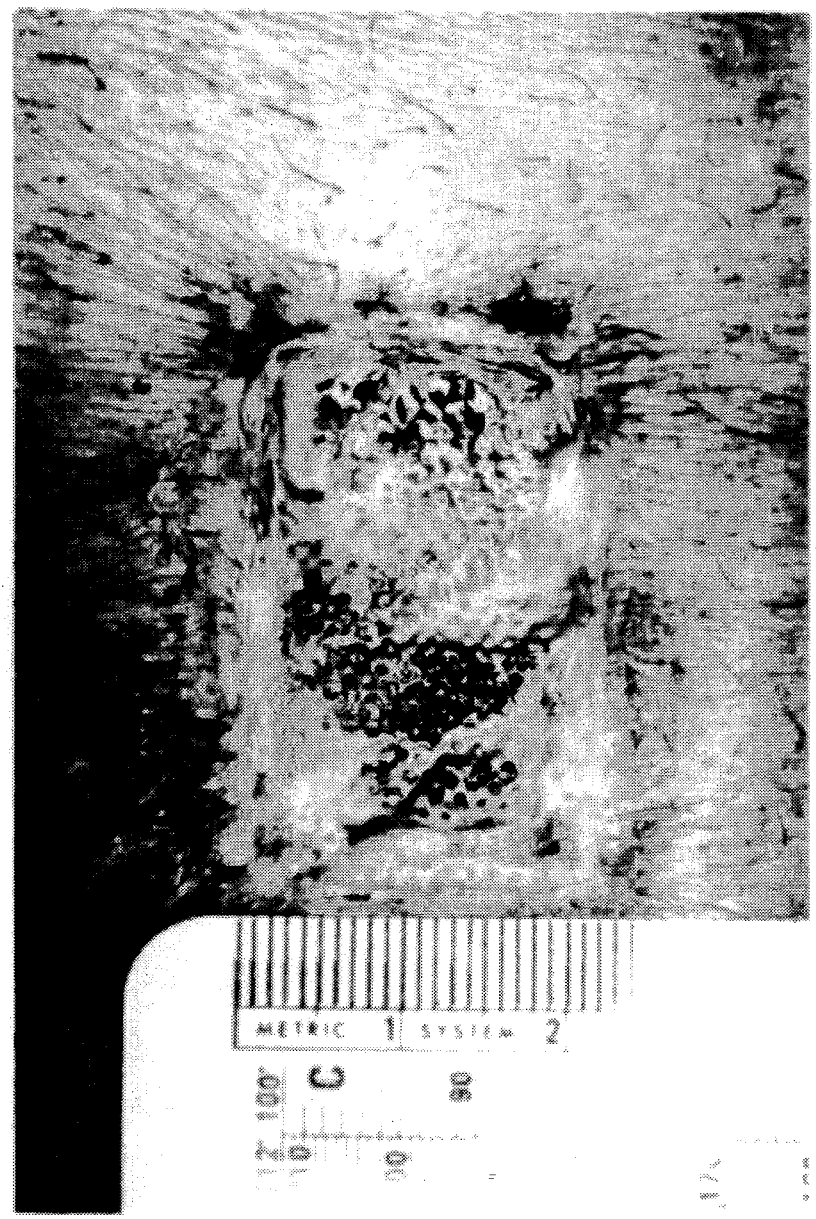

FIG. 19. is a photograph showing the surface condition of a full-thickness wound 10 days after implantation of a human neodermis into micropig. Minimal contraction was noted, with no signs of rejection or dehydration.

Figure 20:
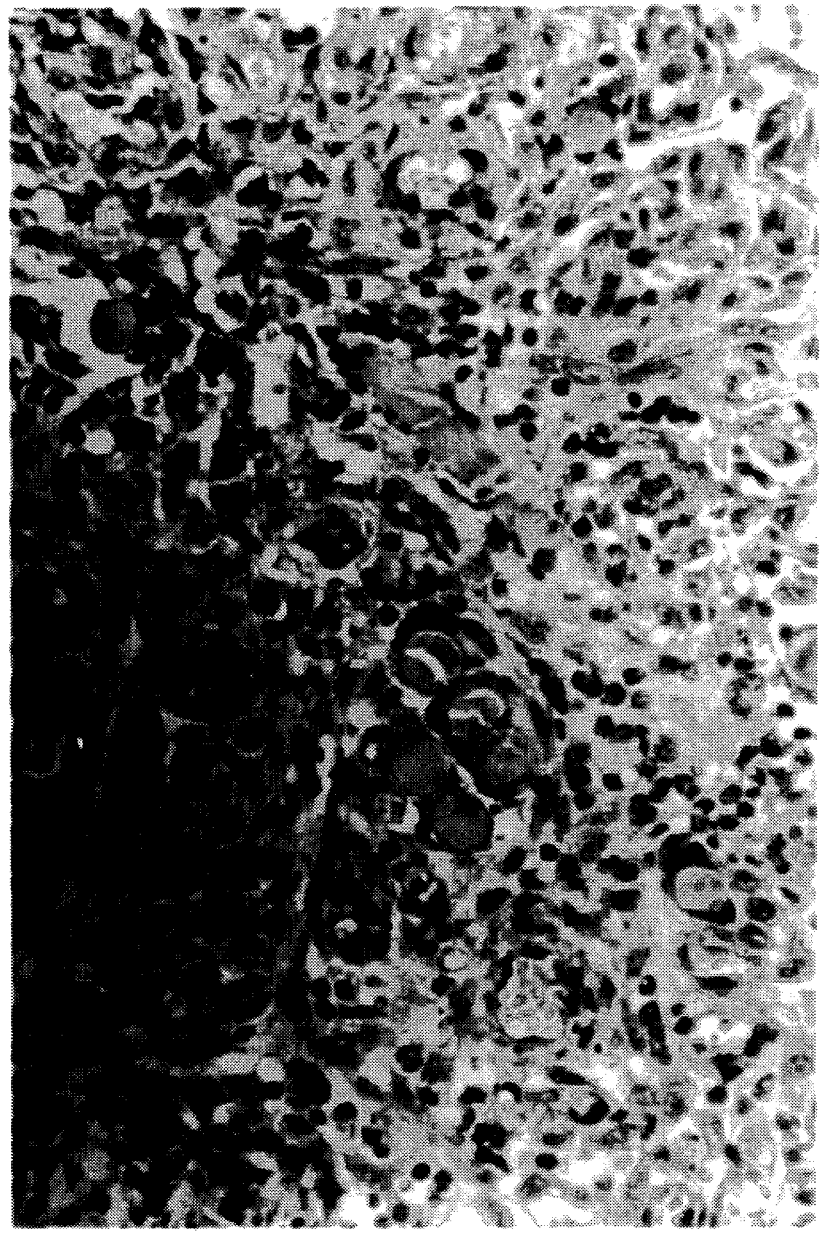

FIG. 20. is a photomicrograph presenting histological evaluation of a neodermis showing a cross-section of mesh fibers, along with active fibroblasts and naturally-secreted collagen.

Figure 21:

FIG. 21. is a photograph comparing wounds treated either with neodermis (left) and biodegradable mesh alone (right). Note the decrease in contraction and increase in pigmentation and hair growth in the wound into which the neodermis was implanted.

Figure 22:
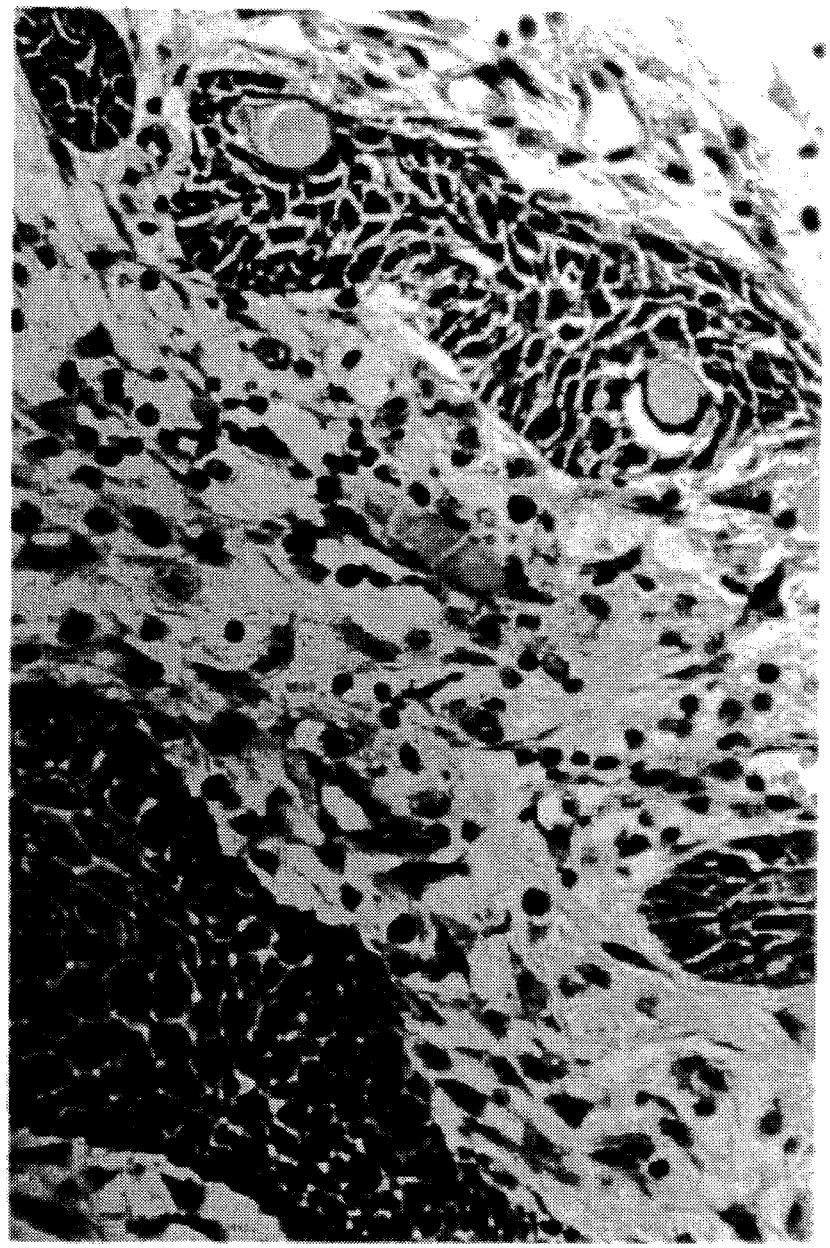

FIG. 22. is a photomicrograph showing histological evaluation of a biopsy taken from site treated with mesh soaked in human dermal fibroblast lysate. Note the increase in epithelial cell migration around individual mesh fibers.

Figure 23:

FIG. 23. is a photomicrograph showing histological evaluation of a dermal equivalent 21 days after implantation. Epithelial cells have migrated onto the dermal surface, attached evenly, and exhibit normal differentiation and growth. The growth of deep rete pegs is characteristic of transplanted skin. Resolution of the rete pegs is seen within three to four months.

Figure 24:
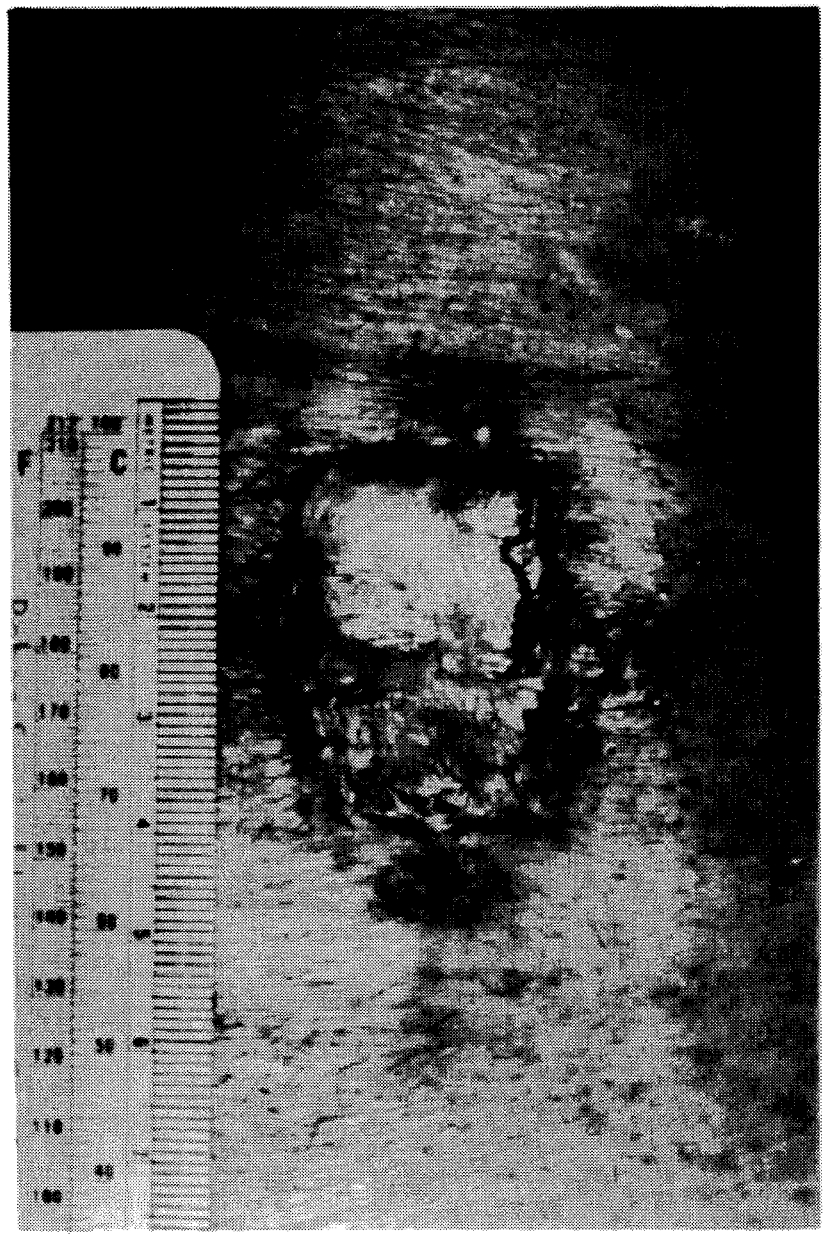

FIG. 24. is a photograph of a full thickness wound 21 days after treatment with neodermis. Half of the neodermis has received an autologous cultured epithelial graft. The epithelial graft healed evenly, prevented further contraction, and firmly attached to the underlying dermal equivalent.

Figure 25:
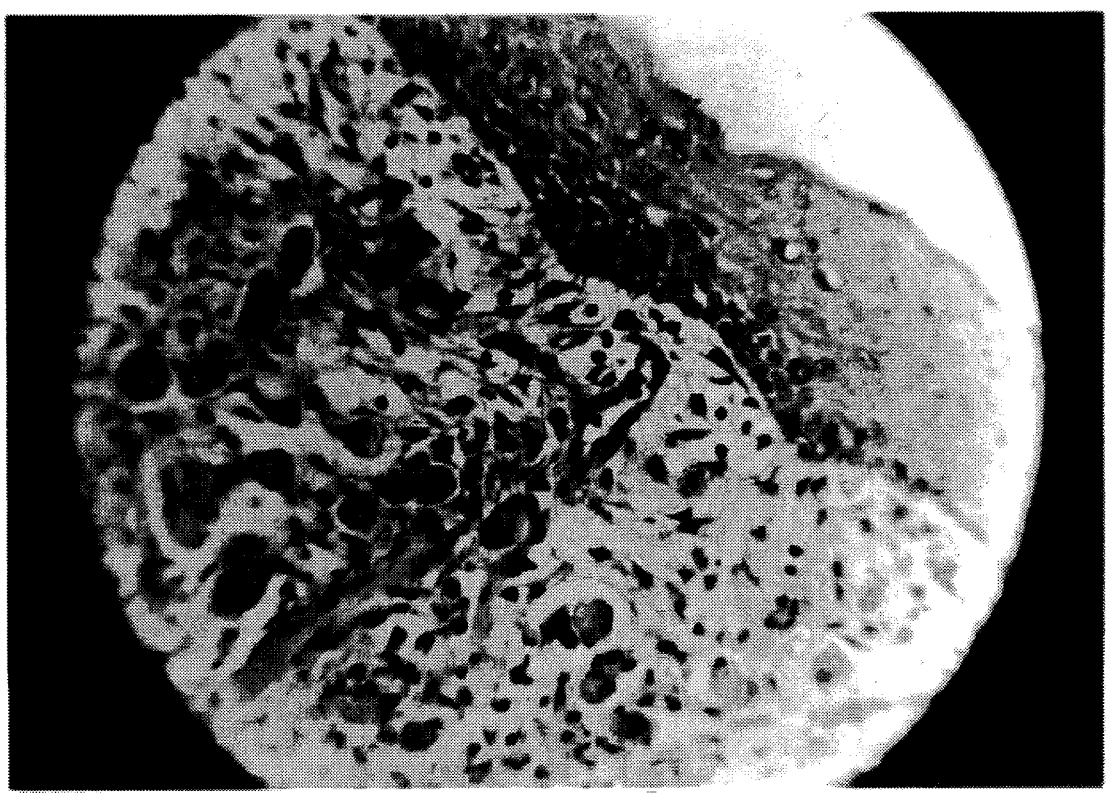

FIG. 25. is a photomicrograph showing histological evaluation of the epidermal/dermal site depicted in Figure N. Note the even growth and attachment of the keratinocytes to the dermal equivalent. Mesh fibers are still evident 21 days after-transplant and fibroblasts remain active among naturally secreted collagen fibers.

5. DETAILED DESCRIPTION OF THE INVENTION: THE THREE-DIMENSIONAL CELL CULTURE SYSTEM

The present invention involves a three-dimensional matrix and its use as the framework for a three-dimensional, multi-layer cell culture system. In previously known tissue culture systems, the cells were grown in a monolayer. Cells grown on a three-dimensional stromal support, in accordance with the present invention, grow in multiple layers, forming a cellular matrix. This matrix system approaches physiologic conditions found in vivo to a greater degree than previously described monolayer tissue culture systems. The three-dimensional cell culture system is applicable to the proliferation of different types of cells and formation of a number of different tissues, including but not limited to bone marrow, skin, liver, pancreas, kidney, adrenal and neurologic tissue, to name but a few.

The culture system has a variety of applications. For example, for tissues such as skin, glands, etc. the three-dimensional culture itself may be transplanted or implanted into a living organism. Alternatively, for diffuse tissues such as bone marrow, the proliferating cells could be isolated from the culture system for transplantation. The three-dimensional cultures may also be used in vitro for cytotoxicity testing and screening compounds. In yet another application, the three-dimensional culture system may be used as a "bioreactor" to produce cellular products in quantity.

In accordance with the invention, cells derived from a desired tissue (herein referred to as tissue-specific cells or parenchymal cells) are inoculated and cultured on a pre-established three-dimensional stromal matrix. The stromal matrix comprises stromal cells grown on a three-dimensional matrix or network. The stromal cells comprise fibroblasts with or without additional cells and/or elements described more fully herein. The fibroblasts and other cells and/or elements that comprise the stroma may be fetal or adult in origin, and may be derived from convenient sources such as skin, liver, pancreas, etc. Such tissues and/or organs can be obtained by appropriate biopsy or upon autopsy. In fact, cadaver organs may be used to provide a generous supply of stromal cells and elements.

Fetal fibroblasts will support thee growth of many different cells and tissues in the three-dimensional culture system, and, therefore, can be inoculated onto the matrix to form a "generic" stromal support matrix for culturing any of a variety of cells and tissues. However, in certain instances, it may be preferable to use a "specific" rather than "generic" stromal support matrix, in which case stromal cells and elements can be obtained from a particular tissue, organ, or individual. For example, where the three-dimensional culture is to be used for purposes of transplantation or implantation in vivo, it may be preferable to obtain the stromal cells and elements from the individual who is to receive the transplant or implant. This approach might be especially advantageous where immunological rejection of the transplant and/or graft versus host disease is likely. Moreover, fibroblasts and other stromal cells and/or elements may be derived from the same type of tissue to be cultured in the three-dimensional system. This might be advantageous when culturing tissues in which specialized stromal cells may play particular structural/functional roles; e.g., glial cells of neurological tissue, Kupffer cells of liver, etc.

Once inoculated onto the three-dimensional matrix, the stromal cells will proliferate on the matrix and support the growth of tissue-specific cells inoculated into the three-dimensional culture system of the invention. In fact, when inoculated with the tissue-specific cells, the three-dimensional stromal support matrix will sustain active proliferation of the culture for long periods of time. Growth and regulatory factors may be added to the culture, but are not necessary since they are elaborated by the stromal support matrix.

Because, according to the invention, it is important to recreate, in culture, the cellular microenvironment found in vivo for a particular tissue, the extent to which the stromal cells are grown prior to inoculation of parenchymal cells may vary depending on the type of tissue to be grown in three-dimensional tissue culture. For example, in bone marrow three-dimensional cultures, it is preferable to inoculate hematopoietic cells onto a stromal matrix which is subconfluent. However, in skin three-dimensional tissue cultures, it is preferred, according to the invention, to allow the stromal cells to reach confluence prior to inoculation with keratinocytes and/or melanocytes, so as to recreate the structure of the dermal component of skin. Importantly, because openings in the mesh permit the exit of stromal cells in culture, confluent stromal cultures do not exhibit contact inhibition, and the stromal cells continue to grow, divide, and remain functionally active.

The invention is based, in part, upon the discovery that growth of the stromal cells in three dimensions will sustain active proliferation of both the stromal and tissue-specific cells in culture for much longer time periods than will monolayer systems. Moreover, the three-dimensional system supports the maturation, differentiation, and segregation of cells in culture in vitro to form components of adult tissues analogous to counterparts found in vivo.

Although the applicants are under no duty or obligation to explain the mechanism by which the invention works, a number of factors inherent in the three-dimensional culture system may contribute to its success:

(a) The three-dimensional matrix provides a greater surface area for protein attachment, and consequently, for the adherence of stromal cells.

(b) Because of the three-dimensionality of the matrix, stromal cells continue to actively grow, in contrast to cells in monolayer cultures, which grow to confluence, exhibit contact inhibition, and cease to grow and divide. The elaboration of growth and regulatory factors by replicating stromal cells may be partially responsible for stimulating proliferation and regulating differentiation of cells in culture.

(c) The three-dimensional matrix allows for a spatial distribution of cellular elements which is more analogous to that found in the counterpart tissue in vivo.

(d) The increase in potential volume for cell growth in the three-dimensional system may allow the establishment of localized microenvironments conducive to cellular maturation.

(e) The three-dimensional matrix maximizes cell—cell interactions by allowing greater potential for movement of migratory cells, such as macrophages, monocytes and possibly lymphocytes in the adherent layer.

(f) It has been recognized that maintenace of a differentiated cellular phenotype requires not only growth/differentiation factors but also the appropriate cellular interactions. The present invention effectively recreates the tissue microenvironment.

The three-dimensional stromal support, the culture system itself, and its maintenance, as well as various uses of the three-dimensional cultures are described in greater detail in the subsections below.

5.1. Establishment of Three-Dimensional Stromal Matrix

The three-dimensional support may be of any material and/or shape that: (a) allows cells to attach to it (or can be modified to allow cells to attach to it); and (b) allows cells to grow in more than one layer. A number of different materials may be used to form the matrix, including but not limited to: nylon (polyamides), dacron (polyesters), polystyrene, polypropylene, polyacrylates, polyvinyl compounds (e.g., polyvinylchloride), polycarbonate (PVC), polytetrafluoroethylene (PTFE; teflon), thermanox (TPX), nitrocellulose, cotton, polyglycolic acid (PGA), cat gut sutures, cellulose, gelatin, dextran, etc. Any of these materials may be woven into a mesh, for example, to form the three-dimensional matrix. Certain materials, such as nylon, polystyrene, etc., are poor substrates for cellular attachment. When these materials are used as the three-dimensional support matrix, it is advisable to pre-treat the matrix prior to inoculation of stromal cells in order to enhance the attachment of stromal cells to the matrix. For example, prior to inoculation with stromal cells, nylon matrices could be treated with 0.1M acetic acid, and incubated in polylysine, FBS, and/or collagen to coat the nylon. Polystyrene could be similarly treated using sulfuric acid.

Where the three-dimensional culture is itself to be implanted in vivo, it may be preferable to use biodegradable matrices such as poly glycolic acid, catgut suture material, or gelatin, for example. Where the cultures are to be maintained for long periods of time or cryopreserved, nondegradable materials such as nylon, dacron, polystyrene, polyacrylates, polyvinyls, teflons, cotton, etc. may be preferred. A convenient nylon mesh which could be used in accordance with the invention is Nitex, a nylon filtration mesh having an average pore size of 210 μm and an average nylon fiber diameter of 90 μm (#3-210/36, Tetko, Inc., N.Y.).

Stromal cells comprising fibroblasts, with or without other cells and elements described below, are inoculated onto the matrix. These fibroblasts may be derived from organs, such as skin, liver, pancreas, etc. which can be obtained by biopsy (where appropriate) or upon autopsy. In fact fibroblasts can be obtained in quantity rather conveniently from any appropriate cadaver organ. As previously explained, fetal fibroblasts can be used to form a "generic" three-dimensional stromal matrix that will support the growth of a variety of different cells and/or tissues. However, a "specific" stromal matrix may be prepared by inoculating the three-dimensional matrix with fibroblasts derived from the same type of tissue to be cultured and/or from a particular individual who is later to receive the cells and/or tissues grown in culture in accordance with the three-dimensional system of the invention.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase etc. Mechanical disruption can also be accomplished by a number of methods including, but not limited to the use of grinders, blenders, sieves, homogenizers, pressure cells, or insonators to name but a few. For a review of tissue disaggregation techniques, see Freshney, Culture of Animal Cells. A Manual of Basic Technique, 2d Ed., A. R. Liss, Inc., New York, 1987, Ch. 9, pp. 107–126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including but not limited to cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137–168.

The isolation of fibroblasts may, for example, be carried out as follows: fresh tissue samples are thoroughly washed and minced in Hanks balanced salt solution (HBSS) in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional matrix (see, Naughton et al., 1987, J. Med. 18(3&4):219–250). Inoculation of the three-dimensional matrix with a high concentration of stromal cells, e.g., approximately $10^6$ to $5 \times 10^7$ cells/ml, will result in the establishment of the three-dimensional stromal support in shorter periods of time.

In addition to fibroblasts, other cells may be added to form the three-dimensional stromal matrix required to support long term growth in culture. For example, other cells found in loose connective tissue may be inoculated onto the three-dimensional support along with fibroblasts. Such cells include but are not limited to endothelial cells, pericytes, macrophages, monocytes, plasma cells, mast cells, adipocytes, etc. These stromal cells may readily be derived from appropriate organs such as skin, liver, etc., using methods known in the art such as those discussed above. In one embodiment of the invention, stromal cells which are specialized for the particular tissue to be cultured may be added to the fibroblast stroma. For example, stromal cells of hematopoietic tissue, including but not limited to fibroblasts, endothelial cells, macrophages/monocytes, adipocytes and reticular cells, could be used to form the three-dimensional subconfluent stroma for the long term culture of bone marrow in vitro. Hematopoietic stromal cells may be readily obtained from the "buffy coat" formed in bone marrow suspensions by centrifugation at low forces, e.g., 3000×g. Stromal cells of liver may include fibroblasts, Kupffer cells, and vascular and bile duct endothelial cells. Similarly, glial cells could be used as the stroma to support the proliferation of neurological cells and tissues; glial cells for this purpose can be obtained by trypsinization or collagenase digestion of embryonic or adult brian (Ponten and Westermark, 1980, in Federof, S. Hertz, L., eds, "Advances in Cellular Neurobiology," Vol. 1, New York, Academic Press, pp.209–227).

Again, where the cultured cells are to be used for transplantation or implantation in vivo it is preferable to obtain the stromal cells from the patient's own tissues. The growth of cells in the presence of the three-dimensional stromal support matrix may be further enhanced by adding to the matrix, or coating the matrix support with proteins (e.g., collagens, elastic fibers, reticular fibers) glycoproteins, glycosaminoglycans (e.g., heparan sulfate, chondroitin-4-sulfate, chondroitin-6-sulfate, dermatan sulfate, keratan sulfate, etc.), a cellular matrix, and/or other materials.

After inoculation of the stromal cells, the three-dimensional matrix should be incubated in an appropriate nutrient medium. Many commercially available media such as RPMI 1640, Fisher's, Iscove's, McCoy's, and the like may be suitable for use. It is important that the three-dimensional stromal matrix be suspended or floated in the medium during the incubation period in order to maximize proliferative activity. In addition, the culture should be "fed" periodically to remove the spent media, depopulate released cells, and add fresh media.

During the incubation period, the stromal cells will grow linearly along and envelop the three-dimensional matrix before beginning to grow into the openings of the matrix. It is important to grow the cells to an appropriate degree which reflects the amount of stromal cells present in the in vivo tissue prior to inoculation of the stromal matrix with the tissue-specific cells.

The openings of the matrix should be of an appropriate size to allow the stromal cells to stretch across the openings. Maintaining actively growing stromal cells which stretch across the matrix enhances the production of growth factors which are elaborated by the stromal cells, and hence will support long term cultures. For example, if the openings are too small, the stromal cells may rapidly achieve confluence but be unable to easily exit from the mesh; trapped cells may exhibit contact inhibition and cease production of the appropriate factors necessary to support proliferation and maintain long term cultures. If the openings are too large, the stromal cells may be unable to stretch across the opening; this will also decrease stromal cell production of the appropriate factors necessary to support proliferation and maintain long term cultures. When using a mesh type of matrix, as exemplified herein, we have found that openings ranging from about 150 μm to about 220 μm will work satisfactorily. However, depending upon the three-dimensional structure and intricacy of the matrix, other sizes may work equally well. In fact, any shape or structure that allow the stromal cells to stretch and continue to replicate and grow for lengthy time periods will work in accordance with the invention.

Different proportions of the various types of collagen deposited on the matrix can affect the growth of the later inoculated tissue-specific cells. For example, for optimal growth of hematopoietic cells, the matrix should preferably contain collagen types III, IV and I in an approximate ratio of 6:3:1 in the initial matrix. For three-dimensional skin culture systems, collagen types I and III are preferably deposited in the initial matrix. The proportions of collagen types deposited can be manipulated or enhanced by selecting fibroblasts which elaborate the appropriate collagen type. This can be accomplished using monoclonal antibodies of an appropriate isotype or subclass that is capable of activating complement, and which define particular collagen types. These antibodies and complement can be used to negatively select the fibroblasts which express the desired collagen type. Alternatively, the stroma used to inoculate the matrix can be a mixture of cells which synthesize the appropriate collagen types desired. The distribution and origins of the five types of collagen is shown in Table I.

TABLE I

DISTRIBUTIONS AND ORIGINS OF THE FIVE TYPES OF COLLAGEN

| Collagen Type | Principal Tissue Distribution | Cells of Origin |
|---|---|---|
| I | Loose and dense ordinary connective tissue; collagen fibers | Fibroblasts and reticular cells; smooth muscle cells |
| | Fibrocartilage | |
| | Bone | osteoblast |
| | Dentin | odontoblasts |
| II | Hyaline and elastic cartilage | Chondrocytes |
| | Vitreous body of eye | Retinal cells |
| III | Loose connective tissue; reticular fibers | Fibroblasts and reticular cells |
| | Papillary layer of dermis | |
| | Blood vessels | Smooth muscle cells; endothelial cells |
| IV | Basement membranes | Epithelial and endothelial cells |
| | Lens capsule of eye | Lens fibers |
| V | Fetal membranes; Placenta Basement membranes Bone | Fibroblasts |
| | Smooth muscle | Smooth muscle cells |

Thus, depending upon the tissue to be cultured and the collagen types desired, the appropriate stromal cell(s) may be selected to inoculate the three-dimensional matrix.

During incubation of the three-dimensional stromal support, proliferating cells may be released from the matrix. These released cells may stick to the walls of the culture vessel where they may continue to proliferate and form a confluent monolayer. This should be prevented or minimized, for example, by removal of the released cells during feeding, or by transferring the three-dimensional stromal matrix to a new culture vessel. The presence of a confluent monolayer in the vessel will "shut down" the growth of cells in the three-dimensional matrix and/or culture. Removal of the confluent monolayer or transfer of the matrix to fresh media in a new vessel will restore proliferative activity of the three-dimensional culture system. Such removal or transfers should be done in any culture vessel which has a stromal monolayer exceeding 25% confluency. Alternatively, the culture system could be agitated to prevent the released cells from sticking, or instead of periodically feeding the cultures, the culture system could be set up so that fresh media continuously flows through the system. The flow rate could be adjusted to both maximize proliferation within the three-dimensional culture, and to wash out and remove cells released from the matrix, so that they will not stick to the walls of the vessel and grow to confluence. In any case, the released stromal cells can be collected and cryopreserved for future use.

5.2. Inoculation of Tissue-Specific Cells onto Three-dimensional Stromal Matrix and Maintenance of Cultures Once the three-dimensional stromal matrix has reached the appropriate degree of growth, the tissue-specific cells (parenchymal cells) which are desired to be cultured are inoculated onto the stromal matrix. A high concentration of cells in the inoculum will advantageously result in increased proliferation in culture much sooner than will low concentrations. The cells chosen for inoculation will depend upon the tissue to be cultured, which may include but is not limited to bone marrow, skin, liver, pancreas, kidney, neurological tissue, and adrenal gland, to name but a few.

For example, and not by way of limitation, a variety of epithelial cells can be cultured on the three-dimensional living stromal support. Examples of such epithelial cells include, but are not limited to, oral mucosa and gastrointestinal (G.I.) tract cells. Such epithelial cells may be isolated by enzymatic treatment of the tissue according to methods known in the art, followed by expansion of these cells in culture and application of epithelial cells to the three-dimensional stromal support cell matrix (neo-submucosa). The presence of the submucosa provides growth factors and other proteins which promote normal division and differentiation of the oral mucosa cells and the cells of the G.I. tract lining. Using this methodology other epithelial cells can be grown successfully, including nasal epithelium, respiratory tract epithelium, vaginal epithelium, and corneal epithelium.

A variety of tumors may be grown on the three-dimensional living stromal support. Examples of such tumors include but are not limited to adenocarcinoma and malignant melanoma which may be derived from primary or metastatic sites. Such cultures may be established in a manner similar to other three-dimensional epithelial cultures. Briefly, stromal cells, derived from either the patient's tumor or normal tissue or from an allogeneic source, are established on the mesh. After reaching near-confluency the stromal cells are inoculated with tumor cells. The tumor cells will continue to divide rapidly and form a three-dimensional solid tumor. Tumor cells grown in such a three-dimensional support exhibit a morphology similar to the in vivo state and express and shed surface antigens in a manner similar to that of solid tumors; malignant cells grown in monolayers do not exhibit the same degree of similarity to in vivo tumor tissue. Such a physiological growth of tumor cells allows applications in the study and development of new chemotherapeutic agents, individualized chemotherapy regimens, and mechanisms of metastasis. In addition such tumor cultures may be useful in individualized immunotherapy. In this regard experimentation with $^{51}$CR release studies has indicated that Lak cells evoke a much more potent response against tumor cells grown in three-dimensions as compared to cells cultured in monolayer. Immune cells may be obtained from patients by traditional pheresis techiques and sensitized to the patient's own tumor cells grown in three-dimensional culture.

In general, this inoculum should include the "stem" cell (also called the "reserve" cell) for that tissue; i.e., those cells which generate new cells that will mature into the specialized cells that form the various components of the tissue.

The parenchymal or tissue-specific cells used in the inoculum may be obtained from cell suspensions prepared by disaggregating the desired tissue using standard techniques described for obtaining stromal cells in Section 5.1 above. The entire cellular suspension itself could be used to inoculate the three-dimensional stromal support matrix. As a result, the regenerative cells contained within the homogenate will proliferate, mature, and differentiate properly on the matrix, whereas non-regenerative cells will not. Alternatively, particular cell types may be isolated from appropriate fractions of the cellular suspension using standard techniques described for fractionating stromal cells in Section 5.1 above. Where the "stem" cells or "reserve" cells can be readily isolated, these may be used to preferentially inoculate the three-dimensional stromal support. For example, when culturing bone marrow, the three-dimensional stroma may be inoculated with bone marrow cells, either fresh or derived from a cryopreserved sample. When culturing skin, the three-dimensional stroma may be inoculated with melanocytes and keratinocytes. When culturing liver, the three-dimensional stroma may be inoculated with hepatocytes. When culturing pancreas, the three-dimensional stroma may be inoculated with pancreatic endocrine cells. For a review of methods which may be utilized to obtain parenchymal cells from various tissues, see, Freshney, Culture of Animal Cells. A Manual of Basic Technique, 2d Ed., A. R. Liss, Inc., New York, 1987, Ch. 20, pp. 257–288.

During incubation, the three-dimensional cell culture system should be suspended or floated in the nutrient medium. Cultures should be fed with fresh media periodically. Again, care should be taken to prevent cells released from the culture from sticking to the walls of the vessel where they could proliferate and form a confluent monolayer. The release of cells from the three-dimensional culture appears to occur more readily when culturing diffuse tissues as opposed to structured tissues. For example, the three-dimensional skin culture of the invention is histologically and morphologically normal; the distinct dermal and epidermal layers do not release cells into the surrounding media. By contrast, the three-dimensional bone marrow cultures of the invention release mature non-adherent cells into the medium much the way such cells are released in marrow in vivo. As previously explained, should the released cells stick to the culture vessel and form a confluent monolayer, the proliferation of the three-dimensional culture will be "shut down". This can be avoided by removal of released cells during feeding, transfer of the three-dimensional culture to a new vessel, by agitation of the culture to prevent sticking of released cells to the vessel wall, or by the continuous flow of fresh media at a rate sufficient to replenish nutrients in the culture and remove released cells. In any case, the mature released cells could be collected and cryopreserved for future use.

Growth factors and regulatory factors need not be added to the media since these types of factors are elaborated by the three-dimensional stromal cells. However, the addition of such factors, or the inoculation of other specialized cells may be used to enhance, alter or modulate proliferation and cell maturation in the cultures. The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include prostaglandins, interleukins, and naturally-occurring chalones.

5.3. Uses of the Three-Dimensional Culture System

The three-dimensional culture system of the invention can be used in a variety of applications. These include but are not limited to transplantation or implantation of either the cultured cells obtained from the matrix, or the cultured matrix itself in vivo; screening cytotoxic compounds, allergens, growth/regulatory factors, pharmaceutical compounds, etc., in vitro; elucidating the mechanism of certain diseases; studying the mechanism by which drugs and/or growth factors operate; diagnosing and monitoring cancer in a patient; gene therapy; and the production of biologically active products, to name but a few.

For transplantation or implantation in vivo, either the cells obtained from the culture or the entire three-dimensional culture could be implanted, depending upon the type of tissue involved. For example, three-dimensional bone marrow cultures can be maintained in vitro for long periods; the cells isolated from these cultures can be used in transplantation or the entire culture may be implanted. By contrast, in skin cultures, the entire three-dimensional culture can be grafted in vivo for treating burn victims, skin ulcerations, wounds, etc.

Three-dimensional tissue culture implants may, according to the invention, be used to replace or augment existing tissue, to introduce new or altered tissue, to modify artificial prostheses, or to join together biological tissues or structures. For example, and not by way of limitation, specific embodiments of the invention would include (i) three-dimensional bone marrow culture implants used to replace bone marrow destroyed during chemotherapeutic treatment; (ii) three-dimensional liver tissue implants used to augment liver function in cirrhosis patients; (iii) geneticaly altered cells grown in three-dimensional culture (such as three-dimensonal cultures of fibroblasts which express a recombinant gene encoding insulin); (iv) hip prostheses coated with three-dimensional cultures of cartilage; (v) dental prostheses joined to a three-dimensional culture of oral mucosa.

The three-dimensional cultures may be used in vitro to screen a wide variety of compounds, such as cytotoxic compounds, growth/regulatory factors, pharmaceutical agents, etc. To this end, the cultures are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the three-dimensional system may be assessed. For example, drugs that increase red blood cell formation can be tested on the three-dimensional bone marrow cultures. Drugs that affect cholesterol metabolism, e.g., by lowering cholesterol production, could be tested on the three-dimensional liver system. Three-dimensional cultures of tumor cells may be used as model systems to test, for example, the efficacy of anti-tumor agents.

The three-dimensional cultures of the invention may be used as model systems for the study of physiologic or pathologic conditions. For example, in a specific embodiment of the invention, a three-dimensional culture system may be used as a model for the blood-brain barrier; such a model system can be used to study the penetration of substances through the blood-brain barrier. In an additional specific embodiment, and not by way of limitation, a three-dimensional culture of mucosal epithelium may be used as a model system to study herpesvirus or papillomavirus infection; such a model system can be used to test the efficacy of anti-vital medications.

The three-dimensional cell cultures may also be used to aid in the diagnosis and treatment of malignancies and diseases. For example, a biopsy of any tissue (e.g. bone marrow, skin, liver, etc.) may be taken from a patient suspected of having a malignancy. If the biopsy cells are cultured in the three-dimensional system of the invention, malignant cells will be clonally expanded during proliferation of the culture. This will increase the chances of detecting a malignancy and, therefore, increase the accuracy of the diagnosis. This may be especially useful in diseases such as AIDS where the infected population of cells is depleted in vivo. Moreover, the patient's culture could be used in vitro to screen cytotoxic and/or pharmaceutical compounds in order to identify those that are most efficacious; i.e. those that kill the malignant or diseased cells, yet spare the normal cells. These agents could then be used to therapeutically treat the patient.

According to the present invention, a relatively small volume of bone marrow from a diseased patient may be harvested and the patient's bone marrow destroyed by chemotherapy or radiation. The bone marrow sample may then be purged of diseased cells using an appropriate chemotherapeutic agent, expanded in vitro, and then readministered to the patient. In additon to allowing a more effective purge by treating smaller volumes of diseased marrow followed by expansion in vitro, the three-dimensional culture system can be utilized on larger volumes of purged marrow. A side effect of most purging agents is destruction and disruption of normal hematopoietic skin cells, which results in a prolonged time to engraftment and often patient mortality due to secondary infection. One effective purging agent utilized with acute nonlymphocytic leukemia is 4-hydroperoxyoyolo phosphamide (4HC) which causes a two log kill of malignant cells. In traditional treatment, 500 ml–1000 ml of diseased marrow is treated by incubation of the marrow ex vivo with 60–100 ng of 4HC/ml. Marrow is then cryopreseved and reinfused into the patient after 2–3 weeks of clinical chemotherapy. According to the present invention, a comparable volume of bone marrow may be harvested, purged with 4HC, and then expanded in vitro in three-dimensional culture, thereby allowing a more rapid engraftment time and a decrease in patient mortality.

In vitro methodologies have been useful in reducing rejection of cells used for transplantation in both animals (bone marrow transplantation in mice) and humans (allogeneic epidermal grafts). The three-dimensional bone marrow culture can be further used to promote a tolerance of cells to foreign antigens. In this regard donor hematopoietic cells may be grown in three-dimensional stromal cells from the recipient. Such cultures may be grown in the presence of three-dimensional thymic cultures which provide additional growth factors and differentiation factors which will induce maturation of lymphocytes in the bone marrow system. As the hematopoietic cells replicate and mature they will be educated to see the recipient cell antigens as "self" thereby can be come tolerant to these "foreign" cells.

Depending upon the intended use for the proliferated cells and tissue, various specialized cells may be added to the three-dimensional culture. For example, the long term growth of bone marrow cells in the three-dimensional cultures may be enhanced by the addition of certain mononuclear cell populations to the cultures by the addition of growth factors to the culture medium, or by the use of stromal cells manipulated so as to produce a desired growth factor or factors. Cells collected from these cultures may be used for transfusion transplantation and banking. The addition of lymphocytes derived from a patient to three-dimensional skin cultures may assist in evaluating and diagnosing immunological disorders, such as certain autoimmune diseases. Similarly, the addition of lymphocytes and mast cells derived from a patient to three-dimensional skin cultures may assist in evaluating the patient's allergic response to various allergens without exposing the patient to the allergens. To this end, the three-dimensional skin culture containing the patient's lymphocytes and mast cells is exposed to various allergens. Binding of lymphocyte-generated IgE to resident mast cells, when "bridged" with the allergen to which the patient is sensitive, will result in the release of vasoactive mediators, such as histamine. The release of such mediators in culture, in response to exposure of the three-dimensional culture to an allergen could be measured and used as an indication of the patient's allergic response. This would allow allergy tests to be conducted without exposing the individual to dangerous and potentially harmful allergens. This system could similarly be used for testing cosmetics in vitro.

The three-dimensional culture system of the invention may afford a vehicle for introducing genes and gene products in vivo for use in gene therapies. For example, using recombinant DNA techniques, a gene for which a patient is deficient could be placed under the control of a viral or tissue-specific promoter. The recombinant DNA construct containing the gene could be used to transform or transfect a host cell which is cloned and then clonally expanded in the three-dimensional culture system. The three-dimensional culture which expresses the active gene product, could be implanted into an individual who is deficient for that product.

The use of the three-dimensional culture in gene therapy has a number of advantages. Firstly, since the culture comprises eukaryotic cells, the gene product will be properly expressed and processed in culture to form an active product. Secondly, gene therapy techniques are useful only if the number of transfected cells can be substantially enhanced to be of clinical value, relevance, and utility; the three-dimensional cultures of the invention allow for expansion of the number of transfected cells and amplification (via cell division) of transfected cells.

Preferably, the expression control elements used should allow for the regulated expression of the gene so that the product is synthesized only when needed in vivo. The promoter chosen would depend, in part upon the type of tissue and cells cultured. Cells and tissues which are capable of secreting proteins (e.g., those characterized by abundant rough endoplasmic reticulum and golgi complex) are preferable. To this end, liver and other glandular tissues could be selected. When using liver cells, liver specific viral promoters, such as hepatitis B virus elements, could be used to introduce foreign genes into liver cells and regulate the expression of such genes. These cells could then be cultured in the three-dimensional system of the invention. Alternatively, a liver-specific promoter such as the albumin promoter could be used.

Examples of transcriptional control regions that exhibit tissue specificity which have been described and could be used, include but are not limited to: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:42S–51S); insulin gene control region which is active in pancreatic beta cells (Hanahan, 1985, Nature 315:115–122); immunoglobulin gene control region which is active in lymphoid cells (Grosschedl et al., 1984, Cell 38:647–658; Adams et al., 1985, Nature 318:533–538; Alexander et al., 1987,Mol. Cell. Biol. 7:1436–1444); albumin gene control region which is active in liver (Pinkert et al., 1987, Genes and Devel. 1:268–276); alpha-fetoprotein gene control region which is active in liver (Krumlauf et al., 1985,Mol. Cell. Biol. 5:1639–1648; Hammer et al., 1987, Science 235:53–58); alpha-1-antitrypsin gene control region which is active in liver (Kelsey et al., 1987, Genes and Devel. 1:161–171); beta-globin gene control region which is active in myeloid cells (Magram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286); and gonadotropic releasing hormone gene control region which is active in the hypothalamus (Mason et al., 1986, Science 234:1372–1378).

In a further embodiment of the invention, three-dimensional cultures may be used to facilitate gene transduction. For example, and not by way of limitation, three-dimensional cultures of fibroblast stroma comprising a recombinant virus expression vector may be used to transfer the recombinant virus into cells brought into contact with the stromal matrix, thereby simulating viral transmission in vivo. The three-dimensional culture system is a more efficient way of accomplishing gene transduction than are current techniques for DNA tansfection.

In yet another embodiment of the invention, the three-dimensional culture system could be use in vitro to produce biological products in high yield. For example, a cell which naturally produces large quantities of a particular biological product (e.g., a growth factor, regulatory factor, peptide hormone, antibody, etc.), or a host cell genetically engineered to produce a foreign gene product, could be clonally expanded using the three-dimensional culture system in vitro. If the transformed cell excretes the gene product into the nutrient medium, the product may be readily isolated from the spent or conditioned medium using standard separation techniques (e.g., HPLC, column chromatography, electrophoretic techniques, to name but a few). A "bioreactor" could be devised which would take advantage of the continuous flow method for feeding the three-dimensional cultures in vitro. Essentially, as fresh media is passed through the three-dimensional culture, the gene product will be washed out of the culture along with the cells released from the culture. The gene product could be isolated (e.g., by HPLC column chromatography, electrophoresis, etc) from the outflow of spent or conditioned media.

Various sample embodiments of the invention are described in the sections below. For purposes of description only, and not by way of limitation, the three-dimensional culture system of the invention is described based upon the type of tissue and cells used in various systems. These descriptions specifically include but are not limited to bone marrow, skin, liver, and pancreas but it is expressly understood that the three-dimensional culture system can be used with other types of cells and tissues. The invention is also illustrated by way of examples, which demonstrate characteristic data generated for each system described.

6. THREE-DIMENSIONAL BONE MARROW CULTURE SYSTEM

The three-dimensional culture of the present invention provides for the replication of bone marrow cells in vitro, in a system comparable to physiologic conditions. Importantly, the bone marrow cells replicated in this system include all of the cells present in normal bone marrow, assuming all cell types were present in the original bone marrow inoculum used to initiate the cultures.

Although marrow cells are capable of limited growth when cultured alone, long term growth of these cultures is possible only if stromal cells or their secretory products are present. See, Long-Term Bone Marrow Culture, D. G. Wright & J. S. Greenberger, eds., A. R. Liss, New York, (1984) pp. 141–156.

In accordance with the invention, bone marrow cells, are grown on a three-dimensional support in co-cultures with stromal cells comprising fibroblasts (of either fetal or bone marrow origin) or a mixture of cell types which comprise the stromal components of normal marrow, including fibroblasts, macrophages, reticular cells, and adipocytes. Factors derived from media of splenic and/or hepatic (liver) macrophage cultures or from subsets of stromal cells may optionally be added to the culture. The three-dimensional culture system of the present invention appears to maximize the proliferation of multipotential hematopoietic stem cells which have the capability of repopulating bone marrow when the bone marrow has been destroyed by intrinsically or environmentally-mediated disease or by the treatment of such disease with chemotherapy and/or radiation.

Using conventional monolayer cell culture techniques, stem cells which have marrow repopulating activity (MRA) have been shown to persist and replicate in long term murine bone marrow cultures. In such systems, however, mature hematopoietic cell expression is limited primarily to the myeloid and monocytoid lineages. Monolayer cultures of human and non-human primate bone marrow cells exhibit a steady decline, over time, in assayable progenitors (CFU-GM, CFU-GEMM, BFU-E, etc.). The major mature cell expressed by these monolayer cultures, as in the murine system, is the granulocyte. By contrast, hematopoietic progenitors and hematopoietic precursors of all blood cell lineages appear to replicate and proliferate in the three-dimensional stromal system of the present invention. Furthermore, differentiation appears to proceed in a physiologic manner. For example, erythroid, myeloid, lymphoid, macrophagic, and megakaryocytic colonies can continuously arise in the same culture using the systems as taught by the present invention and described below. Stem cell replication in this system can be inferred from the sustained proliferation of committed progenitors.

6.1. Obtaining Bone Marrow Cells

Bone marrow cells used in the inoculum may be obtained directly from the donor or retrieved from cryopreservative storage. The cells are first separated from their reticulum by physical means. Accordingly, a small amount (10–15 cc bone marrow/peripheral blood suspension) may be aspirated from the iliac crest of a donor. For purposes of transplantation the results of the process are optimal if: (a) the individual is under 40 years of age at the time his/her marrow is taken for culture and/or cryopreservation; and (b) the patient is disease-free; however, the invention is not limited to these criteria. Methods of aspirating bone marrow from a donor are well known in the art. Examples of apparatus and processes for aspirating bone marrow from a donor can be found in U.S. Pat. Nos. 4,481,946 and 4,486,188.

If the bone marrow is to be cultured in order to treat certain patients with metastatic disease or hematological malignancies, the marrow obtained from the patients should be "purged" of malignant cells by physical or chemotherapeutic means prior to culturing. At present, physical and chemotherapeutic purging methods require a large sample size because these methods kill both malignant and normal cells nonselectively. However, selective methods are currently being developed for purging. For example, antibodies specific for malignant cells are being tested in an attempt to target toxic agents, and specifically kill malignant cells. Such selective purging methods would be efficient if the sample size is small. The three-dimensional culture system of the invention makes this feasible in that a small sample can be purged efficiently and the remaining healthy cells expanded. The bone marrow removed from the donor can be replicated or preserved for replication at a later date. If the bone marrow is to be preserved, the bone marrow can be incrementally frozen using computerized cryotechnological equipment. For example, fresh marrow/blood suspension may be aliquoted in equal volumes into sterile Nunc tubes and placed in a beaker of crushed ice until the cryopreservation chamber is brought to a similar temperature (4° C.). Immediately prior to specimen insertion into the chamber, a solution is added to each Nunc tube using sterile technique, so that the cryoprotectants, dimethylsulfoxide and glycerol, will be present at final concentrations of about 7% and 5%, respectively. The freezing program is initiated immediately after introduction of the specimen. Freezing program number 1 on the CryoMed Model Number 1010 controller is used.

Using this technique, the cellular viability after freezing and rapid thawing in an 80° C. water bath exceeds 90% as assayed by the trypan blue exclusion method. In addition, greater than 80% of the original colony forming unit culture (CFU-C) may be recovered after freezing. Examples of systems for freezing bone marrow and biological substances in accordance with a precalculated temperature and time curve are disclosed in U.S. Pat. Nos. 4,107,937 and 4,117,881. Preferably, the bone marrow cells are stored in the liquid phase of liquid nitrogen at a temperature of –196° C. at which temperature all cellular metabolic activity has ceased.

6.2. Establishment of the Three-Dimensional Stromal Matrix

Stromal cells derived from bone marrow suspensions should be separated from other marrow components. This may be accomplished using any suitable method known in the art. For example, marrow suspensions may be centrifuged at low forces, e.g., 3000×g for 20 minutes to obtain a white base of cells (i.e., the "buffy coat") containing macrophages, fibroblasts, adipocytes, mononuclear blood cells, reticular cells, endothelial cells. The cells of the buffy coat can be suspended in any suitable medium such as RPMI 1640 medium which may be supplemented with FBS, HS, hydrocortisone hemisuccinate, and appropriate antibiotics.

The cells are then plated onto the three-dimensional matrix. If high concentrations of stromal cells are used in the inoculum, the stromal support matrix will achieve the appropriate degree of subconfluency in shorter time periods. For example, approximately $10^6$ to $10^7$ stromal cells per ml may be plated onto a three-dimensional matrix such as sterile nylon mesh (Tetko Corp. of New York, N.Y., USA) contained in a petri dish or other suitable chamber (e.g., Titer-Tek containers).

The inoculated mesh is then placed into a culture flask containing an appropriate volume of nutrient media. The three-dimensional cultures float, partially submerged below the surface of the media. The cultures may be incubated at about 35° C. to 37° C. in about 5% $CO_2$ in ambient air at a relative humidity in excess of about 90%. Stromal cells which are predominantly fibroblasts first grow along and completely encircle all of the nylon fibers before beginning to grow into the mesh openings. Depending upon the concentration of cells used in the inoculum, this process may take approximately 5 to 18 days. The degree of subconfluency of the stromal cells, should be consistent with that seen in FIG. 1 prior to the inoculation of hematopoietic cells.

Suspended stromal cells growing in the three-dimensional matrix can be cryopreserved using the same technique as previously described for bone marrow cells. For cryopreservation of sub-confluent cells on the mesh, the nylon mesh may be rolled and inserted into a Nunc tube containing suitable medium such as RPMI 1640 supplemented with cryoprotectants such as dimethylsulfoxide and glycerol in final concentrations of about 5% and 15% respectively. Freezing of the stromal cells on the mesh can be accomplished at initial cooling rates of –1° C./minute from +1° C. to –40° C. A cooling rate of –2° to –3° C./minute is optimum until the end stage temperature of –84° C. is achieved. Approximately 20–25% of the stromal cells may detach from the nylon mesh during this process.

6.2.1. Enhancing the Growth of Marrow Stromal Cells

The primary rate limiting factor in the growth of marrow stromal cells is the relatively low mitotic index of the fibroblasts included among the marrow stromal cells. The growth of these cells and their deposition of extracellular matrix components may be enhanced by adding hydrocortisone hemisuccinate and/or self-regulating growth factors derived from the medium of cultured human fetal fibroblasts which have a high rate of cell division.

Attachment and growth of fibroblasts on the mesh can also be enhanced by: pre-coating the mesh with solubilized collagen, types I through IV; or using a mesh which is coated or embedded with collagen secreted by fetal human fibroblasts or by adult fibroblasts (hereinafter referred to as "growth enhancing fibroblasts") which have been subsetted based upon their ability to synthesize certain collagen types. In this regard, the growth enhancing fibroblasts are lifted by mild trypsinization from the mesh upon reaching confluency (5 to 7 days for fetal human fibroblasts and 14 to 18 days for adult fibroblasts respectively) and may either be inoculated along with stromal marrow cells as previously described or cryopreserved for future use.

In one embodiment of the invention, growth enhancing fibroblasts that are synthesizing collagen and other extracellular matrix components are grown on the mesh until they reach subconfluency. A mixture of both hematopoietic and stromal bone marrow cells are then inoculated onto the subconfluent growth enhancing fibroblast meshwork.

The methods for growing, subsetting, and cryopreserving growth enhancing fibroblasts are as follows:

(a) Culture of Growth Enhancing Fibroblasts. Any suitable method may be used to culture growth enhancing fibroblasts. For example, fibroblasts may be grown in suitable medium such as RPMI 1640 supplemented with 2–10% FBS or 2–10% HS to which 1 µg/ml hydrocortisone hemisuccinate and antibiotics such as 2 µg/ml gentamycin, penicillin, streptomycin and fungizone have been added. Cultures may be grown at about 5% $CO_2$ in ambient air at 35° C. to 37° C. with a relative humidity in excess of about 90%.

(b) Subsetting Growth Enhancing Fibroblasts. A number of methods may be used to subset growth enhancing fibroblasts. For example, about $5.0 \times 10^6$ fibroblasts derived from the buffy coat of a bone marrow suspension, dermal fibroblasts, or fibroblasts derived from cadaver livers may be plated onto microtiter wells (1 $mm^2$) and grown to confluency. These cells may be lifted from the culture wells by repeated washings, usually four to five times with Hank's balanced salt solution without $Ca^{++}$ or $Mg^{++}$. The matrix remaining on the microtiter plates can be examined by indirect immunofluorescence utilizing monoclonal antibodies to various matrix components visualized by direct or indirect labels. For example, the binding of unlabeled murine IgG monoclonal antibodies specific for a particular matrix component can be visualized using enzyme-labeled or fluorescein isothiocyanate-labeled rabbit anti-mouse immunoglobulin G to ascertain the collagen types present. A negative selection may then be accomplished by a number of tecniques. For example, the suspended cells may be treated with a monoclonal antibody of an isotype that is capable of activating complement (e.g., IgG, IgM, etc.) and which defines a particular matrix component (e.g., collagen types I through IV, elastin, tropoelastin, or fibronectin) to isolate sub-populations of cells capable of synthesizing each product. If the cells are then treated with guinea pig complement, those cells to which monoclonal antibody is bound will be damaged or destroyed. The viable cells remaining in the sample can be replated onto microtiter wells as previously described, grown to confluency, and lifted. The efficiency of the isolation technique may be verified by examining the matrix secreted by the surviving cells with appropriate monoclonal antibodies visualized by direct or indirect labeling techniques.

For optimal growth of hematopoietic cells, the initial matrix should contain collagen types III, IV and I in an approximate ratio of 6:3:1.

(c) Cryopreservation of Growth Enhancing Fibroblasts. Growth enhancing fibroblasts can be cryopreserved using the same techniques as previously described for stromal cells. Like the stromal cells, some of the growth enhancing fibroblasts will also detach from the mesh during freezing. This matrix, however, still contributes to the attachment of marrow stromal cells and therefore diminishes the time required for the establishment of a matrix conducive to hematopoietic cell growth.

6.3. Inoculation with Hematopoietic Cells

Bone marrow cells are suspended in an appropriate nutrient medium (e.g., RPMI/1640 supplemented with FBS, HS, hydrocortisone, and appropriate antibiotics could be used) and inoculated onto the three-dimensional stromal support. These cells may either be fresh or derived from a formerly cryopreserved sample which has been rapidly thawed, for example, in an 80° C. hot water bath. A suitable concentration of cells are inoculated onto subconfluent stromal cell meshworks. For example, $10^6$ to $10^7$ cells can be inoculated onto the three-dimensional stromal matrices in 25 $mm^2$ plastic culture flasks and grown at about 33° C. to 34° C. and 5% $CO_2$ in ambient air. The relative humidity of these cultures should be in excess of about 90%. After 3 days, the culture temperature should be raised to about 35° C. to 37° C.

In general, hematopoietic cells will grow in the natural pockets formed by the subconfluent stromal cells and the progenitor cells will remain in the adherent layer of cells. The adherent layer are those cells attached directly to the mesh or those connected indirectly by attachment to cells that are themselves attached directly to the mesh. Although hematopoietic colonization ocurs rapidly, stromal seeding appears to be the rate limiting step for hematopoiesis, since the hematopoietic cells from the inoculum seed mainly those areas where a stromal support matrix is present. Colonization occurs in the natural interstices formed by the partially developed stromal layers and is also seen on the outermost surface of the matrix. The surface colonies are somewhat smaller than those in the matrix and appear, at times, to be part of the non-adherent zone. Actually, they are loosely attached and remain after feeding. These cells, which are also found consistently in monolayer type LTBMC, have been termed the "pseudo-adherent layer" (Coulombel et al., 1983, Blood 62:291–297).

After 4 to 5 days, mature granulocytes, mononuclear Cells, and erythrocytes appear in the non-adherent layer as observed by cytospin preparation. After 7 to 10 days, numerous hematopoietic colonies can be observed in the interstices of the mesh and are morphologically consistent with CFU-C, mixed colonies, and lymphoid colonies. Megakaryocytic growth is limited but may be observed in this matrix as well. An average 3.6 $cm^2$ culture will produce 450 to 950 CFU-C per week.

Cultures which consist of stromal cells and hematopoietic cells derived from the same individual (autologous) should be fed twice weekly. Cultures which consist of a patient's bone marrow which has been inoculated onto a stromal cell meshwork derived from another individual(s) (allogeneic) should be fed three times per week to insure adequate depopulation of mature immunocompetent cells from the non-adherent layer.

6.4. Long Term Growth of Three-dimensional Bone Marrow Cultures

Optionally, the three-dimensional bone marrow cultures may be inoculated with mononuclear cells in order to enhance long term growth. Peripheral blood mononuclear cells can be prepared from a heparinized suspension using Ficoll-hypaque or Percoll. Peripheral blood cells and bone marrow hematopoietic cells should preferably be derived from the same individual (autologous). These may be obtained via venipuncture and cryopreserved at the time the bone marrow specimen is taken. Additional peripheral blood cells could be procured from the diseased patient if needed during the culturing procedure. However, if metastatic disease is suspected, the sample should first be subjected to purging, as mentioned previously. The mononuclear cells can be inoculated onto the three dimensional culture soon after the inoculation of bone marrow cells. For example, $5\times10^5$ to $10^6$ mononuclear cells (the monocyte subpopulation is the preferred cell type within the mononuclear cell layer for this step) can be inoculated onto meshworks 4 to 5 days after the initial inoculation with bone marrow hematopoietic cells and every third week thereafter. This procedure may enhance hematopoiesis by 10 to 13% as observed on a weekly basis.

In our experience, confluent stromal cell cultures will not, or at best, will only poorly support hematopoiesis. Indefinite growth of human hematopoietic progenitors is possible if they are provided with the necessary stromal-derived growth/regulatory factors. The three-dimensional culturing system of the present invention allows for the stromal cells to maintain a subconfluent state and thus, produce the factors necessary for hematopoiesis over long time periods. However, the time period can be prolonged by further manipulations of the three-dimensional culture system.

For example, the initial marrow sample may be divided into a number of aliquots, each containing approximately $10^6$ hematopoietic cells. Each of these is inoculated onto a subconfluent stromal cell meshwork. The cultures may be monitored by direct observation with an inverted phase microscope and by differential counts of the non-adherent cells as seen on the cytospin preparation of spent media after each feeding. Prior to reaching confluency, the cultures are treated with collagenase and placed under mild ultrasonication for approximately 6–10 minutes. Hematopoietic cells and stromal cells dissociated from the culture can be fractionated by, for example, density gradient methods. The hematopoietic cells can be counted using a hemacytometer and approximately 50% cryopreserved using methods described previously. The remaining 50% of the hematopoietic cells can be divided into aliquots consisting of approximately $10^6$ cells each, and can be inoculated onto subconfluent stromal cell cultures which have been staggered and grown in parallel. When these begin to reach confluency, the same procedure may be repeated. This technique: (a) perpetuates the growth of hematopoietic cells by providing a microenvironment which produces the required growth factors and, (b) forms a continuous bank where hematopoietic progenitors may be deposited until the numbers suitable for engraftment are achieved.

6.5. Modulation of Hematopoiesis in Three-Dimensional Long-term Bone Marrow Culture The various cellular components of human marrow can be subcultured in the three-dimensional system as separate cultures. Macrophages, reticular cells, adipocytes, and fibroblasts may be grown separately and their secretory activity modified by treatment with various agents. Modulation of fibroblast activity has been described previously.

Hematopoiesis in long-term human marrow cultures on the three-dimensional meshwork may also be modulated by secretions of extramedullary macrophages (Kupffer cells) when grown in culture in the following manner. Kupffer cells can be separated from their organ stroma by, for example, pronase digestion. Briefly, tissue specimens may be incubated for 1 hour in pronase solution [0.2% pronase (Calbiochem) and Geys' Balanced Salt Solution (BSS)] while being gently agitated. The pH of the solution should be maintained at 7.3 to 7.5 using, for example, 1N NaOH. Deoxyribonuclease (0.5 mg; Calbiochem) is added at 30 minute intervals during the above procedure and the resultant cell suspension is filtered and centrifuged at 350×g for 10 minutes. The pellet may be resuspended in Geys' BSS and the littoral cells (macrophages and endothelial cells) can be separated from the cellular debris and mature blood cells using a Percoll (Pharmacia) gradient. The resultant cell fraction should be washed three time for three minutes each using, for example, a modified Dulbecco's medium enriched with 10% fetal bovine serum, and plated onto plastic culture dishes at a volume containing about 3 to $4\times10^6$ cells.

After incubation for 1 day, the non-adherent cells are removed by washing with the culture medium and the adherent cells can be maintained at 33° C. in a gas mixture consisting of about 6% $CO_2$ in room air at a relative humidity in excess of about 80%. The growth and/or secretory activity of these cells can be stimulated by: (a) varying the $CO_2$:$O_2$ ratio, (b) treating the cultures with latex beads, (c) treating the cultures with silica (d) adding prostagladin $E_2$, $E_1$ or $F_{2\alpha}$ to the medium, and, (f) supplementing the medium with interleukin 1 or interleukin 2. Macrophage secretory products may be modulated by these procedures/ agents.

The medium conditioned with the secretory products of these macrophages may be used to modulate the long-term bone marrow culture erythropoietic/granulopoietic ratio.

6.6. Uses of the Three-Dimensional Bone Marrow Culture System

6.6.1. Transplantation

The three-dimensional bone marrow cultures of the present invention may be used for treating diseases or conditions which destroy healthy bone marrow cells or depress their functional ability. The process is effective especially in the treatment of hematological malignancies and other neoplasias which metastasize to the bone marrow. This aspect of the invention is also effective in treating patients whose bone marrow has been adversely affected by environmental factors, (e.g., radiation, toxins etc.), chemotherapy and/or radiation therapy necessitated by a disease which does not directly affect the bone marrow. In these cases, for example, bone marrow cells from a healthy patient can be removed, preserved, and then replicated and reinfused should the patient develop an illness which either destroys the bone marrow directly or whose treatment adversely affects the marrow.

The three-dimensional culture system of the present invention has several advantages to a patient in need of a bone marrow transplant. If the patient is receiving his or her own cells, this is called an autologous transplant; such a transplant has little likelihood of rejection. Autologous transplants eliminate a major cause of bone marrow transplant rejection, that is, the graft vs. host reaction. If the marrow contains malignant or diseased cells, small samples it can be more effectively purged when using the three-dimensional culture system of the invention. As previously explained, selective methods for purging malignant or diseased cells would work best in small volumes of bone marrow cells. The three-dimensional culture system described herein makes this feasible. Accordingly, a small sample obtained from the patient can be more efficiently purged using a selective method that kills malignant cells yet spares healthy cells. The remaining healthy cells can then be expanded considerably using the three-dimensional culture system of the invention. In addition, the process of the present invention allows more aggressive treatment of neoplastic disorders with chemotherapeutic agents and radiation. Presently, the extent of these treatments is often limited by bone marrow toxicity.

6.6.2. Monitoring a Patient's Condition

In a patient with cancer or other diseases, it is often efficacious to monitor the patient's condition by aspirating a portion of the patient's bone marrow and examining the sample. In this manner, a metastasis or recurrence may be detected before it is clinically obvious. Patients with other conditions that are detectable by examining bone marrow cells may also be monitored in this way.

Using the three-dimensional system of the present invention, the long-term growth of cells derived from an aspirated bone marrow specimen which has not been purged enhances the likelihood of the detection of clonal metastatic cells and hematopoietic cells with chromosomal abnormalities. Such cells would be clonally expanded in the three-dimensional culture system of the invention and, thus, would be more easily detected. These cells may escape detection in a conventional smear of freshly aspirated (uncultured) bone marrow.

6.6.3. Screening Compounds

The cytotoxicity to bone marrow of pharmaceuticals, anti-neoplastic agents, carcinogens, food additives, and other substances may be tested by utilizing the in vitro bone marrow replication system of the present invention.

First, stable, growing cultures of bone marrow cells (including both stromal and hematopoietic cells) are established. Then, the cultures are exposed to varying concentrations of the test agent. After incubation with the test agents, the cultures are examined by phase microscopy to determine the highest tolerated dose (HTD)—the concentration of test agent at which the earliest morphological abnormalities appear. Cytotoxicity testing can be performed using a variety of supravital dyes assess cell viability in this three-dimensional system, using techniques well-known to those skilled in the art. The HTD determination provides a concentration range for further testing.

Once a testing range is established, varying concentrations of the test agent can be examined for their effect on viability, growth, and/or morphology of the different cell types constituting the bone marrow culture by means well known to those skilled in the art.

Similarly, the beneficial effects of drugs may be assessed using the three-dimensional culture system in vitro; for example, growth factors, hormones, drugs which enhance red blood cell formation, etc. could be tested. In this case, stable growing cultures may be exposed to the test agent. After incubation, the cultures may be examined for viability, growth, morphology, cell typing, etc. as an indication of the efficacy of the test substance. Varying concentrations of the drug may be tested to derive a dose-response curve.

Other three-dimensional cell culture systems as disclosed in the present invention may be adopted for use in cytotoxicity testing and screening drugs. An example of the use of three-dimensional bone marrow culture in cytotoxicity assays is presented in Section 18, infra.

7. THREE-DIMENSIONAL SKIN CULTURE SYSTEM

The three-dimensional culture system of the present invention provides for the replication of epidermal and dermal elements in vitro, in a system comparable to physiologic conditions. Importantly, the cells which replicate in this system segregate properly to form morphologically and histologically normal epidermal and dermal components.

The use of a three-dimensional co-cultured system for the growth of epidermal and dermal cells has many advantages over currently used monolayer systems. This model allows normal cell—cell interactions and the secretion of natural growth factors, and the establishment of a connective tissue network virtually identical to that found in vivo; in particular, the stromal cells elaborate type-specific and species-specific collagen. The resulting completely removable meshwork can be transplanted, cryopreserved, or used as a target tissue in cytotoxicity and drug mechanism studies. In addition, this model allows for the growth of fibroblasts alone to form a dermal equivalent, or of fibroblasts along with keratinocytes and melanocytes for a full-thickness skin equivalent. All the cells in this three-dimensional system remain metabolically active and undergo mitosis, a major advantage over many other models.

The three-dimensional skin culture of the invention has a variety of applications ranging from its use as a substrate for screening compounds, transplantation and skin grafting, and the study of skin diseases and treatments. For example, the need for thorough testing of chemicals of potentially toxic nature is generally recognized and the need to develop sensitive and reproducible short-term in vitro assays for the evaluation of drugs, cosmetics, food additives, and pesticides is apparent. The three-dimensional skin model described herein permits the use of a tissue-equivalent as an assay substrate and offers the advantages of normal cell interactions in a system that closely resembles the in vivo state.

The need for a skin replacement for burn patients is also evident. Several centers in the United States and Europe have utilized cultured human keratinocyte allografts and autografts to permanently cover the wounds of burns and chronic ulcers (Eisinger et al., 1980, Surgery 88:287–293; Green et al., 1979, Proc. Natl. Acad. Sci. USA 76:5665–5668; Cuono et al., 1987, Plast. Reconstr. Surg. 80:626–635). These methods are often unsuccessful and recent studies have indicated that blistering and/or skin fragility in the healed grafts may exist because of an abnormality in one or more connective tissue components formed under the transplanted epidermal layer (Woodley et al., 1988, JAMA 6:2566–2571). The three-dimensional skin culture system of the present invention provides a skin equivalent of both epidermis and dermis and should overcome problems characteristic of currently used cultured keratinocyte grafts. In addition to cytotoxicity and skin replacement, the three-dimensional skin cultures have applicability to many fields of industry including use as a model for studying skin diseases and developing new drugs and treatment modalities, and as a source of naturally secreted pharmacologic agents.

7.1. Establishment of the Three-dimensional Stromal Support and Formation of the Dermal Equivalent The inoculation of fibroblasts onto the three-dimensional matrix and their growth to subconfluence leads to the formation of a dermal equivalent. In a preferred embodiment of the invention, the fibroblasts are allowed to continue to proliferate until the entire growth substrate is covered; it should be pointed out that even after the fibroblasts have reached confluency, the fibroblasts continue to divide because the three-dimensional culture permits the exit-of cells, thereby preventing contact inhibition. Although any fibroblasts may be utilized in the inoculum, it is advantageous to use skin fibroblasts, as these will deposit the appropriate types of collagen and elaborate other dermal components. Fibroblasts may be allogeneic or autologous. Skin fibroblasts may be readily obtained from cellular suspensions prepared by mechanical and/or enzymatic disaggregation of dermal tissue. When the cellular suspension obtained is plated, the fibroblasts will adhere more quickly than other cells, and thus, can be grown to confluence, lifted by mild enzymatic treatment and inoculated onto the three-dimensional matrix as previously described.

Once inoculated onto the three-dimensional matrix, adherence of the fibroblasts is seen quickly (e.g., within hours) and the fibroblasts begin to stretch across the matrix openings within days. These fibroblasts are metabolically active, secrete extracellular matrix and rapidly form a dermal equivalent consisting of active fibroblasts and collagen. Approximately 60% confluency of the fibroblasts on the three-dimensional matrix is required to support the growth of epidermal cells later inoculated.

While the use of fibroblasts alone is sufficient to form a three-dimensional stromal matrix that functions as a dermal equivalent, additional types of stromal cells may be used to inoculate the three-dimensional matrix. These include, but are not limited to endothelial cells, pericytes, macrophages, monocytes, lymphocytes, plasma cells, adipocytes, etc.

7.2. Inoculation of the Dermal Equivalent with Epidermal Cells

In order to culture full thickness skin, i.e., comprising both an epidermal and dermal layer, epidermal cells should be inoculated onto the dermal equivalent. To this end, melanocytes and keratinocytes may be inoculated simultaneously, or preferably, in sequence. For example, keratinocytes can be inoculated onto subconfluent melanocytes which were previously inoculated onto the stromal matrix.

Melanocytes and keratinocytes may be allogeneic or autologous in their relationship to fibroblast stromal cells, can be isolated from skin using known procedures which involve incubating skin in a digestive enzyme, such as trypsin, in order to separate dermal and epidermal layers.

For example, and not by way of limitation, keratinocytes and melanocytes may be isolated as follows. A tissue sample, e.g. foreskin, may be trimmed so that the entire surface may be easily exposed to antibiotics. Tissue may be first washed in a concentrated antibiotic solution for twenty minutes, followed by two subsequent washes of ten minutes each. The outer portion of the tissue may then be cut into small pieces, and then placed in a 0.15% trypsin solution (in PBS without calcium or magnesium), quickly removed, placed in a fresh container of the same trypsin solution (such that all the tissue is covered by solution), and refrigerated overnight at about 2° C.–8° C. The next day, the tissue pieces may be removed from the trypsin solution, and the epidermis separated from the dermis using curved. forceps. The epidermis may be placed in a conical tube, and about 0.15 percent trypsin in PBS (without calcium or magnesium) may be used to digest the tissue into a single cell suspension; to facilitate this process, the sample my be repeatedly aspirated into and out of a Pasteur pipette. When the sample appears to be a single cell suspension, it may be centrifuged at 1400 g for about 7 minutes and then resuspended in either growth media or in growth media containing 0.01 mg/ml PMA, which selects for melanocytes. Accordingly, cultures of keratinocytes or melanocytes may be produced. The epidermal cells can be suspended and used to inoculate the dermal equivalent. Alternatively, the epidermal cell suspension can be plated and melanocytes and keratinocytes separated based upon their differential attachment qualities. Isolated melanocytes may first be inoculated onto the dermal equivalent and allowed to grow for a few days prior to inoculation of keratinocytes. This "tissue" grows rapidly and can be maintained in nutrient media without exogenous growth factors.

A disadvantage of all skin replacements involves the lack of hair follicles and sweat and sebaceous glands in the transplanted area. This deficiency results in the inability of the patient to regulate temperature normally and causes the patient to have severely dry skin and pant uncontrollably. To help alleviate this problem biopsies may be removed from unaffected areas of skin and implanted into the dermal equivalent. By strategically locating these biopsies follicles and associated glands may be introduced into the transplant site. Biopsies may range in size from preferably about 4 cm to 8 cm and may be removed by a standard Baker's punch. Equivalent sized biopsies may then be removed from the dermal transplant and replaced with follicle-containing implants, thereby creating a transplanted site which is histologically normal and functionally similar to normal skin.

By way of example, and not by limitation, a three-dimensional skin cell culture system may be produced as follows:

(a) fibroblasts are allowed to attach to a mesh and grow for about 7–9 days to achieve subconfluence and deposit collagen types I and III, as described previously in regard to the growth enhancing fibroblast used in the in vitro bone marrow replication system;

(b) melanocytes are plated onto the stromal mesh and are allowed to grow to subconfluence for about 5 days;

(c) keratinocytes are inoculated onto subconfluent melanocytes.

In a preferred embodiment of the invention, a three-dimensional skin cell culture system may be produced as follows:

(a) fibroblasts are allowed to attach to a mesh and grow for about 14 days to achieve confluence and deposit collagen types I and III;

(b) melanocytes are plated onto the stromal mesh and are allowed to grow to subconfluence for about 5 days; and (c) keratinocytes are inoculated onto subconfluent melanocytes.

In particular embodiments of the invention, for example, and not by way of limitation, in burn patients, it may be advantageous to provide a covering for the wound shortly after injury; in such a situation a three-dimensional cell culture according to the invention consisting largely of fibroblasts and corresponding to the dermis (and hitherto referred to as the neodermis) may be placed over the wound, and melanocytes and keratinocytes may subsequently be applied. The neodermis may comprise cells autologous or allogeneic to the patient. Epidermal cells may be allogeneic or, preferably, autologous to the patient. The present invention includes the implantation of a living, growing neodermis to which epidermal cells may be added in vivo or in vitro; alternatively, a patient's own cells may be allowed to populate the transplanted neodermis.

7.3 Morphological Characterization of Three-dimensional Skin Culture

Figure 1:
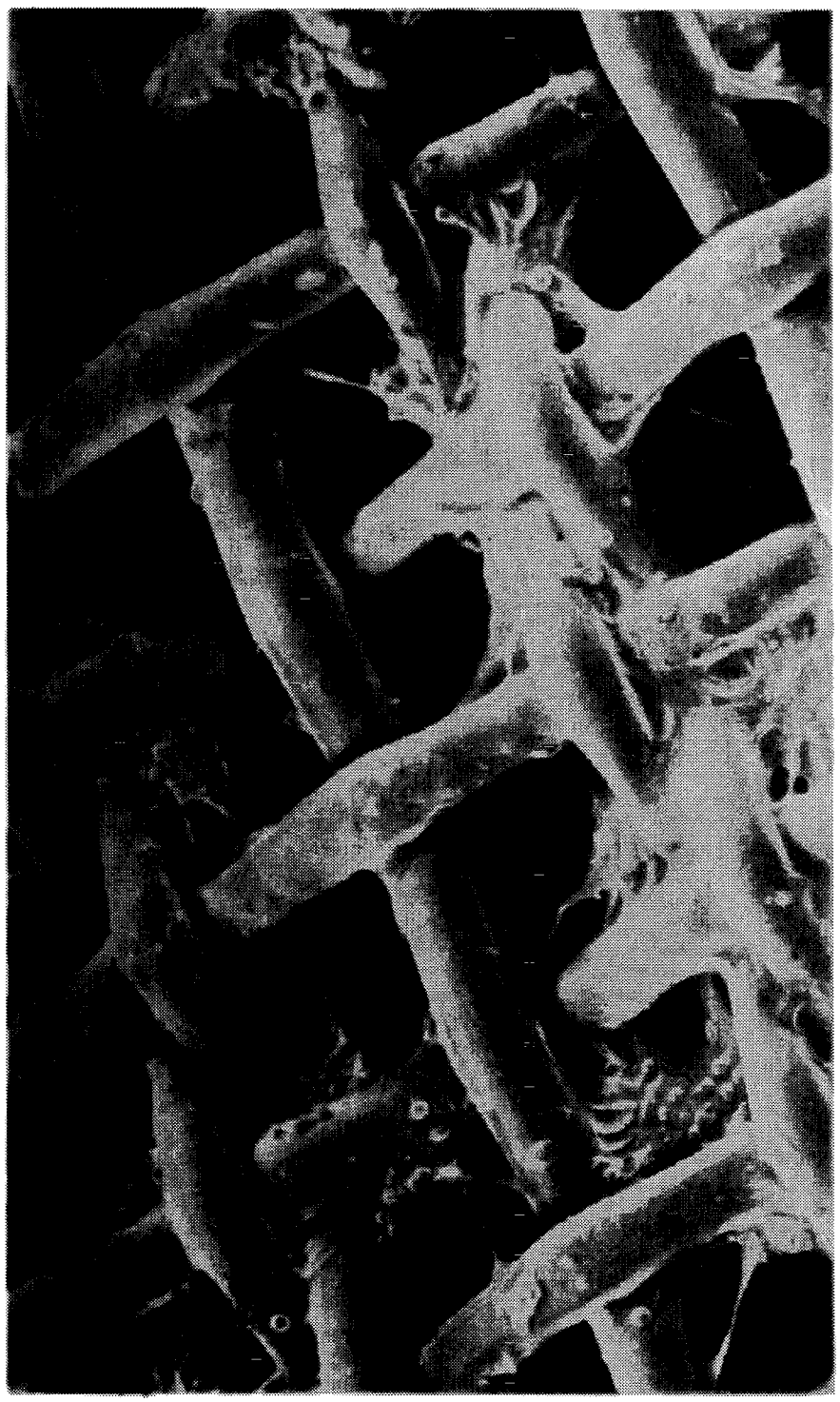
FIG. 1 is a scanning electron micrograph depicting fibroblast attachment to the three-dimensional matrix and extension of cellular processes across the mesh opening. Fibroblasts are actively secreting matrix proteins and are at the appropriate stage of subconfluency which should be obtained prior to inoculation with tissue-specific cells.

Morphological characterization of the three-dimensional stroma indicate that the fibroblasts inoculated onto the matrix stretch across the openings, exhibit matrix deposition, and migrate into the interstices of the mesh. FIG. 1 illustrates the ability of the fibroblasts to arrange themselves into parallel layers between the naturally-secreted collagen bundles. These fibroblasts exhibit a rapid rate of cell division and protein secretion. Melanocytes will grow normally in the three-dimensional system in that they exhibit dendrite formation, remain pigmented and retain the ability to transfer pigment (see FIGS. 6 through 8).

Full thickness skin can be grown in a variety of ways allowing an air interface. Exposure of the keratinocytes to air promotes a more rapid differentiation of keratinocytes and more extensive secretion of keratin layers, which may be very important in skin penetration studies.

A major advantage of this cell culturing system over others currently employed in dermatological research and engraftment studies is that the fibroblasts in the three dimensional matrix, either subconfluent or confluent, as described supra, remain metabolically active and secrete natural growth factors and naturally occurring collagen types I and III. The normal metabolic activity of these cells makes this system particularly advantageous for use in cytotoxicity assays as well as in the study of disorders which affect collagen secretion directly, or in which an interplay between dermal and epidermal cells results in pathological alterations consistent with the disease.

7.4. Transplantation in Vivo

For purposes of transplantation or engraftment it is preferable to use three-dimensional matrices constructed of biodegradable materials, e.g., catgut suture, gelatin, etc. These permit all the advantages of a three-dimensional system but allow a transplanted "tissue" to remain intact while the mesh is naturally degraded and absorbed by the body and replaced by normal cells migrating into the area.

To form the three-dimensional stromal matrix, it would be preferable to utilize skin fibroblasts obtained from the patient who is to receive the graft. Alternatively, fetal fibroblasts or a mixture of fetal fibroblasts and the patient's fibroblasts may be used. However, according to the invention, fibroblasts from autologous, allogeneic, or xenogeneic source may be used; Example Section 19 illustrates a specific embodiment of the invention in which human fibroblasts are cultured according to the invention, implanted and successfully grafted into pig. More importantly, however, the later inoculated epidermal cells may be advantageously derived from the patient in order to minimize the risk of rejection of the graft.

In an alternate embodiment of this aspect of the invention, the three-dimensional stromal support matrix which forms the neodermis can itself be engrafted onto the patient's wound. In this instance, the patient's own epidermal cells in the wound area will invade the stromal matrix and proliferate on the stromal matrix in vivo to form full thickness skin, i.e., both epidermal and dermal layers. Alternatively, epidermal cells may be seeded onto the neodermis, or sheets of epidermal cells may be applied. Where large wound areas are to be covered, it may be preferred to engraft the complete three-dimensional skin culture, or to use combinations of both neodermis and full-thickness skin cultures. For example, neodermis could be engrafted at the edges of the wound, and full thickness cultures in central areas of the wound, to enhance growth and healing and minimize scar formation.

7.5 In Vitro Uses of the Three-dimensional Skin Culture

The three-dimensional skin cultures can be maintained in vitro and used for a variety of purposes, including screening compounds for toxicity, the study of the mechanism of drug action, the study of skin disorders and disease, etc.

The three-dimensional skin culture could be used as a substrate to test the cytotoxicity of compounds and other substances. For example, for use in cytotoxicity assays, human cells could be grown onto meshes which could be cut into 6 mm disks, places into 96-well flat bottom tissue culture microtest plates, and fed with appropriate medium. The test substance could then be added to each sample. The test substance could be advantageously applied by limiting dilution technique, in which case, a range of concentrations of the toxic substance can be tested. Each tissue type may be represented by three rows of meshes in order to provide data in triplicate. A properly controlled assay could be run as follows: mesh alone; mesh inoculated with fibroblasts; mesh inoculated with fibroblasts and keratinocytes; mesh with fibroblasts and melanocytes; and mesh inoculated with fibroblasts, melanocytes and keratinocytes. Chemical agents can be added to each of these substrates and incubated, e.g. for 24 hours. The cytotoxic effect of such substances can be evaluated in a number of ways. For example, a convenient method, the well known neutral red assay, could be adapted for use in this system. To this end, after removal of the medium, each well may be rinsed before adding a 0.4% aqueous stock solution of neutral red dye. After various time intervals the dye is removed and cells are rapidly washed with 4.0% formaldehyde, 1.0% $CaCl_2$. After about 20 minutes, the amount of dye present in each tissue sample can be measured by reading absorbance with a Dynatech microplate reader equipped with a 540 nm filter. The amount of vital dye absorbed is directly proportional to the number of viable cells present in each well. The readings can be averaged and the results expressed as absorbance observed over baseline levels in control cultures.

Recent studies have indicated that the skin is an integral and active element of the immune system (Cooper et al., 1987, The mechanobullous diseases. In: Dermatology in General Medicine, 3d. Ed., McGraw Hill, N.Y., pp.610–626). One of the major cells in the skin which is responsible for various immune activities is the Langerhans cell. These cells may be prepared from fresh skin samples and added to the three-dimensional skin culture to produce an immunologically complete tissue system. Growth of these cells in the culture for 10 ng periods of time by conventional tissue culture techniques is difficult. The ability to grow these cells in a three-dimensional system would be of great importance in all aspects of study including engraftment, cytotoxicity, and disease mechanisms. This type of skin culture system would have the greatest N impact on research involving auto-immune disorders which have direct or indirect cutaneous involvement (lupus erythematosis, bullous pemphigoid, etc.).

As explained previously, the three-dimensional skin culture could also be used to test for sensitivity to allergens. For allergy tests, the skin cultures could be inoculated with lymphocytes (or plasma cells) and mast cells derived from a patient. Exposure of the culture to an allergen which "bridges" IgE antibodies (produced by the lymphocytes) bound to resident mast cells would result in in the release of vasoactive mediators such as histamine by the mast cells. The release of histamine in the culture could be measured and correlated with the person's allergic response to the test allergen.

8. THREE-DIMENSIONAL LIVER TISSUE CULTURE SYSTEM

Hepatocytes may be isolated by conventional methods (Berry and Friend, 1969, J. Cell Biol. 43:506–520) which can be adapted for human liver biopsy or autopsy material. Briefly, a canula is introduced into the portal vein or a portal branch and the liver is perfused with calcium-free or magnesium-free buffer until the tissue appears pale. The organ is then perfused with a proteolytic enzyme such as a collagenase solution at an adequate flow rate. This should digest the connective tissue framework. The liver is then washed in buffer and the cells are dispersed. The cell suspension may be filtered through a 70 μm nylon mesh to remove debris. Hepatocytes may be selected from the cell suspension by two or three differential centrifugations.

For perfusion of individual lobes of excised human liver, HEPES buffer may be used. Perfusion of collagenase in HEPES buffer may be accomplished at the rate of about 30 ml/minute. A single cell suspension is obtained by further incubation with collagenase for 15–20 minutes at 37° C. (Guguen-Guillouzo and Guillouzo, eds, 1986, "Isolated and Culture Hepatocytes" Paris, INSERM, and London, John Libbey Eurotext, pp. 1–12; 1982, Cell Biol. Int. Rep. 6:625–628).

The isolated hepatocytes may then be used to inoculate the three dimensional stroma. The inoculated stroma can be cultured as described for bone-marrow and skin in order to replicate the hepatocytes in vitro, in a system comparable to physiologic conditions. This should result in an increased functional expression by the hepatocytes.

Liver cultures maintained in this fashion may be utilized for a variety of purposes including cytotocity testing, screening drugs, etc. In one embodiment, three-dimensional liver cultures could be used to screen for carcinogens and mutagens in vitro. More particularly, it is well known that a number of compounds fail to act as mutagens in test organisms such as bacteria or fungi, yet cause tumors in experimental animals such as mice. This is due to metabolic activation; i.e., some chemicals are metabolically altered by enzymes in the liver (the P450 oxidase system and hydroxylation systems) or other tissues, creating new compounds that are both mutagenic and carcinogenic. In order to identify such carcinogens, Ames and his co-workers devised a screening assay which involves incubating the chemical compound with liver extracts prior to exposure of the test organism to the metabolic product (Ames et al., 1975, Mut. Res. 31:347–364). While a more sophisticated approach, the Ames assay still lacks sensitivity. By contrast, the three-dimensional liver cultures can be utilized both as the metabolic converters and the "test organism" to determine the mutagenicity or carcinogenicity of the substance being tested.

9. THREE-DIMENSIONAL MODEL SYSTEM FOR THE BLOOD-BRAIN BARRIER

According to the invetnion, a three-dimensional tissue culture model system for the blood-brain barrier may be produced. Briefly, this three-dimensional culture recreates the endothelial cell barrier which separates the central nervous system from the bloodstream by first growing endothelial cells derived from small blood vessels of the brain to confluence in a three-dimensional mesh. First astrocytes, and then neurons, are applied to the confluent stromal matrix formed by endothelial cells such that the endothelial cells form a barrier between one surface of the culture, above, and the neurons, below. A substance applied to the endothelial cell surface must penetrate through the endothelial cell layer to reach the neurons beneath.

For example, and not by way of limitation, endothelial cells may be isolated from small blood vessels of the brain according to the method of Larson et al. (1987, Microvasc. Res. 34:184) and their numbers expanded by culturing in vitro using standard methods. These small vessel endothelial cells may then be inoculated onto a suitable mesh (e.g. the nylon filtration screen made by Tetko, Inc., #3-210/36) and then grown to complete confluence; silver staining may be used to ascertain the presence of tight junctional complexes specific to small vessel endothelium and associated with the "barrier" function of the endothelium.

Neurons and astrocytes may then be obtained from embryonic or perinatal rats and then separated one from the other using standard techniques (Hattan et al., 1988, J. Cell Biol. 106: . For example, neurons may be separated from astrocytes by differential adherence to a substrate, astrocytes adhering to dishes precoated with 100 μg/ml poly-D-lysine, and neurons adhering to dishes precoated with 500 μg/ml poly-D-lysine.

Astrocytes may then be inoculated onto confluent endothelial cell three-dimensional stromal matrices, cultured for a period of about 5 days and then further inoculated with neuronal cells.

The multi-layer three-dimensional tissue culture system comprises one layer of small blood vessel endothelial cells and another of astrocytes and neurons, and recreates the structure of the blood-brain barrier found in vivo, wherein substances in the blood must penetrate the endothelium of small blood vessels to reach the neuronal tissue of the brain. The system can be used to test the ability of substances to cross the blood-brain barrier. Because many substances are unable to cross this barrier, there is a long felt need for an in vitro system to rapidly screen the penetration abilities of test agents. For example, many antibiotics are unable to cross the blood-brain barrier. It would be useful to be able to rapidly screen newly developed antibotics for their penetration ability; the relatively few antibiotics which may be used to treat central nervous system infections, many of which are related to penicillin and therefore associated with the risk of allergic reaction, creates an urgent need for the development of new CNS-active agents.

10. THREE-DIMENSIONAL PANCREAS TISSUE CULTURE SYSTEM

Suspensions of pancreatic acinar cells may be prepared by an adaptation of techniques described by others (Ruoff and Hay, 1979, Cell Tissue Res. 204:243–252; and Hay, 1979, in, "Methodological Surveys in Biochemistry. Vol. 8, Cell Populations." London, Ellis Hornwood, Ltd., pp.143–160). Briefly, the tissue is minced and washed in calcium-free, magnesium-free buffer. The minced tissue fragments are incubated in a solution of trypsin and collagenase. Dissociated cells may be filtered using a 20 μm nylon mesh, resuspended in a suitable buffer such as Hanks balanced salt solution, and pelleted by centrifugation. The resulting pellet of cells can be resuspended in minimal amounts of appropriate media and inoculated onto the three-dimensinal stroma prepared as previously described. Acinar cells can be identified on the basis of zymogen droplet inclusions. The culture of pancreatic acinar cells in the three-dimensional stromal system should prolong cell survival in culture.

11. EXAMPLE: THREE-DIMENSIONAL BONE MARROW CULTURE SYSTEM

The subsections below demonstrate that the three-dimensional culture system can be used for the establishment of long term bone marrow cultures for human, non-human primate (macaque), and rat. The three-dimensional cultures were evaluated by scanning electron microscopy, and the cellular content was evaluated by a number of methods. The progenitor content was evaluated by CFU-C and BFU-E, and the cellular content by differential counts and cytofluorographic analysis using labeled monoclonal antibodies specific for different hematopoietic cell lines.

The results indicate that the three-dimensional culture system supports the expression of several hematologic lineages as evidenced by the differential counts of the non-adherent and adherent zones of the human, macaque and rat cells. Cytofluorographic analysis of the cells attached to the three-dimensional stroma, i.e., the adherent zone, revealed the presence of early and late myeloid precursors, mature granulocytes, B and T lymphocytes, megakaryocytes/platelets, and monocytes/macrophages. Although the number of progenitor cells located in the matrix was variable, this may have resulted from the random populations of stromal cells used to form the support matrix.

Since hematopoiesis may be dependent on growth-related activities and factors produced by the support cells, the three-dimensional cultures were grown in flasks which also contained a confluent monolayer of stromal cells. An inhibition of both hematopoiesis and stromal cell growth in the three-dimensional culture system was observed in the presence of confluent stromal cells; i.e., the confluent monolayer of stromal cells in the flask appears to "shut off" the three-dimensional culture system. When the three-dimensional culture was transferred to a new flask, recovery of hematopoiesis was observed. This result suggests that stromal cell products influence not only hematopoietic cells, but other stromal elements as well.

The methods, results and data are described in more detail in the subsections below.

11.1. Preparation of Bone Marrow Samples

11.1.1. Human Bone Marrow

Bone marrow was aspirated from multiple sites on the posterior iliac crest of hematologically normal adult volunteers after informed consent was obtained. Specimens were collected into heparinized tubes and suspended in 8 ml of RPMI 1640 medium which was conditioned with 10% FBS and 5–10% HS and supplemented with hydrocortisone, fungizone, and streptomycin. The cell clumps were disaggregated and divided into aliquots of $5\times10^6$ nucleated cells.

11.1.2. Non-human Primate Bone Marrow

Intact cynomolgus macaque monkey femurs were purchased from the Charles River Primate Center (Porter Washington, N.Y.). The epiphyseal ends of the femurs were separated from the bone shaft under sterile conditions. The red marrow was removed, suspended in medium, and divided into aliquots of $5\times10^6$ nucleated cells.

11.1.2. Non-human Primate Bone Marrow

Adult male Long-Evans rats (225–400 gm) were anesthetized with ether, and after removal of their femurs, were exsanguinated from the abdominal aorta using heparinized syringes. The femurs were split and the marrow contents were scraped into a sterile petri dish containing 3 ml of Fischer's medium (Gibco, N.Y.) conditioned with 10% FBS and 10% HS and supplemented with hydrocortisone, fungizone, heparin, and antibiotics (Naughton et al., 1987, J. Med. 18:219–250). Aliquots of $5-7\times10^6$ cells were prepared.

11.2. Establishment of the Three-dimensional Stromal Matrix

Nylon filtration screen (#3-210/36, Tetko Inc., N.Y.) was used as a template to suport all LTBMC described in the examples below. The screen consisted of fibers, which were 90 μm in diameter, assembled into a square weave pattern with sieve openings of 210 μm. Stromal cells were inoculated using the protocols described in the subsections below. Adherence and subsequent growth of the stromal elements was monitored using inverted phase contrast microscopy and scanning electron microscopy (SEM).

11.2.1. Preparation of the Screen and Inoculation of Stromal Cells for Human LTBMC 8 mm×45 mm pieces of screen were soaked in 0.1M acetic acid for 30 minutes and treated with 10 mM polylysine suspension for 1 hour to enhance attachment of support cells. These were placed-in a sterile petri dish and inoculated with either $5\times10^6$ human bone marrow cells or with equal numbers of human fetal fibroblasts (#GM 1380, Coriell Institute, N.Y.). Human fetal fibroblasts were grown to confluence in monolayers using RPMI 1540 medium conditioned with 10% FBS, 5–10% HS, supplemented with hydrocortisone, fungizone, and streptomycin, at 35° C., 5% $CO_2$, and a relative humidity in excess of 90%. These cells were lifted using collagenase (10 μg/ml for 15 minutes) and transferred onto the screen. After 1–2 hours of incubation at 5% $CO_2$ the screens were placed in a Corning 25 cm² culture flask and floated with an additional 5 ml of medium. Screens inoculated with marrow stromal cells were transferred in a similar manner.

11.2.2. Preparation of the Screen and Inoculation of Stromal Cells for Non-human Primate LTBMC Two matrices were employed for LTBMC of monkey cells: nylon mesh inoculated with human fetal fibroblasts (as described above) and nylon mesh that was inoculated with $5\times10^6$ femoral marrow cells from a cynomolgus macaque. Culture conditions and screen pretreatment protocols were identical to those used for the human cultures described above.

11.2.3. Preparation of the Screen and Inoculation of Stromal Cells for Rat LTBMC 8 mm×45 mm pieces of nylon screen were soaked in 0.1M acetic acid for 30 minutes and coated with solubilized type IV mouse collagen (GIBCO Labs, N.Y.) for 1–2 hours. The screen was inoculated with $5-7\times10^6$ Long-Evans rat femoral marrow cells and after 1–2 hours of incubation in 5% $CO_2$ at 33° C., the mesh was transferred to a 25 cm² culture flask. 5 ml of medium was added to float the screen.

11.3. Inoculation of Three-dimensional Stromal Matrix with Hematopoietic Cells and Establishment of Culture When approximately 70% of the mesh openings were bridged with support cells (10–14 days for rat stroma, 7–13 days for human or monkey stroma, and 4–7 days for human fetal fibroblasts), the screens were transferred to sterile petri dishes and inoculated with $5 \times 10^6$ human or monkey nucleated bone marrow cells or $2–5 \times 10^6$ rat femoral marrow cells, respectively. After 2 hours of incubation in 5% $CO_2$ each screen was gently floated in a 25 cm$^2$ Corning flask to which 5 ml of medium was added. Cultures were fed every 5 days by replacement of the spent media with fresh media. The culture vessels were also checked for the appearance of cell monolayers on the walls of the vessels. If such monolayers were present at a confluency greater than 25%, the three-dimensional cultures were transferred to new flasks.

11.4. Evaluation of Three-dimensional Bone Marrow Culture

The growth of the bone marrow cells and the cell content of the three-dimensional cultures were assayed histologically, by differential counts, CFU-C and BFU-E analysis, and cytofluorographic analysis as described below.

11.4.1. Histological Evaluation

For electron microscopic study, cultures were sacrificed at various intervals following the first inoculation of stromal cells and the second inoculation of hematopoietic cells. Briefly, nylon screens were cut into approximately 4 equal parts and were fixed in 3% gluteraldehyde phosphate buffer solution, washed, dehydrated in acetone, and placed in a Denton Critical Point Dryer. In some instances, the stromal layer was physically disrupted to permit the visualization of the underlying cell growth (Naughton et al., 1987, J. Med. 18:219–250). Specimens were coated with 60% gold and 40% palladium and studied with an Amray SEM.

Figure 2:
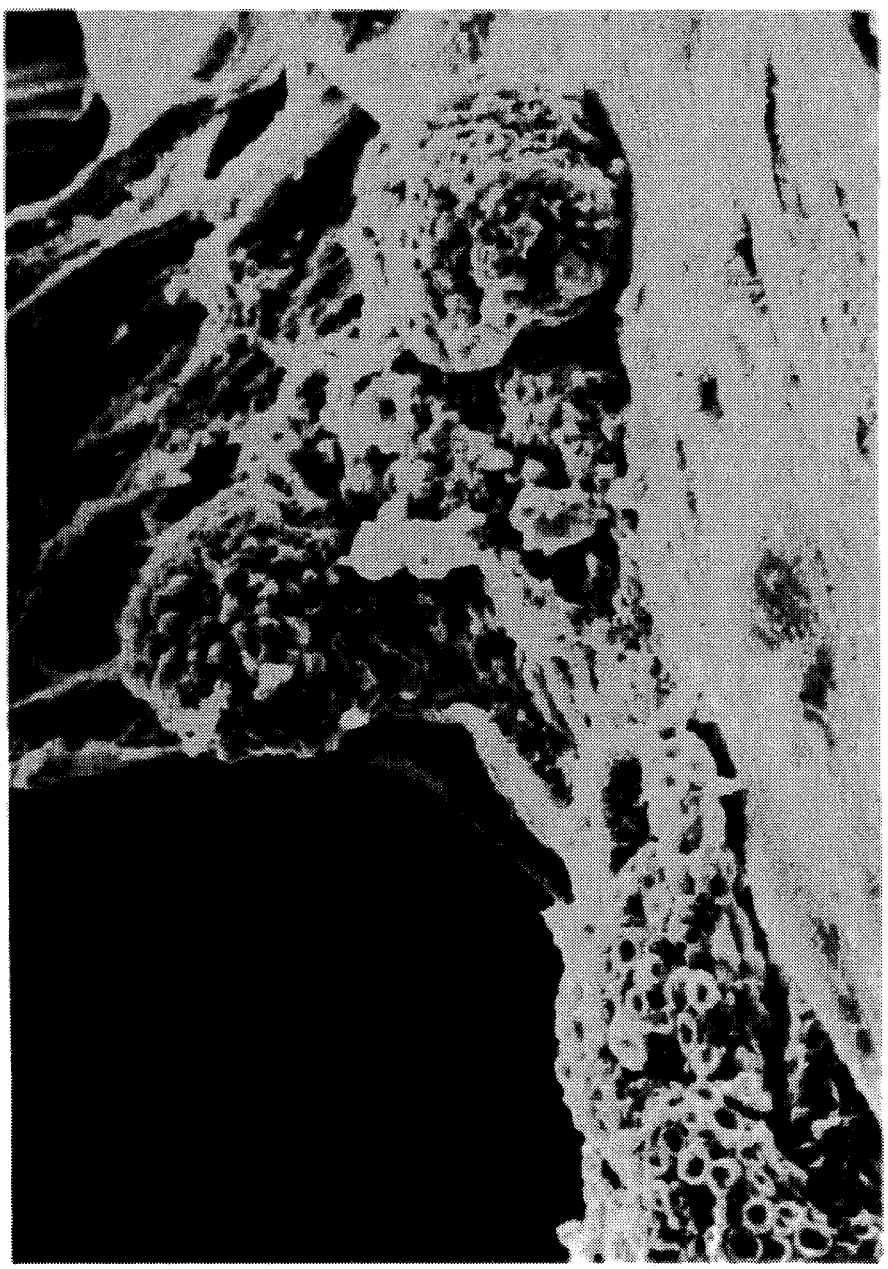
FIG. 2 is a scanning electron micrograph of the three-dimensional LTBMC demonstrating the 210 µm sieve area for expression of erythroid, myeloid and other colonies. Support cells have grown linearly along and enveloped the three-dimensional matrix.

The growth pattern of human and macaque cells in the three-dimensional LTBMC was similar to that for rat bone marrow. Briefly, stromal cells (either marrow-derived or fetal human fibroblasts) grew linearly along and enveloped each nylon strand before starting to span the mesh openings (FIG. 1). Hematopoietic (and stromal) cells of the second inoculum seed in the natural interstices formed by the stromal cell processes which are present in at least 70% of the openings in the 3.6 cm$^2$ mesh (FIG. 2). Hematopoietic cells did not appear to bind directly to the nylon but, rather, to those areas where support cells were attached. Colonization was evident in all cultures by 3–6 days after the second inoculation of hematopoietic cells. The 210 μm sieve provided sufficient area for the expression of erythroid, myeloid and other colonies (FIG. 2) Hematopoiesis was observed on the outer surfaces of the nylon screen LTBMC but was most extensive in the interstices of the developing support cells.

11.4.2. Total Cell Counts and Cytospin Analysis of Spent Medium of Three-dimensional LTBMC Total cell counts and cytospin preparations were made using spent medium removed when the cultures were fed (every 5 days). Cell counts were performed using the hemacytometer method. Cytospins were stained with Wright's-Giemsa and differential counts were performed on random fields. Analysis of cytospin slides prepared after each feeding revealed the presence of late stage precursors of the erythroid, myeloid, and lymphoid lineages in the human and monkey cultures (Table II). These persisted for the term of culture of each species tested (39 weeks for the rat, 12.5 weeks for the primates) although the relative percentages of the cell types varied. Macrophages/monocytes/fibroblasts released into the non-adherent zone of the human cultures increased with time, mainly at the expense of the myeloid cells (Table II).

TABLE II

CELLULAR CONTENT OF THE NON-ADHERENT ZONE*

| Time in culture (wk) | Differential Count (%) | | | | |
|---|---|---|---|---|---|
| | MY | E | L | MAC/STR | Other |
| HUMAN | | | | | |
| 0 | 63.9 | 19.0 | 10.8 | 3.6 | 2.7 |
| 1 | 59.0 | 14.0 | 8.6 | 14.9 | 3.5 |
| 2 | 48.5 | 14.4 | 9.9 | 23.7 | 3.9 |
| 3 | 51.9 | 9.2 | 9.6 | 24.7 | 4.6 |
| 4 | 41.2 | 10.4 | 6.1 | 33.9 | 8.4 |
| 5 | 41.9 | 12.7 | 10.3 | 29.0 | 6.1 |
| 6 | 45.2 | 11.2 | 8.0 | 27.2 | 8.4 |
| 7 | 39.8 | 10.1 | 6.3 | 34.8 | 9.0 |
| 8 | 38.6 | 9.8 | 6.5 | 37.1 | 8.0 |
| 9 | 40.3 | 5.6 | 6.6 | 38.4 | 9.1 |
| 10 | 35.9 | 5.5 | 6.8 | 40.6 | 11.2 |
| 11 | 31.3 | 6.7 | 5.4 | 43.2 | 13.4 |
| 12 | 30.1 | 5.0 | 4.1 | 44.6 | 16.2 |
| MACAQUES | | | | | |
| 0 | 64.8 | 14.2 | 10.1 | 8.2 | 2.7 |
| 1 | 60.2 | 16.0 | 6.8 | 12.9 | 4.1 |
| 2 | 57.4 | 14.9 | 7.5 | 16.4 | 3.8 |
| 3 | 49.7 | 12.4 | 10.0 | 23.5 | 4.4 |
| 4 | 49.7 | 9.9 | 7.9 | 26.2 | 6.3 |
| 5 | 43.0 | 10.7 | 6.1 | 32.0 | 8.2 |
| 6 | 39.2 | 8.0 | 6.0 | 36.7 | 10.1 |
| 7 | ND | ND | ND | ND | ND |
| 8 | 38.8 | 4.3 | 8.4 | 39.2 | 9.8 |
| 9 | 27.6 | 7.7 | 8.6 | 46.1 | 10.0 |
| 10 | 35.5 | 6.2 | 7.7 | 42.0 | 10.6 |
| 11 | ND | ND | ND | ND | ND |
| 12 | 35.4 | 6.0 | 6.9 | 39.2 | 12.5 |

*Results reflect an average of 3–5 cultures. Each culture contained one 3.6 cm$^2$ nylon screen.
MY = myeloid, E = erythroid, L = lymphoid, MAC/STR = macrophages, monocytes, and fibroblastic cells, Other = megakaryocytes, unidentified blasts.
ND = not done.

11.4.3. Total Cell Counts and Cytospin Analysis of Adherent Zone of Three-Dimensional LTBMC Cell counts of the adherent zone were done at different intervals of LTBMC by treating the screen with a 1:1 mixture of collagenase and trypsin (10 μg/ml) and mild ultrasonication. Such analysis of the adherent zone of human and cynomolgus macaque LTBMC revealed that the relative percentage of stromal cells to hematopoietic cells increased with time in culture (Table III). In particular, as hematopoietic colonization proceeded, the relative percentage of stromal elements dropped. However, stromal cell growth at later periods of the LTBMC occurs at the expense of hematopoiesis.

TABLE III

CELLULAR CONTENT OF THE ADHERENT ZONE
HUMAN

| Time in culture (wk) | Differential Count (%) | | | |
|---|---|---|---|---|
| | Stromal | E | MY | Other |
| 1 | 66.4 | 6.2 | 20.4 | 7.0 |
| 2 | 60.0 | 5.4 | 26.4 | 8.2 |
| 3 | 54.2 | 6.6 | 29.2 | 10.0 |
| 4 | 62.6 | 6.8 | 24.5 | 6.1 |
| 5 | 65.1 | 2.7 | 25.2 | 7.0 |
| 6 | 65.4 | 6.1 | 21.6 | 6.9 |
| 7 | 59.7 | 7.7 | 25.4 | 7.2 |
| 8 | 64.3 | 5.1 | 24.0 | 6.6 |
| 9 | 72.9 | 2.7 | 18.4 | 6.0 |
| 10 | 73.2 | 3.7 | 17.7 | 5.4 |
| 11 | 71.3 | 3.0 | 19.6 | 6.1 |
| 12 | 74.7 | 2.9 | 17.4 | 5.0 |

MACAQUES

| Time in culture (wk) | Differential Count (%) | | | |
|---|---|---|---|---|
| | Stromal | E | MY | Other |
| 1 | 53.1 | 8.0 | 35.7 | 3.2 |
| 2 | 66.0 | 8.3 | 19.2 | 6.5 |
| 3 | 68.6 | 7.4 | 18.1 | 5.9 |
| 4 | 57.0 | 5.1 | 29.2 | 8.7 |
| 5 | 56.6 | 5.8 | 27.5 | 10.1 |
| 6 | 63.1 | 3.9 | 24.0 | 9.0 |
| 7 | ND | ND | ND | ND |
| 8 | 68.1 | 4.8 | 20.2 | 6.9 |
| 9 | 59.3 | 4.0 | 27.3 | 9.4 |
| 10 | 70.0 | 4.4 | 17.3 | 8.3 |
| 11 | ND | ND | ND | ND |
| 12 | 65.3 | 4.2 | 21.9 | 8.6 |

Cells of the adherent zone were disaggregated by enzyme treatment.
Stroma includes fibroblasts, macrophages, adipocyte-like cells, endothelia; E = erythroid; MY = myeloid; Other = lymphoid, thromboid, unidentified blasts.
ND = not done.

Cellular proliferation achieved a steady state condition after several weeks in culture; similar numbers of cells were found in the adherent and nonadherent zones when the LTBMC were examined on a weekly basis (FIG. 3). The numbers of cells in the non-adherent zone for the first 1–2 weeks of culture were somewhat misleading. In our experience, many of the cells which appear in the medium in the early stages of culture were formerly loosley attached to the matrix. These become detached easily causing an artifically high cell count for the non-adherent zone. Likewise, because of relatively low seeding efficiency, only $5 \times 10^5$ to $10^6$ cells initially adhere to the mesh even though the inoculation volume was $5 \times 10^6$ cells. This "hides" the 2–3 fold cellular proliferation which occurs on the mesh during the first week of culture.

11.4.4. CFU-C and BFU-E Content of Adherent Zone of Three-dimensional LTBMC

The CFU-C content of the adherent zone of rat LTBMC was determined using a modification of the method of Bradley and Metclaf (1966, Austr. J. Exptl. Biol. Med. Sci. 44:287–300). Briefly, $4 \times 10^4$ cells were plated and incubatd at 37° C. in 7–7.5% $CO_2$. Pokeweed mitogen rat spleen cell conditioned medium was utilized as a source of colony stimulating activity (CSA) for rat CFU-C which were counted after 14 days in culture. Human CFU-C were determined by aliquoting $10^5$ nucleated cells/ml in Iscove's Modified Dulbecco's medium supplemented with 20% FBS and plating over a layer of $10^6$ PBLs in 0.5% agar (Griffin et al., 1981, J. Clin. Invest. 68:932). Colonies were scored on days 7 and 14 after plating (37° C., 7% $CO_2$). Human BFU-E were assayed after various intervals of LTBMC in 0.8% methylcellulose in Iscove's medium containing 30% FBS, 1% bovine serum albumin, $10^{-4}$M mercaptoethanol, 2.5–5 I.U./ml of partially purified human urinary erythropoietin (Naughton et al., 1985, J. Surg. Oncol. 30:184–197), and 4.5% of phytohemagglutinin-stimulated human leukocyte conditioned medium (Cashman et al., 1983, Blood 61:876–884).

Substantial numbers of CFU-C were recovered from the adherent zone of the rat and human LTBMC relative to those present in the initial inoculum (FIG. 4). Preliminary findings indicate that BFU-E persisted in the human LTBMC as well (Table IV).

TABLE IV

BFU-E IN THE ADHERENT ZONE AT VARIOUS INTERVALS OF LTBMC

| Time of culture (wk) | Numbers of BFU-E* |
|---|---|
| uncultured marrow | 19 ± 6 |
| 2 | 14 ± 4 |
| 4 | 12 ± 5 |
| 7 | 8 ± 3 |
| 9 | 11 ± 6 |
| 10 | 8 ± 3 |

*Colonies per $10^5$ cells; mean of 3–4 plates ± SEM

11.4.5. Cytofluorographic Analysis of Cellular Content of Adherent Zone of Three-dimensional LTBMC Cytofluorographic analysis of the cellular content of the adherent zones of human and monkey LTBMC was performed using the EPICS system (Coulter Electronics, Hialeah, Fla.). Cells were separated from the nylon screen at various intervals after the inoculation of hematopoietic cells using collagenase and trypsin followed by extensive washing. Then cells were incubated for 45–60 minutes in Hank's Balanced Salt Solution with $Ca^{++}$ or $Mg^{++}$. These were reacted with the following monclonal antibodies-which were conjugated to fluorescein isothiocyanate (FITC): Mo-1, T-3, B-1, Plt-1, and MY-9 (Coulter Immunology, Fla.). Murine IgM-FITC-treated cells were used as controls. Sorting windows were chosen on the basis of fluorescence and light scatter histograms. A 0.255 window was appropriately gated and the cellular profiles were determined.

Cytofluorographic analysis of adherent zones of the human cultures at 2, 7 and 10.5 weeks confirmed the presence of early (MY-9) and late (Mo-1) myeloid cells, B (B-1) and T (T-3) lymphocytes, megakaryocytes/platelets (Plt-1), and monocytes/macrophages (Mo-1) (Table V).

TABLE V

MEAN PERCENT REACTIVITY OF
UNCULTURED BONE MARROW AND CELLS FROM
THREE-DIMENSIONAL LTBMC WITH MONOCLONAL ANTIBODIES[a]

| | Human[b] | | | |
|---|---|---|---|---|
| MAb | 2 wk LTBMC | 7 wk LTBMC | 10.5 wk LTBMC | Uncultured |
| B-1 | 10.20 ± 1.43 | 6.76 ± 0.98 | 22.73 ± 1.37 | 11.96 ± 1.13 |
| T-3 | 18.64 ± 1.88 | 11.18 ± 1.86 | 13.01 ± 1.84 | 9.90 ± 0.64 |
| Plt-1 | 4.40 ± 1.33 | 8.08 ± 0.92 | 17.05 ± 4.10 | 8.724 ± 1.83 |
| Mo-1 | 10.10 ± 1.04 | 17.26 ± 2.29 | 20.98 ± 1.14 | 3.46 ± 0.25 |
| My-9 | 3.98 ± 0.26 | 3.70 ± 0.68 | 3.46 ± 0.25 | 1.46 ± 0.54 |

| | Macaque[c] | |
|---|---|---|
| MAb | 7 wk LTBMC | Uncultured |
| B-1 | 31.01 | 8.37 ± 0.99 |
| T-3 | 18.13 | 11.56 ± 2.1 |
| Plt-1 | 46.50 | 8.53 ± 1.09 |
| Mo-1 | 40.87 | 26.64 ± 2.25 |
| My-9 | 21.64 | 5.49 ± 0.83 |

[a]Mean percent reactivity was calculated by subtracting non-specific labeling with murine-IgM-FITC control. MAb = monoclonal antibody.
[b]Results reflect data from 4–5 cultures (±1 SE). Times listed are following the inoculation of tissue-specific cells.
[c]Mean of 2 cultures inoculated onto fetal human fibroblasts.

Human and monkey LTBMC can be established on a stratum of fetal human fibroblasts but this matrix will not support the growth of rat LTBMC. The fetal fibroblast cells reach a stage of subconfluence which will allow the subsequent inoculation of marrow cells much sooner than marrow stroma. When macaque bone marrow is grown on a bed of fetal fibroblasts, the phenotypic profile of the adherent zone shows that more cells react with the Plt-1 antibody than in the other cultures we studied but the other hematologic lineages are represented also (Table V). It is not known to what extent this finding reflects cross-reactivity of the antibody or a shift in the cell population of the adherent zone mediated by the fetal cells.

11.4.6. The Effect of Confluent Stromal Cell Monolayers on Cell growth in Three-dimensional Cultures Femoral marrow cells from Long-Evans rats or cynomolgus macaque were poured through a packed Fenwal wool column as described by Boswell and co-workers (Boswell et al., 1987, Exptl. Hematol. 15:46–53). Briefly, $10^7$–$10^8$ femoral marrow cells were placed in 4 ml of medium and poured over a nylon wool column which was pre-incubated at 37° C. for 45 minutes in medium. After an additional 45 minutes of incubation, the non-adherent cells were drained and the adherent cells were removed by extensive washing and elution with EDTA-Versene solution (1:5000 in saline; GIBCO, Grand Island, N.Y.). Approximately $10^7$ cells were inoculated in parallel into 25 cm² flasks and grown to 50% and 100% confluence. Pre-established nylon screen LTBMC which were standardized with respect to time following the second inoculation, were inserted into each flask. Growth on the nylon screen LTBMC and the monolayer was observed microscopically. Cell counts and cytospin of the nonadherent zone were performed every 5 days. Differential counts of cytospin preparations of the enzyme dissociated adherent cells were performed 5 days after insertion of the nylon screen LTBMC.

When confluent stromal cell monolayers are co-cultured with nylon screen LTBMC, both hematopoiesis and stromal cell growth on the suspended culture are inhibited (Table VI) as compared to LTBMC suspended in flasks without adherent stroma (p less than 0.05) or with stromal cells at approximately 50% confluence (p less than 0.05). In addition, co-culture with confluent stromal monolayers causes the detachment and release of mesh-associated stromal cells into the non-adherent zone. Hematopoietic colonies coalesce and cease growing. If the LTBMC is transferred to a new flask, recovery of hematopoiesis is seen by 3–5 days.

TABLE VI

EFFECT OF STROMAL MONOLAYERS AT
APPROXIMATELY 50% AND 100% CONFLUENCE ON
CELLULAR PROLIFERATION IN A SUSPENDED
NYLON SCREEN LTBMC IN THE RAT

| | Time of Exposure[b] | MONOLAYER EFFECT ON CELL PROLIFERATION[a] | |
|---|---|---|---|
| Cells | (days) | 50% Confluent | 100% Confluent |
| Stromal Cells[c] | 7 | 0 ± 2.5 | −13.5 ± 4.7 |
| | 15 | +3.3 ± 2.0 | −18.0 ± 5.1 |
| | 28 | +1.7 ± 0.9 | −24.3 ± 4.0 |
| Hematopoietic[d] Cells | 7 | −1.0 ± 4.1 | −17.3 ± 3.2 |
| | 15 | +6.3 ± 3.4 | −30.8 ± 7.7 |
| | 28 | +2.7 ± 1.9 | −49.9 ± 10.2 |

[a]Results are expressed as mean percent differences (+/−) ± 1 SEM as compared to LTBMC grown in the absence of adherent cells on the bottom of the flask. Nylon screen bone marrow cultures were tested at 2 weeks following the second inoculation (with hematopoietic cells).
[b]Time after introduction of the nylon screen LTBMC into a flask containing adherent cells at either approximately 50% or 100% confluence.
[c]Includes fibroblast, macrophages, adipocyte-like cells, endothelia.
[d]Includes blasts and late stage precursors of all lineages.

12. EXAMPLE: THREE-DIMENSIONAL SKIN CULTURE SYSTEM

The subsections below describe the three-dimensional culture system of the invention for culturing skin in vitro. Briefly, cultures of fibroblasts were established on nylon mesh which had been previously sterilized within 6–9 days of incubation, adherent fibroblasts began to grow into the meshwork openings and deposited parallel bundles of collagen. Indirect immunofluorescence using monoclonal antibodies showed predominantly type I collagen with some type III as well. After 7 days, co-cultures of human melanocytes and kertinocytes were plated onto the fibroblast meshwork. No TPA or cholera toxin was added since trophic factors are produced by the subconfluent fibroblasts of the adherent layer. Electron microscopic studies revealed skin cells with normal morphological characteristics and cell—cell attachments.

12.1. Establishment of the Three-dimensional Stroma

Skin fibroblasts were isolated by mincing of dermal tissue, trypsinization for 2 hours, and separation of cells into a suspension by physical means. Fibroblasts were grown to confluency in 25 cm$^2$ Falcon tissue culture dishes and fed with RPMI 1640 (Sigma, Mo.) supplemented with 10% fetal bovine serum (FBS), fungizone, gentamycin, and penicillin/streptomycin. Fibroblasts were lifted by mild trypsinization and cells were plated onto nylon filtration mesh, the fibers of which are approximately 90 µm in diameter and are assembled into a square weave with a mesh opening of 210 µm (Tetko, Inc., N.Y.). The mesh was pretreated with a mild acid wash and incubated in polylysine and FBS. Adherence of the fibroblasts was seen within 3 hours, and fibroblasts began to stretch across the mesh openings within 5–7 days of initial inoculation. These fibroblasts were metabolically active, secreted an extracellular matrix, and rapidly formed a dermal equivalent consisting of active fibroblasts and collagen. FIG. 1 is a scanning electron micrograph depicting fibroblast attachment and extension of cellular processes across the mesh opening.

12.2. Inoculation of Melanocytes and Keratinocytes

Melanocytes were isolated according to the method of Eisinger and Marko (1982, Proc. Natl. Acad. Sci. USA 79:2018–2022). Briefly, skin samples were incubated in trypsin for 4–6 hours, allowing separation of the epidermal and dermal layers. Epidermal cells were suspended in media and plated into 25 cm$^2$ Falcon tissue culture flasks. Melanocytes were separated from keratinocytes by preferential attachment qualities. Isolated melanocytes were plated onto the fibroblast-coated nylon mesh and allowed to grow for 3 days prior to the addition of keratinocytes. Melanocytes grow normally in this system in that they exhibit dendrite formation, remain pigmented, and retain the ability to transfer pigment to keratinocytes. FIG. 6 depicts the appearance of melanocytes after 3 days in the three-dimensional culture system. Isolated keratinocytes were plated onto the melanocytes after 3–4 days. This "tissue" grows rapidly and is maintained in RPMI 1640, 10% FBS, and the appropriate antibiotics. Since natural growth factors are secreted by the dermal elements, no addition of exogenous factors (e.g., TPA, cholera toxins, etc., as described by Sengel, 1983, in Biochemistry and Physiology of Skin, Vol. 1, pp. 102–131, Oxford Univ. Press, N.Y.; and Eisinger et al., 1988, Proc. Natl. Acad. Sci. USA 85:1937–1941), is necessary.

12.3. Histological Analysis of Skin Culture

The skin cultures were evaluated histologically by light microscopy using the following procedure: all tissue was fixed in 2.5% buffered gluteraldehyde, dehydrated in ethanol, and cleared in xylene prior to paraffin embedding. Sections were cut at a thickness of 6 to 8 µm, stained with hematoxylin-eosin and examined for normal and altered morphological characteristics.

A cross section of this skin model is shown in the photomicrographs of FIGS. 7 and 8. Normal cell orientation and morphology is obvious. Epidermal and dermal components completely surround the mesh fiber and a distinct dermal-epidermal junction is evident (FIG. 7). Keratinocytes manifest a normal morphology and contain pigment granules, and a maturation of cells is seen, with evidence of the formation of a stratum corneum (FIG. 8).

12.4. Transplantation of Three-dimensional Skin Culture in Vivo

Our transplantation studies in rats have indicated that this three-dimensional system permits the rapid engraftment of the dermal and epidermal components without rejection.

Twenty four rats were employed in the skin transplantation studies. Meshes were cut into 6 mm circular pieces, autoclaved, treated with mild acid, incubated with collagen type IV, incubated with fetal bovine serum and inoculated with stromal cells with or without a second inoculation of keratinocytes. Meshes covered with dermal and/or epidermal cell components were sutured into wound areas and closely examined every 12–24 hours as follows: rats received light ether anesthesia and their dorsal surfaces were shaved and washed with a betadine solution. Four 6 mm punches were made with a disposable Baker's punch biospy needle, and sub-cuticular suturing was used to hold the implanted meshes in place. The rats were closely examined until 12 hours post surgery and then monitored every 24 hours.

The areas of mesh implantation showed no signs of erythema, swelling, exudate, or fragility. Meshes were removed at 7 days, 14 days, and 21 days post transplantation. Results of these transplants are illustrated in FIGS. 9 and 10. All skin cells are shown 7 days post transplant (FIG. 9). FIG. 10 illustrates keratinocytes (k), fibroblasts (f), collagen (c), adipocytes (a) and smooth muscle cells (s) all arranged in a natural configuration around the nylon mesh fiber (m). The absence of lymphocytes and other immune components along with the strong natural attachment of the cells to the mesh indicates that no rejection is taking place in vivo.

Parallel studies have been performed in which meshes with dermal and epidermal components were implanted into 10 mm×10 mm skin biopsies which were then maintained in culture for 14 days and examined histologically. Similar cell migration, attachment, and differentiation patterns were observed in these in vitro transplants. The engraftment studies to date help to substantiate the hypothesis that our three-dimensional matrix system is a true physiologic system in which all cell components are activated and natural growth factors are being produced.

Although the invention is described in detail with reference to specific embodiments thereof, it will be understood that variations can be made without departing from the scope of the invention as described above and as claimed below.

13. EXAMPLE: THREE-DIMENSIONAL LIVER CULTURE SYSTEM

13.1. Materials and Methods

13.1.1. Anesthesia

An adult Long-Evans rat weighing approximately 300 gm. was injected intraperitoneally with 0.3 ml of injectable sodium pentbarbital.

13.1.2. Dissection

The animal was pinched with a sharp forceps to ensure adequate anesthetization. A midline incision was made between the xiphoid process and the inguinal area, followed by further incisions to produce flaps permitting entrance to the abdominal cavity. The intestines and other organs were pushed to the right side of the animal, exposing the hepatic portal vein. The hepatic portal vein was further exposed by dissection and a 4.0 suture was tied around the hepatic portal vein distal to where the catheter was to be placed. A second suture was placed around the hepatic portal vein proximal to where the catheter was to be placed. A small nick was made in the hepatic portal vein with a 21 gauge needle. The peristaltic pump was turned on and infusion of 500 ml of HEPES buffer (containing 4.1 gm NaCl, 0.25 gm KCl, 3 ml of 1M NaOH, and 10 ml of 0.24% w/v HEPES stock) was begun; immediately thereafter the inferior vena cava was cut to allow for the buffer to escape. After infusion was complete, the pump was shut off, and the liver was gently removed into a Buckner funnel and then perfused with collagenase solution (0.4 gm NaCl, 0.05g KCP, 10 ml HEPES stock (supra), 0.07 gm $CaCl_2.2H_2O$, 6.6 ml 1M NaOH, 50 mg collagenase in 100 cc, brought to a pH of 7.6 at 37° C.). Perfusion was allowed to continue for 15–20 minutes. The contents of the Buckner funnel were filtered, and the liver was removed and placed in collagenase solution containing 1.5% (w/v) BSA.

13.1.3. Cell Solution Preparation

The lobes of the perfused liver were separated, and the outer parenchyma trimmed away. The inner parenchyma was then minced in Hanks balanced salt solution (HBSS) containing physiologic Ca++ and Mg++. Large liver tissue fragments were allowed to settle out, and the cell suspension was then centrifuged through a Percoll gradient (5 ml of DMEM plus 0.5 Iu/ml insulin, 0.007 mg/ml glucagon and 20 percent fetal bovine serum) was placed in a 50 ml conical centrifuge tube, HBSS plus physiological Ca++ and Mg++ was added to the 50 ml. mark, and 5 ml. of Percoll working solution [70% stock Percoll plus 30% PBS; stock Percoll was 9 parts Percoll and 1 part 10× concentrated Dulbecco's medium] was layered on top of the HBSS by centrifugation at 800 g for 10 minutes. Liver parenchyma cells were collected from the bottom of the gradient and added to three-dimensional mesh cultures with subconfluent stroma.

13.1.4. Preparation of Three-Dimensional Stromal Matrix 8 mm×45 mm pieces of nylon filtrating screen (#3-210/36, Tetko, Inc., N.Y.) were soaked in 0.1M acetic acid for 30 minutes and treated with 10 mM polylysine suspension for 1 hour. The meshes were placed in a sterile petri dish and inoculated with $1\times10^6$ fibroblasts collected from rat liver in DMEM complete medium. After 1–2 hours of incubation at 5% $CO_2$ the screens were placed in a Corning 25 $cm^2$ tissue culture flask, floated with an additional 5 ml. of medium, and allowed to reach subconfluence, being fed at 3 day intervals.

13.1.5. Maintenance of Three-dimensional Liver Tissue Cultures

After inoculation of liver parenchymal cells onto the three-dimensional stromal matrix, cultures were maintained in DMEM complete medium at 37° C. and 5% $CO_2$ in a humidified atmosphere and were fed with fresh medium every 3 days.

13.2. Results and Discussion

Adult liver cells cultured in this fashion exhibited active mitosis and continued to secrete proteins over a three-week period of time. Hepatocytes oriented themselves into cords of cells (FIG. 11 and histologically resembled hepatoblasts or regenerating liver cells during the first 10–12 days of three-dimensional culture (FIG. 12). As the cultures became highly confluent, the parenchymal cells began to resemble mature adult hepatocytes with bile duct cells, Kupffer cells and other liver stromal cells still present. Cells divided approximately every 24 hours for the first 10–12 days of culture and continued to divide every 72 hours for up to a three-week period. Albumin secretion continued over the three-week culture period and hepatocyte retained their activated enzymes which allowed them to metabolize products in vitro. After cultures reached full confluency they could be maintained as viable substrates for up to 12 weeks.

14. EXAMPLE: THREE-DIMENSIONAL MUCOSAL EPITHELIUM TISSUE CULTURE SYSTEM

14.1. Materials and Methods

14.1.1. Preparation of Mucosal Epithelial Cells

Samples of oral mucosal tissue were obtained from orthodontic surgical specimens. Tissue was washed three times with fresh MEM containing antibiotics (2 ml of antibiotic antimycotic solution, from GIBCO, Cat. #600-5240 AG; and 0.01 ml of gentamycin solution from GIBCO, Cat. #600-5710 AD per 100 cc MEM), cut into small pieces, then washed with 0.02% EDTA (w/v). 0.25% trypsin (in PBS without Ca++ or Mg++ was added; after a few seconds, the tissue pieces were removed and placed in fresh 0.25% trypsin (in PBS without Ca++ or Mg++) and refrigerated at 4° C. overnight. Tissues were then removed and placed in fresh trypsin solution, and gently aggitated until cells appeared to form a single-cell suspension. The single-cell suspension was then diluted in MEM containing 10% heat-inactivated fetal bovine serum and centifuged at 1400 g for 7 minutes. The supernatant was decanted and the pellet containing mucosal epithelial cells was placed into seeding medium. Medium consisted of DMEM with 2% Ultrosen G, 1×L-glutamine, 1×nonessential amino acids, penicillin and streptomycin. The cells were then seeded onto a three-dimensional stromal matrix (see infra).

14.1.2. Preparation of the Three-Dimensional Stromal Matrix

The three-dimensional stromal matrix used in mucosal epithelium cultures was generated using oral fibroblasts and 8 mm×45 mm pieces of nylon filtration screeen (#3-210/36, Tetko Inc., N.Y.) as described above for three-dimensional liver cultures in Section 13.1.4).

14.1.3. Maintenance of Three-dimensional Mucosal Epithelium Tissue Cultures After inoculation of mucosal epithelial cells onto the three-dimensional stromal matrix, cultures were maintained in DMEM complete medium at 37° and 5% $CO_2$ in a humidified atmosphere and were fed with fresh medium every 3 days.

14.2. Results and Discussion

FIG. 13 is a photomicrograph of a cross-section of a three-dimensional mucosal epithelium tissue culture produced by the methods described supra. The tissue culture was found to recapitulate the stratified squamous epithelium of the oral mucosa in vivo; note that as the cells approach the surface of the culture, the nuclei become flattened and oriented in a plane parallel to the surface, as occurs in vivo.

15. EXAMPLE: THREE-DIMENSIONAL PANCREAS TISSUE CULTURE SYSTEM

15.1. Materials and Methods

15.1.1. Preparation of Pancreatic Acinar Cells

Pancreatic acinar cells were prepared by an adaptation of the technique described in Ruoff and Hay (1979, Cell Tissue Res. 204:243–252) and Hay (1979 in "Methodological Surveys in Biochemistry", Vol. 8, "Cell Populations," London, Ellis Hornwood, Ltd. pp. 143–160). The tissue was collected from adult male Long-Evans rats and minced and washed in calcium free, magnesium free HBSS buffer. The minced tissue was then incubated in a solution containing 0.25 percent rypsin and collagenase. Dissociated cells were filtered using a 20 μm nylon mesh, resuspended in HBSS, and pelleted by centrifugation at 300 g for 15 minutes. The resulting pellet was resuspended in a small amount of DMEM complete medium and inoculated onto three-dimensional stroma (see infra).

15.1.2. Preparation of the Three-dimensional Stromal Matrix

The three-dimensional stromal matrix used in pancreatic tissue cultures was generated using adult rat pancreatic fibroblasts and 8 mm×45 mm pieces of nylon filtration screen (#3-210/36, Tetko, Inc., N.Y.) as described above for three-dimensional liver cultures in Section 13.1.4.

15.1.3. Maintenance of Three-dimensional Pancreatic Tissue Cultures

After inoculation of pancreatic acinar cells onto the three-dimensional stromal matrix, cultures were maintained in DMEM complete medium at 37° C. and 5% $CO_2$ in a humidified atmosphere and were fed with fresh medium every 3 days.

15.2. Results and Discussion

FIG. 14 is a photomicrograph of a cross-section of a three-dimensional pancreas tissue culture produced by the methods described supra. The tissue culture acinar cells may be identified on the basis of zymogen droplet inclusions [arrow], as compared to the more homogeneous appearance of stromal cells (asterisk). Islet cells remain concentrated in the center of each mesh opening and form a structure containing 1–2×10$^5$ insulin-secreting cells.

16. EXAMPLE: THREE-DIMENSIONAL MODEL SYSTEM FOR THE BLOOD-BRAIN BARRIER

16.1. Materials and Methods

16.1.1. Preparation of Small Vessel Endothelial Cells

Small vessel endothelial cells isolated from the brain according to the method of Larson et al. (1987, Microvasc. Res. 34:184) were cultured in vitro using T-75 tissue culture flasks. The cells were maintained in Dulbecco's Modified Eagle Medium/Hams-F-12 medium combination (the solution is available as a 1:1 mixture). The medium was supplemented with 20% heat-inactivated fetal calf serum (FCS), glutamine, and antibiotics. The cells were seeded at a concentration of 1×10$^6$ cells per flask, and reached a confluent state within one week. The cells were passaged once a week, and, in addition, were fed once a week with DMEM/Hams-F-12 containing FCS, glutamine, and antibiotics as described supra. To passage the cells, flasks were rinsed twice with 5 ml of PBS (without Ca++ or Mg++) and trypsinized with 3 ml of 0.05% Trypsin and 0.53 mM EDTA. The cells were pelleted, resuspended, and tested for viability by trypan blue exclusion, seeded and fed with 25 ml of the abovementioned DMEM/Hams-F-12 supplemented medium. A factor VIII related antigen assay (Grulnick et al., 1977, Ann. Int. Med. 86:598–616) is used to positively identify endothelial cells, and silver staining was used to identify tight junctional complexes, specific to only small vessel endothelium.

16.1.2. Preparation and Seeding of Mesh

Nylon filtration screen mesh (#3-210/36, Tetko, Inc., N.Y.) was prepared essentially as described above for liver, pancreas, bone marrow, etc. tissue culture systems. The mesh was soaked in an acetic acid solution (1 ml glacial acetic acid plus 99 ml distilled $H_2O$) for thirty minutes, was rinsed with copius amounts of distilled water and then autoclaved. Meshes were coated with 6 ml fetal bovine serum per 8×8 cm mesh and incubated overnight. The meshes were then stacked, three high, and 3×10$^7$ small vessel endothelial cells (cultured as described supra) were seeded onto the stack, and incubated for three hours at 37° C. under 5% $CO_2$ in a humidified atmosphere. The inoculated meshes were fed with 10 ml of DMEM/Hams-F-12 medium every 3–4 days until complete confluence was reached (in approximately two weeks).

16.1.3. Preparation of Neuron and Astrocyte Cell Populations

Neurons and astrocytes were isolated from fetal rat cerebellum. The cerebellums from 5 rats were dissected out and placed in PBS buffer. The PBS was then removed and 1 ml of trypsin solution (10 mg trypsin, 1 ml PBS with 0.01 g $MgSO_4$-$7H_2O$, and 6 μl 1N NaOH) was added to each. After 3 minutes, the tissue was rinsed with about 1 ml PBS buffer and 2 ml of a stock solution consisting of 7.5 mg DNAse plus 15 ml Earles BME). Individual cells were then brought into suspension by aspirating tissue through progressively smaller syringe needles ranging from 18 to 25 gauge, until the solution was cloudy. The resulting single-cell suspension was then centrifuged at 800 g for 5 minutes, and the cell pellet resuspended in medium and then passed through a 33 μm filter. Cells were then layered onto a 60%/35% Percoll step gradient and centrifuged for 10 min. at 800 g. Cells at the 0%/35% interface were mostly glia and astrocytes; cells at the 35%/60% interface were largely neurons. Both populations were collected and diluted separately in 5 ml of PBS, washed, and collected by centrifugation at 2500 g for 5 minutes. The cells were then resuspended in medium (BME containing 10% heat-inactivated horse serum). Both cell types were, separately, plated onto culture dishes precoated with poly-D-lysine. First they were plated onto dishes precoated with 100 μg poly-D-lysine, incubated for 20–45 minutes, and then lightly rinsed with PBS; glia and astrocytes selectively adhered to the culture dishes, and neurons were rinsed off. The rinse buffer was then plated onto culture dishes coated with 500 μg poly-D-lysine, in which case neurons adhered to the culture dishes.

16.1.4. Seeding the Astrocytes onto Three-dimensional Endothelial Cell Cultures $5 \times 10^5$ astrocytes were seeded onto meshes covered with confluent endothelial cells (described supra) by removing the medium from the mesh, inoculating the meshes with the astrocytes, and then incubating for one hour at 37° C. and 5% $CO_2$ in a humidified atmosphere. The mesh was then fed with DMEM-k12 containing interferon, transferrin, selenium, and subsequently fed at 2–3 day intervals.

16.1.5. Seeding Neurons onto Three-dimensional Endothelial Cell-astrocyte Tissue Cultures After approximately 5 days, neurons were seeded onto the endothelial cell-astrocyte tissue cultures. Neuronal cell cultures, exhibiting neurite outgrowth (which was obseved after about one week in culture), were harvested and approximately $5 \times 10^5$ cells were seeded onto the endothelial cell/ astrocyte three-dimensional culture meshes. Neuronal cells were seeded in a minimal volume of culture medium, and then incubated for 3 hours at 37° C. and 5% $CO_2$ in a humidified atmosphere, after which time meshes were fed with a standard volume of DMEM/F12, reincubated, and subsequently fed at 2–3 day intervals.

16.2. Results and Discussion

Nylon mesh was precoated with fetal bovine serum, onto which small vessel endothelial cells, grown to confluence in standard monolayer culture, were seeded and grown to complete confluence.

Neurons and astrocytes were prepared from the cerebellum of fetal rats, and separated by differential adherence. Astrocytes were grown on the confluent endothelial cell three-dimensional stromal matrix, and, subsequently, neuronal cells were added to the three-dimensional tissue culture.

The resulting endothelial cell/astrocyte/neuron three-dimensional tissue culture, was then maintained until it reached a second stage of semi-confluence covering the layer of endothelial cells. This multi-layer three-dimensional tissue culture system, as shown in FIG. 15, wherin one layer consists of confluent small blood vessel endothelial cells and the other layer consists of astsrocytes and neurons, recreates the structure of the blood-brain barrier found in vivo, wherein substances in the blood must penetrate the endothelium of small blood vessels to reach the neuronal tissue of the brain. Such a blood-brain barrier model system can be used to study the passage, or lack thereof, of chemicals or viruses into the brain; it is advantageous to determine which antibiotics, or antivirals for example, can penetrate the blood-brain barrier to treat central nervous system infections. Further, such a model system can be used as a substrate for athe study of the action and potency of various neurotoxins.

17. EXAMPLE: THREE-DIMENSIONAL ADENOCARCINOMA TISSUE CULTURE SYSTEM

17.1. Materials and Methods

17.1.1. Preparation of Adenocarcinoma Stromal and Parenchymal Cells

Adenocarcinoma cells were separated from stromal cells by mincing tumor cells in HBSS, incubating the cells in 0.27% trypsin for 24 hours at 37° C. and further incubating suspended cells in DMEM complete medium on a plastic petri dish for 12 hours at 37° C. Stromal cells selectively adhered to the plastic dishes.

17.1.2. Preparation of the Three-dimensional Stromal Matrix

The three-dimensional stromal matrix used in adenocarcinoma tissue cultures was generated using stromal cells derived from the tumor (see Section 17.1.1., supra) and 8 mm×45 mm pieces of nylon filtration screen (#3-210/36, Tetko, Inc., N.Y.), as described above for three-dimensional liver cultures in Section 13.1.4.

17.1.3. Maintenance of Three-dimensional Adenocarcinoma Tissue Cultures

After inoculation of adenocarcinoma cells onto the three-dimensional tumor stromal matrix, cultures were maintained in DMEM complete medium with high glucose, 15% FBC and 0.03% glutamine at 37° C. and 5% $CO_2$ in a humidified atmosphere and were fed with fresh medium every 3 days.

17.2. Results and Discussion

FIG. 16 is a photomicrograph of a three-dimensional adenocarcinoma tissue culture. Adenocarcinoma cells showed a characteristic piling and orientation into a three-dimensional tumor-like structure. Cells retained their epithelial-like appearance.

18. EXAMPLE: THREE-DIMENSIONAL TISSUE CULTURE CYTOXICITY TESTING SYSTEM

18.1. Materials and Methods

18.1.1. Preparation of Three-dimensional Bone Marrow Tissue Cultures

Three-dimensional bone marrow tissue cultures were prepared according to the method outlined in Section 11, supra.

18.1.2. Exposure of Three-dimensional Bone Marrow Cultures to Cytotoxic Agents Individual three-dimensional bone marrow cultures were maintained in each well of a 96 well tissue-culture tray for cytotoxicity testing.

Cultures were exposed to 10-fold serial dilutions of adriamycin, ranging from 0.1 TO 10 μm, for 24 hours. Controls were exposed to ten-fold serial dilutions of bovine serum albumin (BSA).

Similarly, other three-dimensional bone marrow cultures, in a 96 well multi-well tissue culture unit, were exposed to ten-fold serial dilutions of cis-platinum, ranging from 1–75 μm for 24 hours. Controls were exposed to serial dilutions of BSA.

In all cases, monolayers of human fibroblasts, cultured using conventional techniques, were compared to three-dimensional cultures of either stromal cells alone, or in conjunction with hematopoietic cells.

18.1.3. Cytotoxicity Assay

Media was removed from cells, and 0.2 ml of neutral red dye-media solution (see Section 18.1.4, infra) was added to each well. The cultures were then incubated at 37° C. for three hours. In culture trays containing three-dimensional cultures, well 1A served as the control and contained mesh alone without cells.

After incubation, dye/medium was removed, and each well was washed rapidly with formal-calcium (see 18.1.4, infra) to remove unincorporated neutral red and enhance attachment of the cells to the substratum.

0.2 ml of acetic acid/ethanol solution (see 18.1.4, infra) was added to each well and the cultures were kept at room temperature for 15 minutes (to extract the dye) and then shaken for a few seconds on a shaker plate.

Culture trays were then transferred to a Dynatech microplate reader equipped with a 540 nm filter for automated spectrophotometric reading and recording. Acetic acid/ethanol solution in a control well served as a blank.

18.1.4. Solutions for Cytotoxicity Assay

Neutral red/medium was prepared as follows. Neutral red was prepared as a 0.4% aqueous stock solution and was shielded from light by foil. A fresh 1:80 dilution of the dye was made. Immediately before use, the dye medium solution was centrifuged for 5 minutes at 1500 g and the supernatant fluid was used for the neutral red assay.

Formal-calcium was prepared as follows. 5 g of CaCl (anhydrous) was added to 497.5 ml of sterile distilled $H_2O$. 2.5 ml of 40% formaldehyde was then added to produce a formal-calcium solution which was 1% $caCl_2$ and 0.5% formalin.

Acetic acid ethanol solution was produced as follows. 1.09 ml glacial acetic acid was added to 99 ml of 50% ethanol.

Adriamycin and cis-platinum were obtained from Sigma Chemical Co., St. Louis, Mo.

18.2. Results and Discussion

FIGS. 17 and 18 show the results of three-dimensional bone marrow culture cytotoxicity assays, using adriamycin and cis-platinum, respectively, as test agents. Note that, in each case, the three-dimensional culture systems show a dose-related response to test agent. Significantly, with either adriamycin or cis-platinum, the $TD_{50}$ for bone marrow three-dimensional cultures was different from the $TD_{50}$ determined using conventional fibroblast monolayer cultures. Importantly, these results indicate that monolayer cultures may not be accurate measures for cytotoxicity; perhaps because the cells are growing in an extremely unnatural environment, monolayer cell cultures may be more sensitive to toxic agents. It is crucial to be able to determine the actual toxicity of a test substance; for example, in chemotherapy, it may be important to administer the highest dose tolerable in order to effectively eliminate malignant cells. Underestimating the highest tolerated dose may result in administering a less effective amount of anti-tumor agent. By providing three-dimensional tissue cultures not only of bone marrow and other normal tissues, but tumor tissues as well, the present invention enables the in vitro determination of the optimal dose of chemotherapeutic agent.

19. EXAMPLE: THREE-DIMENSIONAL SKIN CULTURE SYSTEM FOR IMPLANTATION USING A NEODERMIS IN MICROPIGS

Skin transplants were performed on four Charles River micropigs. Experiments were designed to compare the effects of neodermis, mesh substrate permeated with cell lysate, and mesh alone on the contraction, healing and epithelialization of split-thickness and full-thickness wounds. Multiple parallel wounds were compared along the dorsal surface of each animal to allow accurate assessment of healing in each area. In these studies a biodegradable mesh was seeded with pig dermal fibroblasts and transplanted as a dermal replacement. Other meshes included human dermal fibroblasts and pig dermal fibroblasts seeded with pig keratinocytes. By monitoring the engrafted areas through histological sections and gross changes in appearance (exudate, erythema, etc.), we were able to study th efficacy of the three-dimensional skin system as a transplant modality.

19.1. Materials and Methods

19.1.1. Preparation of the Wound Bed

For proper evaluation of the epidermal graft it was essential that the wound graft bed be prepared so that no dermis, hair follicles, sweat or sebaceous glands remained. To achieve this, a Browne dermatome at a setting of 0.075–0.090 inch was used to remove full thickness skin from the upper lateral side of the pig. Wound areas of 5 cm×5 cm were created. When lower lateral regions were to be prepared, the setting was adjusted to 0.60–0.075 inches. The mesh alone or mesh with cultured cells was placed on the bed, just above the fascia. The sterile dermatome-prepared bed reduced the possibility of contamination and allowed for absolute hemostasis in the graft bed.

If minor bleeding occurred after the skin removal, a dry gauze dressing was placed on the wound and pressure was applied for 10–15 minutes. At all times the sterile bed was covered with sterile gauze pre-wetted with PBS until the grafts were placed on the fascia. Silk sutures (3–0) were placed approximately one and one-half inches apart on both sides of the prepared graft bed to hold a compression stent in place. Cultured grafts (meshes with cells) were removed from tissue culture flasks with sterile forceps and sutured into place using conventional subcuticular stitches. Grafts were covered with petrolatum gauze and silk ligatures were tied so as to provide a compression stent. The pig was bandaged with Elastoplast. Wound dressings were changed in four days.

19.1.2. Anesthesia

Pigs were anesthetized with the use of ketamine hydrochloride (Ketalar) and were kept under anesthesia by a mixture of halothane, nitrous oxide, and oxygen. The skin area was washed with povidone-iodine (Betadine) and 7% alcohol, prior to preparation of four full-thickness graft beds on the lateral side of the pig, as described above.

19.1.3. Animal Maintenance

After 4 to 5 days the wound dressing was removed, grafted areas were studied for signs of infection and/or rejection, and then were covered once more with petrolatum gauze and bandaged with Elastoplast. Wounds were subsequently observed at four-day intervals with biopsies being taken from treated areas. Animals were anesthetized with Ketalar to allow sterile removal of a 4 mm biopsy utilizing a disposable Baker's punch and sterile technique. Samples were sent for histological evaluation in order to assess graft attachment and wound healing.

19.1.4. Epithelial Grafts

Selected animals received half-grafts of autologous keratinocytes 10 days after implantation with the dermal equivalent. Keratinocyte sheets produced from isolated cells grown to over-confluence had been cultured for 10–14 days before implantation onto the dermal equivalent. Sheets were attached by four topical sutures and covered with petrolatum gauze and bandaging to allow cell attachment.

19.2. Results

In all animals treated, dermal equivalents attached well, prevented contraction and dehydration, and provided a living tissue bed onto which epithelial cells could migrate or be placed in an autologous transplant. FIG. 19 is a representative of healing 10 days after implantation of human dermal equivalent (neodermis) into a full thickness wound. We noted a minimal contraction of the area and no signs of rejection, indicating the utility of allogenic fibroblasts in transplants. Histological evaluation of these areas shows active growth of fibroblasts and deposition of collagen with minimal white cell infiltration (FIG. 20). Split thickness wounds showed remarkable differences in contraction, epithelialization, pigmentation, and hair growth when comparing wound treated with dermal equivalent (left) and biodegradable mesh alone (right) (FIG. 21). Mesh soaked with fibroblast cell lysate showed an enhancement of epithelial growth around mesh fiber (FIG. 22), but an overall slower healing progress than in areas treated with living neodermis.

Neodermis enhanced epithelial migration onto the healing area. As seen in FIG. 23, deep rete pegs are formed by the keratinocytes as they migrate onto and attach to the living dermal equivalent. This pattern is characteristic of epithelialization in healing areas.

Autologous keratinocytes attached well and had even healing onto the neodermis. FIG. 24 illustrates the comparison of healing of a wound—half of which has received an autologous epithelial graft and half of which received neodermis alone. The epithelial graft healed evenly, prevented further contraction, and firmly attached to the underlying dermal equivalent. FIG. 25 shows the even growth and attachment of the epidermal cells to the neodermis. The neodermis appeared to consist of actively growing fibroblasts and naturally-secreted fibroblasts. The mesh fibers were still present as seen in cross-section.

19.3. Discussion

Transplantation experiments to date have indicated that the neodermis (fibroblasts and naturally secreted collagen on the biodegradable mesh) provides an excellent treatment for full-thickness wounds. Successful use of xenogeneic transplants illustrates the ability to utilize allogeneic neodermis in burn victims and patients with decubitus ulcers. The transplants allow migration of epithelial cells onto the implanted surface as well as support and growth of autologous epithelial sheets. Grafts were permanent, with no evidence of either superficial or deep scarring after four months.

What is claimed is:

1. A three-dimensional tumor culture, comprising tumor cells cultured on a living stromal tissue prepared in vitro, comprising stromal cells and connective tissue proteins naturally secreted by the stromal cells attached to and substantially enveloping a framework composed of a biocompatible, non-living material formed into a three-dimensional structure having interstitial spaces bridged by the stromal cells.

2. The three-dimensional cell culture of claim 1 in which the stromal cells are fibroblasts.

3. The three-dimensional cell culture of claim 1 in which the stromal cells are a combination of fibroblasts and endothelial cells, pericytes, macrophages, monocytes, leukocytes, plasma cells, mast cells or adipocytes.

4. The three-dimensional cell culture of claim 1 in which the framework is composed of a biodegradable material.

5. The three-dimensional cell culture of claim 4 in which the biodegradable material is cotton, polyglycolic acid, cat gut sutures, cellulose, gelatin, or dextran.

6. The three-dimensional cell culture of claim 1 in which the framework is composed of a non-biodegradable material.

7. The three-dimensional cell culture of claim 6 in which the non-biodegradable material is a polyamide, a polyester, a polystyrene, a polypropylene, a polyacrylate, a polyvinyl, a polycarbonate, a polytetrafluorethylene, or a nitrocellulose compound.

8. The three-dimensional cell culture of claim 4, 5, 6 or 7 in which the framework is pre-coated with collagen.

9. The three-dimensional cell culture of claim 1, 2, 3, 4, 5, 6 or 7 in which the framework is a mesh.

10. The three-dimensional cell culture of claim 8 in which the framework is a mesh.

11. A method for culturing tumor cells in vitro, comprising culturing tumor cells inoculated onto a living stromal tissue prepared in vitro, comprising stromal cells and connective tissue proteins naturally secreted by the stromal cells attached to and substantially enveloping a framework composed of a biocompatible, non-living material formed into a three-dimensional structure having interstitial spaces bridged by the stromal cells.

12. The method according to claim 11 in which the stromal cells are fibroblasts.

13. The method according to claim 11 in which the stromal cells are a combination of fibroblasts and endothelial cells, pericytes, macrophages, monocytes, leukocytes, plasma cells, mast cells or adipocytes.

14. The method according to claim 11 in which the framework is composed of a biodegradable material.

15. The method according to claim 14 in which the biodegradable material is cotton, polyglycolic acid, cat gut sutures, cellulose, gelatin, or dextran.

16. The method according to claim 11 in which the framework is composed of a non-biodegradable material.

17. The method according to claim 16 in which the non-biodegradable material is a polyamide, a polyester, a polystyrene, a polypropylene, a polyacrylate, a polyvinyl, a polycarbonate, a polytetrafluorethylene, or a nitrocellulose compound.

18. The method according to claim 14, 15, 16 or 17 in which the framework is pre-coated with collagen.

19. The method according to claim 11, 12, 13, 14, 15, 16 or 17 in which the framework is a mesh.

20. The method according to claim 18 in which the framework is a mesh.

21. A method for transplantation or implantation of tumor cells into non-human animals which comprises implanting in vivo the tumor cells cultured on a living stromal tissue prepared in vitro, comprising stromal cells and connective tissue proteins naturally secreted by the stromal cells attached to and substantially enveloping a framework composed of a biocompatible, non-living material formed into a three-dimensional structure having interstitial spaces bridged by the stromal cells so that a tumor is formed.

22. The method according to claim 21 in which the stromal cells are fibroblasts.

23. The method according to claim 21 in which the stromal cells are a combination of fibroblasts and endothelial cells, pericytes, macrophages, monocytes, leukocytes, plasma cells, mast cells or adipocytes.

24. The method according to claim 21 in which the framework is composed of a biodegradable material.

25. The method according to claim 24 in which the biodegradable material is cotton, polyglycolic acid, cat gut sutures, cellulose, gelatin, or dextran.

26. The method according to claim 21 in which the framework is composed of a non-biodegradable material.

27. The method according to claim 26 in which the non-biodegradable material is a polyamide, a polyester, a polystyrene, a polypropylene, a polyacrylate, a polyvinyl, a polycarbonate, a polytetrafluorethylene, or a nitrocellulose compound.

28. The method according to claim 24, 25, 26 or 27 in which the framework is pre-coated with collagen.

29. The method according to claim 21, 22, 23, 24, 25, 26 or 27 in which the framework is a mesh.

30. The method according to claim 28 in which the framework is a mesh.

31. A method for testing the effect of a drug comprising:
   (a) exposing a three-dimensional tumor cell culture to the drug, in which the three-dimensional cell culture comprises tumor cells grown on a living stromal tissue prepared in vitro, comprising stromal cells and connective tissue proteins naturally secreted by the stromal cells attached to and substantially enveloping a framework composed of a biocompatible, non-living material formed into a three-dimensional structure having interstitial spaces bridged by the stromal cells; and
   (b) determining the effect of the drug on the cells in culture.

32. The method for testing the effect of a drug according to claim 31 in which the stromal cells are fibroblasts.

33. The method for testing the effect of a drug according to claim 31 in which the stromal cells are a combination of fibroblasts and endothelial cells, pericytes, macrophages, monocytes, leukocytes, plasma cells, mast cells or adipocytes.

34. The method for testing the effect of a drug according to claim 31 in which the framework is composed of a biodegradable material.

35. The method for testing the effect of a drug according to claim 34 in which the biodegradable material is cotton, polyglycolic acid, cat gut sutures, cellulose, gelatin, or dextran.

36. The method for testing the effect of a drug according to claim 31 in which the framework is composed of a non-biodegradable material.

37. The method for testing the effect of a drug according to claim 36 in which the non-biodegradable material is a polyamide, a polyester, a polystyrene, a polypropylene, a polyacrylate, a polyvinyl, a polycarbonate, a polytetrafluorethylene, or a nitrocellulose compound.

38. The method for testing the effect of a drug according to claim 34, 35, 36 or 37 in which the framework is pre-coated with collagen.

39. The method according to claim 31, 32, 33, 34, 35, 36 or 37 in which the framework is a mesh.

40. The method according to claim 38 in which the framework is a mesh.

41. A method for diagnosing or monitoring a malignancy in a patient, comprising:
   (a) inoculating tumor cells obtained from the patient onto a living stromal tissue prepared in vitro, comprising stromal cells and connective tissue proteins naturally secreted by the stromal cells attached to and substantially enveloping a framework composed of a biocompatible, non-living material formed into a three-dimensional structure having interstitial spaces bridged by the stromal cells;
   (b) culturing the inoculated living stromal tissue in a nutrient medium so that the inoculated cells proliferate in culture; and
   (c) determining the presence of malignant cells in the proliferated cells in culture.

42. The method for diagnosing or monitoring a malignancy according to claim 41 in which the stromal cells are fibroblasts.

43. The method for diagnosing or monitoring a malignancy according to claim 41 in which the stromal cells are a combination of fibroblasts and endothelial cells, pericytes, macrophages, monocytes, leukocytes, plasma Cells, mast cells or adipocytes.

44. The method for diagnosing or monitoring a malignancy according to claim 41 in which the framework is composed of a biodegradable material.

45. The method for diagnosing or monitoring a malignancy according to claim 44 in which the biodegradable material is cotton, polyglycolic acid, cat gut sutures, cellulose, gelatin, or dextran.

46. The method for diagnosing or monitoring a malignancy according to claim 41 in which the framework is composed of a non-biodegradable material.

47. The method for diagnosing or monitoring a malignancy according to claim 46 in which the non-biodegradable material is a polyamide, a polyester, a polystyrene, a polypropylene, a polyacrylate, a polyvinyl, a polycarbonate, a polytetrafluorethylene, or a nitrocellulose compound.

48. The method for diagnosing or monitoring a malignancy according to claim 44, 45, 46 or 47 in which the framework is pre-coated with collagen.

49. The method for diagnosing or monitoring a malignancy according to claim 41, 42, 43, 44, 45, 46 or 47 in which the framework is a mesh.

50. The method according to claim 48 in which the framework is a mesh.

51. The method for diagnosing or monitoring malignancy according to claim 41 in which the tumor cells are hematopoietic cells.

52. The method for diagnosing or monitoring a malignancy according to claim 41 in which the tumor cells are melanocyte or keratinocyte cells.

53. The method for diagnosing or monitoring a malignancy according to claim 41 in which the tumor cells are liver parenchymal cells.

54. The method for diagnosing or monitoring a malignancy according to claim 41 in which the tumor cells are pancreatic acinar cells.

55. The method for diagnosing or monitoring a malignancy according to claim 41 in which the tumor cells are kidney parenchymal cells.

56. The method for diagnosing or monitoring a malignancy according to claim 41 in which the tumor cells are mucosal epithelium cells.

57. A method for diagnosing or monitoring a malignancy in a patient comprising:
   (a) inoculating astrocytes from a tumor cell sample obtained from the patient onto a living stromal tissue prepared in vitro comprising confluent endothelial cells attached to and substantially enveloping a framework composed of a biocompatible non living material formed into a three-dimensional structure having interstitial spaces bridged by the endothelial cells;

(b) inoculating further onto said astrocytes, neuron cells from the sample obtained from the patient;

(c) culturing the inoculated living stromal tissue in a nutrient medium so that the inoculated cells proliferate in culture; and (d) determining the presence of malignant astrocyte cells in the proliferated cells in culture.

58. A method for diagnosing or monitoring a malignancy in a patient comprising (a) inoculating astrocytes from a tumor cell sample obtained from the patient onto a living stromal tissue prepared in vitro comprising confluent endothelial cells attached to and substantially enveloping a framework composed of a biocompatible non-living material formed into a three-dimensional structure having interstitial spaces bridged by the endothelial cells;

(b) inoculating further onto said astrocytes, neuron cells from the sample obtained from the patient;

(c) culturing the inoculated living stromal tissue in a nutrient medium so that the inoculated cells proliferate in culture; and (d) determining the presence of malignant neuron cells in the proliferated cells in culture.

* * * * *